US011826237B2

(12) United States Patent
Luukko et al.

(10) Patent No.: US 11,826,237 B2
(45) Date of Patent: Nov. 28, 2023

(54) MEDICAL PRODUCT AND METHOD FOR PREPARING THEREOF

(71) Applicant: UPM-Kymmene Corporation, Helsinki (FI)

(72) Inventors: Kari Luukko, Espoo (FI); Markus Nuopponen, Helsinki (FI); Lauri Paasonen, Järvenpää (FI); Mika Kosonen, Lappeenranta (FI); Saara Laitinen, Helsinki (FI); Lindsay Davies, Munich-Obersendling (DE); Sami Valkonen, Kuopio (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 253 days.

(21) Appl. No.: 17/063,853

(22) Filed: Oct. 6, 2020

(65) Prior Publication Data

US 2021/0128365 A1    May 6, 2021

(30) Foreign Application Priority Data

Oct. 31, 2019  (EP) .................................. 19397531

(51) Int. Cl.
  *A61F 13/02*    (2006.01)
  *A61L 15/28*    (2006.01)
  *A61F 13/00*    (2006.01)

(52) U.S. Cl.
  CPC ...... *A61F 13/0276* (2013.01); *A61F 13/0206* (2013.01); *A61L 15/28* (2013.01);
  (Continued)

(58) Field of Classification Search
  CPC .............. A61F 13/0276; A61F 13/0206; A61F 2013/00157; A61F 2013/0054;
  (Continued)

(56) References Cited

U.S. PATENT DOCUMENTS 4,233,976 A * 11/1980 Dunshee ................ A61L 15/18
  602/45
7,252,837 B2 * 8/2007 Guo ...................... A61L 15/425
  424/443
(Continued)

FOREIGN PATENT DOCUMENTS

CA     3008713 A1    7/2017
CN     1426316 A  *  6/2003    ............. A61L 15/22
(Continued)

OTHER PUBLICATIONS

Translation of JP-H08322876-A (Year: 1996).*
(Continued)

*Primary Examiner* — Rachael E Bredefeld
*Assistant Examiner* — Seth R. Brown
(74) *Attorney, Agent, or Firm* — CANTOR COLBURN LLP

(57) ABSTRACT

The present application relates to a method for preparing a medical product, the method comprising providing an aqueous dispersion of nanofibrillar cellulose, providing a nonwoven fabric, immersing the nonwoven fabric in the aqueous dispersion of nanofibrillar cellulose to form a coating on the nonwoven fabric, passing the immersed nonwoven fabric through a prefined gap to define the thickness of the coating on the immersed nonwoven fabric without pressing, and dewatering the immersed nonwoven fabric, to obtain the medical product. The present application also relates to a medical product comprising a supporting layer and an absorbent layer, wherein the supporting layer comprises a nonwoven fabric, and the absorbent layer comprises unpressed nanofibrillar cellulose having an average fibril diameter of 200 nm or less, wherein the absorbent layer is coating the supporting layer.

31 Claims, 17 Drawing Sheets

(52) U.S. Cl.
CPC ............... *A61F 2013/0054* (2013.01); *A61F 2013/00157* (2013.01)

(58) Field of Classification Search
CPC ........ A61F 13/0243; A61F 2013/00744; A61F 2013/15934; A61L 15/28
See application file for complete search history.

(56) References Cited

U.S. PATENT DOCUMENTS

| | | | |
|---|---|---|---|
| 10,113,005 B2 * | 10/2018 | Häggblom | C08B 15/02 |
| 2014/0121622 A1 * | 5/2014 | Jackson | A61L 15/60 |
| | | | 428/401 |
| 2015/0367024 A1 * | 12/2015 | Laukkanen | A61L 26/0023 |
| | | | 424/444 |
| 2018/0015194 A1 * | 1/2018 | Sone | B01J 20/24 |
| 2018/0022908 A1 * | 1/2018 | Akihama | B29B 9/14 |
| | | | 522/89 |
| 2018/0282923 A1 * | 10/2018 | Carlyle | D04H 3/02 |
| 2019/0167798 A1 * | 6/2019 | Kawashima | A61L 15/00 |

FOREIGN PATENT DOCUMENTS

| | | | | |
|---|---|---|---|---|
| CN | 203128835 U | * | 8/2013 | |
| CN | 108339145 A | * | 7/2018 | ............ A61L 15/20 |
| EP | 2561843 A2 | | 2/2013 | |
| EP | 3187195 A1 | * | 7/2017 | ....... A61F 13/00012 |
| EP | 3228329 A1 | | 10/2017 | |
| EP | 3335740 A1 | * | 6/2018 | ............ A61L 15/28 |
| JP | H08322876 A | * | 12/1996 | ....... A61F 13/00012 |
| JP | H08322876 A | | 12/1996 | |
| JP | 2009263495 A | * | 11/2009 | ............ B32B 23/02 |
| JP | 2017506924 A | * | 3/2017 | ............ A61F 13/023 |
| WO | WO-0119306 A1 | * | 3/2001 | ............ A61F 13/023 |
| WO | WO-2013060934 A2 | * | 5/2013 | ............ B32B 23/02 |
| WO | WO-2014128354 A1 | * | 8/2014 | ............ A61L 15/28 |
| WO | WO-2019166606 A1 | * | 9/2019 | ............ A61K 38/19 |

OTHER PUBLICATIONS

Translation of CN-1426316-A (Year: 2003).*
Translation of JP-2009263495-A (Year: 2009).*
Translation of JP-2017506924-A (Year: 2017).*
Translation of CN-108339145-A (Year: 2018).*
Translation of CN-203128835-U (Year: 2013).*

* cited by examiner

MEDICAL PRODUCT AND METHOD FOR PREPARING THEREOF

CROSS REFERENCE TO RELATED APPLICATION

This application claims benefit of European Application No. 19397531.5 filed on Oct. 31, 2019, which is incorporated by reference herein in its entirety.

TECHNICAL FIELD

The present application relates to a method for preparing a medical product and to a medical product. More particularly the present application relates to a nonwoven coated with nanofibrillar cellulose for use as a wound dressing.

BACKGROUND

In wound healing it is often necessary to cover the wound with a suitable dressing to protect the wound from infections and mechanical stress and to allow healing of the wound. Many types of conventional dressings tend to stick to the wound and may even damage the wound when moved or removed. The conditions at the wound are not optimal for the healing process.

It is therefore desired to obtain wound care products having properties which enable better healing of the wound and which do not damage the wound. It is also desired to be able to control the healing process.

SUMMARY

Wound healing is based on complex biological mechanisms in which cells produce different biomolecules, such as growth factors and proteins, which steer and activate wound healing process and its phases.

It was found out how a wound dressing comprising a nonwoven having a specific absorbent layer of nanofibrillar cellulose could enhance the healing process of the wound and provide better handling and usability of the dressing. The dressing could provide conditions which enabled controlling the flow of active biomolecules from the wound and back, which phenomena was found useful in activating, controlling and optimizing the healing process of the wound.

The present application provides a method for preparing a medical product, the method comprising
  providing an aqueous dispersion of nanofibrillar cellulose,
  providing a nonwoven fabric,
  immersing the nonwoven fabric in the aqueous dispersion of nanofibrillar cellulose to form a coating on the nonwoven fabric,
  passing the immersed non-woven fabric through a prefined gap to define the thickness of the coating on the immersed nonwoven fabric without pressing, and dewatering the immersed nonwoven fabric,
  optionally repeating the immersing and passing through the gap at least once, to obtain the medical product.

The present application provides a medical product comprising a supporting layer and an absorbent layer as a coating on the supporting layer, wherein the supporting layer comprises a nonwoven fabric, and the absorbent layer comprises unpressed nanofibrillar cellulose having an average fibril diameter of 200 nm or less.

The present application provides the medical for use for treating skin wound in a method comprising applying the product onto the wound to absorb bioactive agents from the wound, storing the bioactive agents in the medical product for a period of time, and allowing the bioactive agents to diffuse back to the wound at a later phase of the healing process of the wound.

The main embodiments are characterized in the independent claims. Various embodiments are disclosed in the dependent claims. The embodiments and examples recited in the claims and in the specification are mutually freely combinable unless otherwise explicitly stated.

The impregnated medical products described herein are useful in medical applications, wherein the materials comprising nanofibrillar cellulose are in contact with living tissue. It was discovered that nanofibrillar cellulose (NFCI provides advantageous properties when it is applied for example onto skin.

The products containing nanofibrillar cellulose as described herein are non-cytotoxic and highly biocompatible with the living tissue and provide several advantageous effects. Without binding to any specific theory, it is believed that the impregnated medical product comprising nanofibrillar cellulose provides a very hydrophilic surface, which, when applied against a skin or other tissue, for example a skin graft wound, absorbs and retains water from the tissue and forms a water film between the medical product and the tissue promoting the healing of the wound. The medical product may be also be moistened to enhance the effect. The surface of the product having a higher concentration of nanofibrillar cellulose can maintain these highly hydrophilic conditions even though the inside of the product has a lower concentration of nanofibrillar cellulose. It is possible to obtain features like lower density and other physical properties of the whole product, while providing the advantageous properties of the nanofibrillar cellulose at a desired location.

As the content of nanofibrillar cellulose is higher at the surfaces and/or near the surfaces of the nonwoven and lower at the centre of the nonwoven in the cross sectional direction, i.e. between the surfaces, several functionalities are obtained. First of all, the relatively higher concentration of NFC at the surfaces of the nonwoven, especially when present as a coating layer with suitable thickness and/or density, creates a barrier, which may block or slow down flow of substances though the barrier. For example the barrier may limit the flow of biological molecules so that it may take a while for the biological molecules to enter and pass the barrier, and after passing the barrier the molecules are contained inside the nonwoven wherein the content of NFC is lower. In this way a reservoir of biological substance having fluid retention properties is formed, and the substances remain active in the conditions inside the nonwoven. Therefore, when the impregnated nonwoven is applied onto a wound, the biological molecules from the wound can enter the nonwoven after a delay, and remain in the nonwoven. Further, the biological molecules may also diffuse to opposite direction back to the nonwoven after a period of time. Without binding to any specific theory, it is believed that this phenomena somehow creates conditions which enhance the healing of the wound. It may be possible that by storing a portion of the specific biological molecules secreted to the wound when the dressing is applied and/or at the early phase of the wound healing, and providing these molecules back to the wound at a later phase when the healing conditions have changed in the wound and the wound may contain a different spectrum of biological molecules, the healing of the wound is improved or enhanced. It may be also possible that it is advantageous merely to remove some of the biological molecules present in the wound to the dressing to enhance healing. Despite of the exact mechanisms involved, it was found out that by using the coated and impregnated nonwoven disclosed herein it was possible to enhance the healing of the wound.

The layer or zone of nanofibrillar cellulose was found to act as an absorbent layer, which provided said properties. Especially it was found advantageous that a separate coating on top of the supporting and reinforcing nonwoven layer was present to provide the absorbent and fluid retention properties, but also the feature that the coating layer is continued into the nonwoven as an impregnated in a decreasing manner was found to enhance the desired functional and mechanical properties of the medical product. On the other hand, as the nonwoven was not thoroughly impregnated with the nanofibrillar cellulose, the support properties of the nonwoven were enhanced.

Further, as the nonwoven contains more concentrated NFC areas at the both sides, the medical product may be applied to a wound or other target with either side against the target. This enhances the usability of the product. Also, as the side not against the wound or skin also contains a barrier-forming NFC, the outer side of the medical product is protected from contamination, especially against microbes and large molecules, proteins, fat and the like. However, gases may pass the barrier, which may enhance the healing conditions inside the wound as less anaerobic conditions are formed and/or maintained. Therefore it is not necessary to cover the medical product with a cover layer, such as plastic or the like, which makes the medical product especially when used as a dressing, simple, air permeable, biodegradable and recyclable. The medical product with two practically identical sides can be formed in a simple process. It is also possible to form a product with different sides, for example comprising a unpressed coating on one side and a different coating, such as fully or partly pressed, on the opposite side.

The medical products disclosed herein provide high absorption capacity and absorption speed, which properties are desired in medical applications such as wound healing and the like. Large sheets may be prepared which may be used for covering large areas.

When the impregnated products are used for covering wounds or other damages or injuries, for example in products such as plasters, dressings, medical patches or parts of plasters, patches or dressings, several effects are provided. The usability of the products is good as the product may be applied and removed easily without being damaged, for example torn. The product may also be cut into a desired size and shape without affecting the properties thereof. When used for covering wounds the material of the impregnated product acts as an artificial skin, which protects the wound and will come loose when the wound heals. The impregnated product will not attach to a damaged skin in such irreversible way as conventional materials, which are usually very difficult to remove without damaging the healed area. The conditions between the impregnated product and the skin facilitate the healing of a damaged area.

The medical products can be used in the treatment of grafts, such as skin graft. The impregnated product may be used for covering the graft area and it acts as a protective layer. As the graft heals, the impregnated product forms a scab-like structure, which promotes the healing.

The wounds treated with the NFC wound dressings were found to exhibit better scar quality after healing when compared to products containing only nonwoven or other polymeric supports but not NFC.

BRIEF DESCRIPTION OF THE FIGURES

FIG. 19A shows two blades forming a gap g between the blades, and FIG. 19B shows two rollers forming a gap g between the rollers.

DETAILED DESCRIPTION

Figure 1:
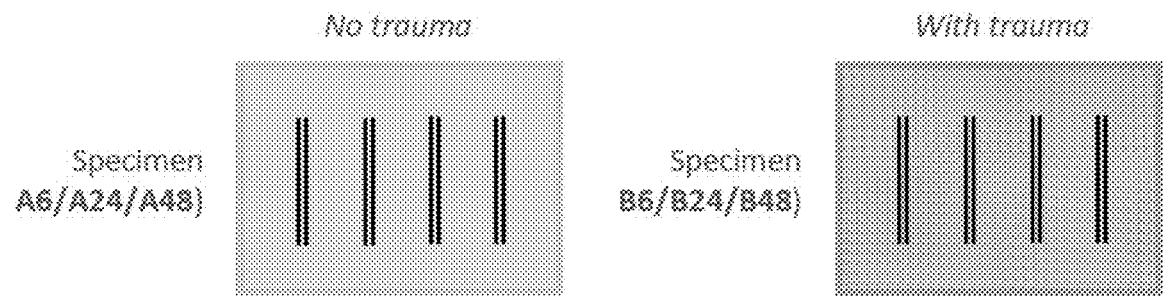
FIG. 1 shows schematic drawing of the experimental setup in the pre-phase.

In this specification, percentage values, unless specifically indicated otherwise, are based on weight (w/w). If any numerical ranges are provided, the ranges include also the upper and lower values. The open term "comprise" also includes a closed term "consisting of" as one option.

The present application provides a medical product and a method for preparing a medical product. The terms such as "medical product", "coated product", "impregnated product", "coated and impregnated product" or "impregnated medical product", or more particularly "medical product coated and impregnated with nanofibrillar cellulose" and the like terms, which terms may be used interchangeably, refer to a product comprising a nonwoven or a layer of nonwoven treated with nanofibrillar cellulose as described herein. The medical product may also be called as a medical structure. The impregnated product may be obtained with the preparation methods described herein.

The medical products obtained with the immersing and/or impregnation process differ from products obtained by coating or layering methods, for example products obtained by blade coating or by laminating. Such a layered product contains separate layers which may be detected from the final products for example by dying and/or using microscopic methods, and the separate layers may be even separated by peeling. In a product obtained by the process described herein the nanofibrillar cellulose is distributed as a coating on the nonwoven and also on the fibers of the nonwoven, and it also penetrates at least partly inside the nonwoven. Further the product obtained by immersing/impregnating has more open structure having a high air and liquid permeability. A coating layer with desired concentration, density, thickness, and surface properties can be obtained on the nonwoven. When using immersing/impregnating process substantially low amounts of nanofibrillar cellulose may be used. The nanofibrillar portion of the product is practically inseparable from the nonwoven. Immersing enables producing a coating, which continues as an impregnated into the nonwoven. On the other hand, products obtained with methods utilizing vacuum or pressure are also different from the present products, as the distribution of nanofibrillar cellulose in the product is different and similar coating layer cannot be maintained. The present method enables maintaining a separate coating layer with desired thickness, density, concentration and surface properties such as smoothness, permeability, and the like as described herein, and also uneven or partial impregnation in the nonwoven fabric, and these are fixed in the dewatering. Using vacuum or pressure would destroy these structures.

The term "medical" refers to a product or use wherein the product is used or is suitable for medical purposes. A medical product may be sterilized, or it is sterilisable, for example by using temperature, pressure, moisture, chemicals, radiation or a combination thereof. The product may be for example autoclaved, or other methods using high temperature may be used, in which cases the product should tolerate high temperatures over 100° C., for example at least 121° C. or 134° C. In one example the product is autoclaved at 121° C. for 15 minutes. Also UV or gamma radiation sterilization may be used. A medical product may also be suitable for example for cosmetic purposes.

The medical product provides enhanced mechanical strength and other properties, such as high tear strength (tear resistance), especially at moist conditions. By combining a supporting and reinforcing nonwoven structure, such as a dressing fabric, such as a gauze, with nanofibrillar cellulose an impregnated product is formed. The fabric creates a continuous supporting network and the strength of the network is not significantly affected by moist conditions.

Certain advantageous properties of the medical products include flexibility, elasticity and remouldability. If the nanofibrillar cellulose contains moisture, it may also show suitable permeability. These properties are useful for example when the impregnated product is used as a dressing for healing wounds, or in other medical applications, such as for delivering therapeutic or cosmetic agents.

Flexibility is a feature which is desired in many applications, such as in medical applications. Flexible patches and dressings comprising nanofibrillar cellulose are useful for applying onto skin, for example for covering wounds and other damages or injuries, such as burns.

The relatively low amount and specific distribution of the nanofibrillar cellulose in the product has impacts to flexibility, elasticity, remouldability and rigidity. The rigidity of the impregnated product is relatively low and the product has an open structure which provides suitable air and/or liquid permeability.

The flexibility or elasticity (elongation) of the product can also be affected with the choice of the nonwoven. The nanofibrillar cellulose itself has a limited flexibility and elasticity, especially when dry. For this reason it is important to match the nonwoven and the network of nanofibrillar cellulose to obtain a balance between the elastic properties of nonwoven and nanofibrillar cellulose network. This was obtained in the present case wherein the absorbent layer and supporting layer could be provided in functional balance.

The method comprises providing an aqueous dispersion of nanofibrillar cellulose. The nanofibrillar cellulose may be as disclosed or defined in this disclosure. Chemically unmodified and chemically anionically modified nanofibrillar cellulose are preferred in most applications. The nanofibrillar cellulose should have adequate degree of fibrillation so that the desired properties and effects are obtained.

The content of the nanofibrillar cellulose in the dispersion may be 2% (w/w) or less, or 1.5% (w/w) or less, or 1.2% (w/w) or less, such as in the range of 0.5-1.5% (w/w), preferably 0.7-1.2% (w/w), or most preferably in the range of 0.8-1.0% (w/w). It was found out that when using concentrations higher than 1.2% (w/w), it was difficult to obtain even coating but the material tend to clot, which led poor quality coating and surface thereof This may also depend of the desired degree or impregnation and/or degree of coating. In said ranges the nanofibrillar cellulose is present as a viscous hydrogel, which has specific properties characteristic for non-Newtonian fluids, and which also exhibits very hydrophilic properties. Therefore features, such as degree of penetration or impregnation, attachment to the nonwoven, viscosity and the like properties of the hydrogel having an impact to the processability and to the obtained structure, are also affected by the concentration of the dispersion. For example if using higher NFC concentration, the hydrogel may be stronger and may tolerate mechanical manipulation better than more dilute hydrogel. On the other hand, a more dilute hydrogel could penetrate the nonwoven deeper and/or faster, and it could form a thinner coating in the immersing step. The dispersion, which may have been formed to water or to water containing one or more additive(s), may contain nanofibrillar cellulose as the only or substantially only solid matter, optionally also including any suitable additives and/or auxiliary agents, or the nanofibrillar cellulose may be the only fibrous or fibrillar material in the dispersion.

In one embodiment the nanofibrillar cellulose has an average diameter of a fibril in the range of 1-200 nm, such as 1-50 nm, and/or, when dispersed in water, provides a storage modulus of 350 Pa or more, such as in the range of 350-5000 Pa, or preferably 350-1000 Pa, and yield stress of 25 Pa or more, such as in the range of 25-300 Pa, preferably 25-75 Pa, determined by rotational rheometer with gradually increasing shear stress in a range of 0.001-100 Pa at a frequency 10 rad/s, strain 2%, at 25° C.

In one embodiment the nanofibrillar cellulose comprises or is chemically anionically modified nanofibrillar cellulose having an average diameter of a fibril of 50 nm or less, such as in the range of 1-50 nm. Such highly fibrillated chemically modified nanofibrillar cellulose was found to enhance the absorbing and retaining of bioactive agents in the medical product, as well as barrier properties and mechanical properties. Especially such nanofibrillar cellulose exhibits good low swelling characteristics for the absorbent layer when exposed to liquid.

The method also comprises providing a nonwoven fabric. The nonwoven or nonwoven fabric, which terms may be used interchangeably, as used herein refer to any suitable nonwoven, such as a fabric, a cloth or the like material comprising fibers, for example a gauze. The nonwoven may be sterile or nonsterile, plain or impregnated, or fenestrated (perforated or with slits), or a combination thereof. The nonwoven may be provided as a nonwoven sheet or fabric or the like.

A nonwoven, such as a nonwoven fabric, may be provided as a flat sheet. A nonwoven has two sides; a first side and a second side opposite to the first side. These are the sides with largest areas. The operations disclosed herein may be directed to or carried out on one or both sides of the nonwoven, and the obtained structures discussed herein, such as the coatings, may be on one or both sides of the nonwoven.

The nonwoven may comprise natural fibers, semi-synthetic fibers or synthetic fibers, such as viscose, rayon, polypropylene, polyester and the like, or combinations thereof, for example a viscose-polyester mixture or a mixture of cellulose (pulp) and polypropylene and/or polyester. When used as a medical dressing, the nonwoven may be made of cotton. The nonwoven may also act as a pad of a patch. In one embodiment the nonwoven is viscose-polyester nonwoven fabric, for example a gauze. Such a nonwoven fabric is very porous and permeable and it is moderately elastic providing irreversible elongation in one direction.

In one embodiment the nonwoven is a gauze. Nonwoven gauze comprises fibers pressed together to resemble a weave, which provides improved wicking and greater absorbent capacity. Compared to woven gauze, this type of gauze produces less lint and has the benefit of leaving fewer fibers behind in a wound when removed. Examples of nonwoven gauze dressings include gauzes made of polyester, viscose, or blends of these fibers which are stronger, bulkier, and softer than woven pads.

The nonwoven may also take part in absorbing substances, for example to enable the medical product to absorb exudate, to soak up blood, plasma, and other fluids exuded from the wound and containing them in one place. The nonwoven may also stem bleeding and to help sealing a wound. The nonwoven may also contain or absorb a therapeutic agent or other agent.

In one embodiment the nonwoven comprises natural fibers or natural-fiber-based material, such as cotton, cellulose, linen, silk or the like. Natural fibers provide free hydroxyl groups which helps attaching the nonwoven to the layer(s) comprising nanofibrillar cellulose via hydrogen bonds. Also semi-synthetic fibers may provide free hydroxyl groups, such as viscose.

In one embodiment the nonwoven comprises natural nonwoven, such as cellulose or cotton nonwoven, synthetic nonwoven or semi-synthetic nonwoven, or a mixture thereof. In one example the nonwoven comprises a mixture of polypropylene and cellulose. In one example the nonwoven comprises a mixture of polypropylene, polyester and cellulose. In one example the nonwoven comprises a mixture of viscose and polypropylene. In one example the nonwoven comprises a mixture of viscose and polyester. Cellulose fibers may be mixed with these materials. These nonwovens may comprise or be gauzes.

The nonwoven should be highly permeable allowing fluids to pass through. The nonwoven is not a filter and it does not limit the flow through of most macromolecules. The nonwoven may not be used as a filter for dewatering a dispersion comprising nanofibrillar cellulose. The nonwoven may be porous and/or it may be fenestrated having perforations or slits or the like. A paper or cardboard is not a nonwoven. More particularly paper is not suitable as paper does not provide high enough tear strength in such grammages or thicknesses which would be suitable for the present products. The same applies to cardboard or other similar cellulosic products. Nonwovens differ from papers and cardboards usually in that the nonwovens comprise longer fibers, such as having an average length of at least 4 mm, such as at least 5 mm. Nonwovens do not usually contain such fillers as are used in papers and cardboards, such as inorganic fillers, sizing agents, retention agents and the like. In one example the nonwoven is non-cellulosic.

In one example the nonwoven is resilient. Many natural, semi-synthetic or synthetic fibers are resilient. However, in one example the nonwoven is rigid providing non-resilient properties, for example when it comprises cotton. The nonwoven may provide reinforcing properties, for example to enhance the tear strength of the medical product.

Tear strength (tear resistance) is a measure of how well a material can withstand the effects of tearing. More specifically it measures how well a material resists the growth of any cuts when under tension. Tear resistance may be measured by the ASTM D 412 method (the same may be used to measure tensile strength, modulus and elongation). Also a tear index may be presented, wherein tear index=tear strength/grammage, and it is usually measured in $mNm^2/g$.

The nonwoven may have a tear strength in the range of 800-2000 mN. Tear index may be measured with ISO 1974. The tensile strength of a nonwoven may be for example in the range of 0.6-1.5 kN/m, such as 0.7-1.2 kN/m. Tensile strength may be measured by ISO 1924-3. The nonwoven may have a grammage in the range of 20-60 $g/m^2$, for example in the range of 30-55 $g/m^2$ or 40-50 $g/m^2$. Grammage may be measured by ISO 536. The nonwoven may have a density for example in the range of 100-400 $g/cm^3$, such as in the range of 160-330 $g/cm^3$. Also a bulk may be presented as $cm^3/g$, measured by ISO 534.

A nonwoven, such as a dry nonwoven, may have a thickness in the range of 100-1000 µm, such as 100-200 µm, 150-200 µm, 150-300 µm, 200-300 µm, 300-400 µm, 400-500 µm, 500-600 µm, 600-700 µm, 700-800 µm, 800-900 µm or 900-1000 µm. However, thicker nonwovens may also be used, for example up to 2000 or 3000 µm. In one embodiment the thickness of the nonwoven is in the range of 100-200 µm, such as 100-120 µm, 120-140 µm, or 140-160 µm or 160-190 µm. These thicknesses refer to thicknesses of nonwovens before treatment with the present method. However the thickness after the treatment may be same, or substantially the same, or may contain a further thickness of the coating on one or two side(s) of the nonwoven.

A gauze may comprise natural gauze, such as cellulose or cotton gauze, synthetic gauze or semi-synthetic gauze, such as viscose or polyester, or a mixture thereof. In some embodiments the gauze comprises a mixture of polypropylene and cellulose or a mixture of polypropylene, polyester and cellulose.

The content of cellulose or cellulosic fibers may be 60% (w/w) or more of the nonwoven, or 70% (w/w) or more, such as about 80% (w/w) of the nonwoven, and the rest may be synthetic fibers. In one example the nonwoven comprises about ⅔ of cellulosic fibers and about ⅓ of synthetic fibers, such as polypropylene fibers. In one example the nonwoven comprises about ⅘ of cellulosic fibers and about ⅕ of synthetic fibers. Such combination of cellulose and synthetic fibers provides good attachment of nanofibrillar cellulose to the cellulosic fibers together with structural and mechanical properties provided by the synthetic fibers, such as rigidity.

The method comprises impregnating the nonwoven by immersing in the aqueous dispersion of nanofibrillar cellulose. Immersing refers to a process of soaking, dipping or otherwise completely covering, and/or exposing the nonwoven to or with the dispersion of nanofibrillar cellulose. As the whole nonwoven, which is present in a form of a sheet, layer or the like flat or layered product, may be immersed to the nanofibrillar cellulose dispersion, the both sides of the nonwoven will be in contact with the dispersion so the nanofibrillar cellulose starts penetrating the nonwoven from both sides practically at the same time. This leads to at least partial impregnation of the nonwoven with the dispersion of nanofibrillar cellulose.

Depending on the time the nonwoven is immersed with the aqueous dispersion of nanofibrillar cellulose, the concentration of the dispersion, and for other process conditions and treatment steps, the nonwoven may be first covered with the nanofibrillar cellulose mainly at the surfaces and the areas immediately below the surfaces of the nonwoven. The middle area or the centre area between the surfaces of the nonwoven will receive a smaller portion of the nanofibrillar cellulose. The nonwoven may be immersed for a time period sufficient to obtain a desired impregnation result, such as desired concentration and distribution of nanofibrillar cellulose inside the nonwoven.

During development of the NFC dressings over years different combinations and types of NFC and nonwovens have been tested, such as nonwovens treated by filtering NFC dispersion, for example by using vacuum, or by impregnating and pressing to obtain even distribution of NFC in the nonwoven. However the obtained products and the properties thereof were found to differ from each other, which also has an impact to the effectiveness and type of treatment achieved by using the products. It was challenging to obtain a nonwoven having more concentrated layer or portion of NFC at the surface or near the surface, especially a coating layer, and also a partial impregnation of the nonwoven. Careful control of the manufacturing conditions was required.

Figure 26:
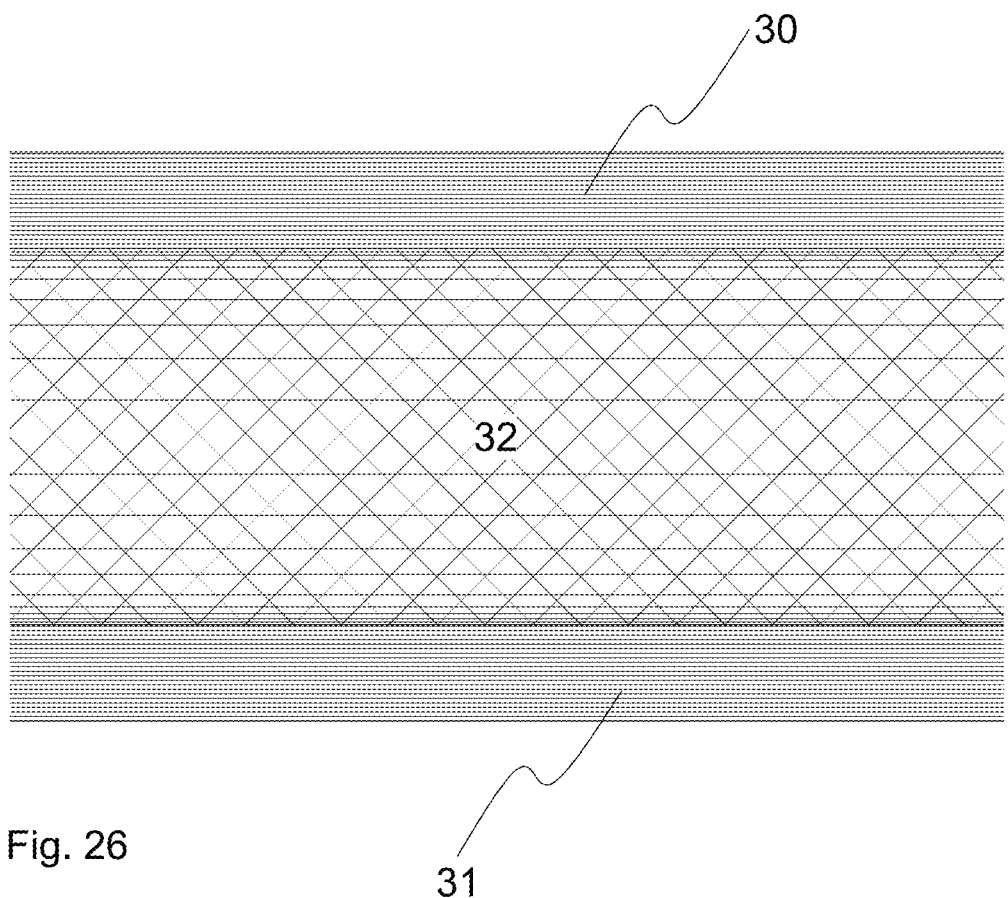
FIG. 26 shows a cross-sectional view of a schematic example of a medical product comprising a layer of nonwoven coated on both sides.

It was also noticed that different preparation methods provided different product which had significantly different properties. For example by using coating methods the nonwoven was not impregnated, and by using impregnating methods including squeezing (pressing), the nanofibrillar cellulose was evenly distributed in the nonwoven and no functional coating layer having suitable thickness, structure and desired properties was obtained. With the present method a coating layer is obtained and the nanofibrillar cellulose is also partially impregnated into the nonwoven in a decreasing manner from a surface towards middle of the nonwoven, for example gradually. FIG. 26 shows an example of a nonwoven fabric 32 coated on both sides with a layer of nanofibrillar cellulose 30, 31. The nonwoven is impregnated with nanofibrillar cellulose with gradually decreasing concentration (shown with horizontal lines) towards the center of the nonwoven 32. The nanofibrillar cellulose continues from the coating layers to the impregnating parts, i.e. there is no discontinuity in the nanofibrillar cellulose.

In the present case it is desired that the nonwoven fabric will be unevenly impregnated in such way that content of the nanofibrillar cellulose near the surfaces of the nonwoven fabric is higher than in the middle of the nonwoven fabric between the surfaces. To facilitate this, certain process steps may be carried out.

The present disclosure provides a medical product comprising a supporting layer and an absorbent layer, wherein the supporting layer is or comprises a nonwoven, and the absorbent layer is or comprises nanofibrillar cellulose. The absorbent layer is coating the supporting layer, the support layer comprises an absorbent layer coating, or the absorbent layer is present as a coating on the supporting layer. More specifically the present disclosure provides a medical product comprising a nonwoven, which may act as a support or supporting layer, and nanofibrillar cellulose coating on the nonwoven, which nanofibrillar cellulose may act as an absorbent or as an absorbent/absorbing layer. The nonwoven may be impregnated with nanofibrillar cellulose, at least partly. The nanofibrillar cellulose in the medical product, in the nonwoven and/or in the absorbent layer or the coating is preferably unpressed and unvacuumed, i.e. obtained without pressing and vacuum.

It was noticed that when the nonwoven fabric was immersed with the dispersion for a controlled time, the surfaces received a higher content of NFC than the area between the surfaces, i.e. the inside of the nonwoven. The "surface" refers to the part of the nonwoven in cross-sectional direction which is at or near of the each surface of the nonwoven. NFC also accumulates on top of the surfaces of the nonwoven. The accumulated NFC forms a coating on the nonwoven fabric, or it may be present as a coating on the nonwoven fabric, such as a coating layer. The nanofibrillar cellulose, especially in the coating layer, forms an absorbent/absorbing part or an absorbent/absorbing layer, which can provide the functionalities disclosed herein.

A dispersion of nanofibrillar cellulose, which may be at the concentration disclosed herein, is provided. The dispersion may be provided in or to a basin or other suitable container. The container is open in such way that it is possible to feed the nonwoven into the container and out therefrom. The container contains NFC dispersion in such amount that enables immersing the nonwoven into the dispersion. The container may be filled with the dispersion continuously or batchwise.

The nonwoven fabric or web may be immersed to the aqueous dispersion of nanofibrillar cellulose for a time period sufficient to obtain a desired degree of grammage and/or thickness of the coating and/or desired degree of impregnation of the nonwoven, such as the uneven impregnation described herein. The web speed may be for example about 0.3-1 m/min. The delay of the nonwoven in the basin or immersing bath may be in the range of 15-90 seconds. However the immersing time may be adjusted according to the need and used materials. The method may comprise immersing the nonwoven fabric in the aqueous dispersion of nanofibrillar cellulose for example for 15-90 seconds. It may be preferred to not use too long immersing time to avoid impregnating the nonwoven throughout. However too short immersing time could result in uncomplete or uneven coating and poor or no impregnation of the nonwoven.

In the immersing step therefore a coating is obtained, formed or laid, more particularly obtained from wet dispersion or hydrogel, on the nonwoven, for example on one or on both sides of the nonwoven. This initial coating has an initial thickness or a first thickness, which may not be the desired thickness and/or the thickness of the intermediate product and/or the final product obtained after dewatering. The initial coating may also have a surface which is not ideal for the final product and needs to be modified. However, it is usually desired to maintain the density and structure of the coating formed by immersing so any method steps involving pressing, vacuum and/or other actions which would alter the density and structure of the coating are preferably avoided. It may be desired to maintain such an unaltered coating on only one or on both sides of the nonwoven.

If the immersed nonwoven is let to dry or stand for a while, the surface of the immersed nonwoven will become less permeable to further impregnation, for example because of so called skin formation, which is a characteristic feature of nanofibrillar cellulose. However, as the aqueous dispersion of nanofibrillar cellulose is in a form of a hydrogel, and is relatively viscous and thick, the immersed nonwoven contains a high amount of the gel-like dispersion and part thereof may need to be removed. It is also desired not to press or squeeze the dispersion into the nonwoven fabric to avoid impregnating the nonwoven fabric throughout. Such pressing or squeezing would also destroy the NFC layer of top of the nonwoven, i.e. the coating layer. Further, as the NFC is present as a viscous hydrogel on the surface, in such pressing steps it may escape the pressure onto the sides of the pressing object and would be lost at least partly.

The immersed nonwoven is run between a prefined gap, which may be for example between a pair of rolls, plates or blades, which do not cause substantial pressure to the nonwoven but removes the excess NFC hydrogel accumulated onto the nonwoven. The initial coating is practically cut in the gap to remove excess material, i.e. the outer part of the initial coating is peeled off. The immersed non-woven is therefore passed through a prefined gap to define the thickness of the coating of the immersed nonwoven containing nanofibrillar cellulose. Also the thickness of the immersed nonwoven may be defined. The prefined gap is configured to not cause pressure to the immersed nonwoven or to the initial coating on at least one side, such as pressure explained herein. Passing through the gap, as well as other method steps involving handling of the intermediate product, is therefore carried out without pressing and preferably also without using vacuum. The prefined gap may have a width equal or higher than the thickness of the nonwoven, such as the thickness of the nonwoven as stretched and/or as immersed. After the gap an intermediate coating is formed having an intermediate thickness or a second thickness.

The nanofibrillar cellulose is present as a viscous hydrogel on the surface of the nonwoven, so passing through the gap mainly removes excess hydrogel and defines the thickness of the product and/or the coating. The NFC hydrogel is such viscous matter that it will not be pressed or squeezed in the arrangements disclosed herein. As a result an unpressed coating layer remains on top of the nonwoven, which coating layer is finally dewatered in the dewatering step resulting in a functional coating layer having necessary thickness in the final product. If the coating was pressed during the process, there would in practice be no separate coating layer, especially such a layer which could provide similar absorbing properties as the present unpressed coating layers.

As a result an unpressed layer of nanofibrillar cellulose is formed, defined or modified on the nonwoven, preferably having a desired thickness. The unpressed layer may be formed on one or two sides of the nonwoven. The unpressed layer may be also called a laid layer. A desired thickness and/or density of the immersed and passed nonwoven is obtained. The surface of the coating after passing the gap is smooth and it also remains smooth also after the subsequent dewatering. This provides advantages in the use of the product and in the functionality of the product. The smooth surface sets perfectly onto the target, such as skin or wound, and allows good contact with the target. The surface treated by passing through the cap also has a desired permeability of gases and molecules or other substances. This facilitates the formation of the conditions between tissue and the NFC coating of the medical product, and also facilitates and enhances the migration of agents or substances between them.

Unpressed may refer to the form of the nanofibrillar cellulose in the medical product, and/or to the form of the whole medical product, and it may also refer to the preparation method, which does not include such steps that would press the nanofibrillar cellulose dispersion and/or hydrogel, and/or the nonwoven, in such extent, that it would be compressed or it would be pressed into the nonwoven. Also a term non-pressed may be used. Vacuum is also included in such undesired method steps. In the preparation non-squeezing and non-vacuuming methods are generally used, which include defining the thickness of the immersed nonwoven fabric and/or the coating in a gap, but which do not press the nanofibrillar cellulose hydrogel into the nonwoven and/or do not press the coating on the surface of the nonwoven. Therefore a coating layer remains on the surface of the fabric, and preferably it is not compressed. Unpressed form is not shaped or obtained by pressing or pressure.

The "unpressed" may comprise unpressed into the nonwoven. The "unpressed" may also refer to unsqueezed. An unpressed coating may refer to a coating obtained by immersing, and preferably modified with methods not disturbing the structure formed in the immersing step. Preferably a structure which is located mostly or substantially on the top of the nonwoven is obtained. Especially an unpressed layer of nanofibrillar cellulose has not been forced into the nonwoven by applying vacuum, pressure or by squeezing. However, some nanofibrillar cellulose dispersion has entered the nonwoven during the immersing. The content of the nanofibrillar cellulose preferably decreases gradually from the surfaces of the nonwoven towards the middle of the nonwoven between the surfaces (FIG. 26). This can be detected from the final product by using microscopic methods, preferably combined with dying of the product. Therefore the final product contains a nanofibrillar cellulose coating and nanofibrillar cellulose impregnated into the nonwoven. However the coating part contains a higher concentration of NFC compared to the inner part of the nonwoven. The coating may contain nanofibrillar cellulose as only or substantially only solid matter, optionally also including any suitable additives and/or auxiliary agents, or the nanofibrillar cellulose may be the only fibrous or fibrillar material in the coating, especially when the product is directly obtained from the manufacturing process. However, during the use and/or prior to the use, the coating, which acts as an absorbent, may contain other agents as well, such as bioactive molecules, pharmaceuticals, additives, and/or the like. Such agents may be added in a further method step to the medical product. Also the area near the surface, such as immediately below the surface of the nonwoven, may have a higher concentration of NFC compared to the NFC concentration at the center or the middle of the nonwoven, for example at least two times higher, at least five times higher or at least 10 times higher concentration.

The immersing may be carried out for a suitable time period to obtain desired degree of impregnation, grammage, distribution and/or desired accumulation of the NFC dispersion onto the nonwoven. The method may comprise letting the nonwoven dry or stand for 0-60 seconds after immersing, such as 1-60 seconds, 5-60 seconds, 1-30 seconds, 1-10 seconds, 1-5 seconds, or even 0-1 seconds if it is desired to limit the degree of impregnation. "After immersing" may refer to a situation wherein the nonwoven is still remained in the soaking, bathing or other immersing process, or to a situation wherein the immersed nonwoven is removed from the immersing step, i.e. wherein the nonwoven is no longer in contact with the immersing dispersion. After this the immersed nonwoven may be provided to the next step, for example by using one or more rolls, such as a pair of rolls, to remove excess hydrogel and possibly to treat the surfaces of the nonwoven to fix and smoothen the obtained surfaces. However in a continuous process there may not be such a separate step.

Figure 19:
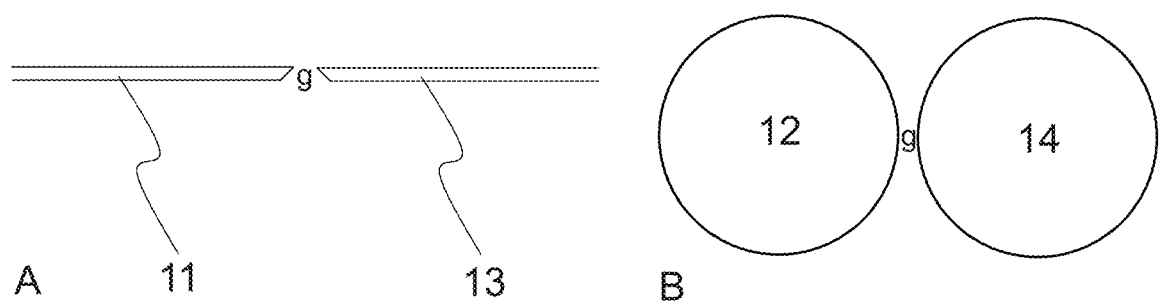
FIG. 19 shows examples of limiting parts forming the gap g.

A gap g is formed between two parallel objects, such as limiting parts, which may be for example rollers, plates, blades, or the like, or combination thereof. The objects usually have a straight edge or surface, which takes part in forming the gap. In one embodiment the method comprises passing the immersed non-woven fabric through a prefined gap between a pair of rollers, between a roller and a blade, between a roller and a plate, between a blade and a plate, between a pair or plates or between a pair of blades to define the thickness of the coating on the immersed nonwoven fabric. A roller may be movable or fixed, and a pair of rollers may include one movable roller and one fixed roller, or both rollers may be of the same type. The width of the gap refers to the shortest distance of the surfaces of the limiting parts, such as two blades 11, 13, or two rollers 12, 14, as shown in FIGS. 19A and B. The gap g has such a width that the immersed nonwoven is not pressed in such way that the coating and/or uneven impregnation would be disturbed. The limiting parts, such as plates and/or blades, may be positioned to minimize the pressure directed to the immersed nonwoven, for example they may be placed perpendicularly or at angle in respect of each other or other limiting part(s). Two limiting parts having a flat or blade-like structure, may be placed at an angle in respect of each other, such as an angle in the range of 45–180°, such as 60-180°, 45-90° or 90-180°. This enables specifically cutting away or peeling a part of the surface layer when the immersed nonwoven passes through the gap. The gap may be arranged to cut a part of the NFC dispersion or hydrogel present on the nonwoven, especially to obtain a desired thickness of the immersed nonwoven and/or the coating layer.

The gap width may depend on the thickness of the nonwoven, especially when the nonwoven is stretched out in the process. The gap width may be adjustable, and the method may include adjusting the gap width, preferably according to the selected nonwoven, according to the immersing degree and/or used immersing dispersion, and/or according to the desired final product, for example according to the desired thickness of the coating layer. In one example the limiting parts do not include a roller.

Defining the thickness of the immersed nonwoven fabric or the coating on the nonwoven fabric may refer to removing excess nanofibrillar cellulose dispersion or hydrogel, especially from the surface of the immersed nonwoven fabric, to obtain a desired thickness of the immersed nonwoven fabric. Defining the thickness may comprise defining the thickness of the coating layer on the surface of the immerser nonwoven fabric, preferably to obtain a desired thickness of the coating layer comprising or consisting of nanofibrillar cellulose dispersion or hydrogel.

The thickness of the immersed nonwoven fabric, as defined by the gap, may be a lower thickness than the thickness of the immersed nonwoven fabric before the gap. The defined thickness may be equal or higher than the thickness of the nonwoven, such as the thickness of the nonwoven as stretched and/or immersed.

The prefined gap may have a width equal or higher than the thickness of the nonwoven, such as the thickness of the nonwoven as stretched and/or immersed. The gap may have a width of 0-0.5 mm higher than said thickness of the nonwoven, such as 0.05-0.1 mm higher, 0.05-0.05 mm higher, or 0.05-0.01 mm higher than the thickness of the nonwoven. In some examples the gap has a width in the range of 0.01-1.0 mm, such as 0.1-0.5 mm, 0.15-0.5 mm, or 0.2-0.3 mm. This however depends on the thickness of the nonwoven fabric, the properties of the NFC dispersion and/or hydrogel, and other method features. The thickness, as well as grammage and/or other properties, of the remaining coating layer can be controlled by selecting a suitable gap, and/or by adjusting the width of the gap. The method may comprise providing a width of the gap and/or adjusting the width of the gap, for example before inserting the immersed nonwoven to the gap, and/or between immersing runs or passes.

The thickness of the coating layer, after passing the gap, may be at least 5 µm or at least 10 µm, such as at least 20 µm, at least 30 µm, at least 40 µm or at least 50 µm. This may refer to the medical product before dewatering or after dewatering. However the thickness of the coating may depend on the number of passes through the immersing run, and the thickness may therefore vary during the process.

The method may comprise passing the immersed nonwoven through a gap g between a pair of rollers 12, 14, which may be also called rolls. This step may be called rolling. The gap width may be adjusted, for example wherein one or both of the rollers 12, 14 is movable in relation to the other roller, so that a roller can be moved to a desired distance from the other roller, and fixed to that position or distance to obtain the desired distance and width of the gap. A similar gap may be arranged between other structures, such as one roll and a blade or the like, or between two blades, two plates or the like. Similarly, a blade or other limiting part may be movable in relation to the other limiting part.

Figure 20:
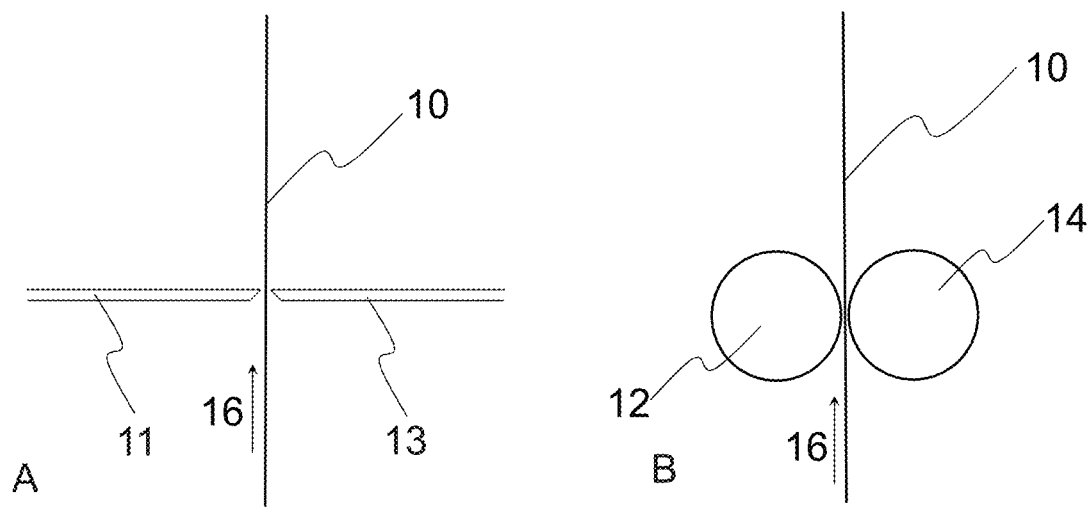
FIG. 20 shows examples wherein the immersed nonwoven passes through A) two blades and B) though two rollers.

The rollers may comprise nip rollers. A nip in general refers to the contact area where two opposing rolls meet, such as in a calender. Nip rolls or pinch rolls may be powered rolls and they are usually used to press two or more sheets together to form a laminated product. In one example one roll is powered and the other one is freely movable. Nip rolls are sometimes called pinch rolls or wringers. The nip rolls may be overlapping and one roll may be freely movable. The nip rolls may be for example steel rolls, which may have fine grooving. Using nip rolls was found very effective for removing excess dispersion from the nonwoven. Nip rolls are very useful in an industrial scale process, wherein a long nonwoven sheet is fed immediately from immersion to the nip rolls and further to a next step, such as to a dewatering step. FIG. 20A shows how a nonwoven 10 passes between two blades 11, 13, and FIG. 20B shows as it passes through two rollers 12, 14 rolling in directions 18, 19 which follow the direction 16 the nonwoven is proceeding. In the present method it is desired that the rollers do not cause squeezing of the immersed fabric, i.e. the rollers do not substantially press the immersed fabric. This is obtained by selecting such a width of the gap that allows defining the thickness but does not compress the nanofibrillar cellulose or press or force it into the nonwoven. The same applies to any limiting parts which may be used for forming the gap.

In the method steps the nonwoven is moved through the steps, such as immersing step, the gap and/or the dewatering preferably by using drive rolls or other means arranged to drive or move the nonwoven. Such means may be connected to an actuator for moving the means, and the speed thereof may be adjustable.

The method comprises dewatering the impregnated nonwoven, especially the impregnated nonwoven having passed through the gap, and therefore having a defined thickness and/or defined thickness of the coating and/or defined structure, which is obtained in the previous preparation step(s). Dewatering fixes the structure obtained and preserved in the previous method steps. It was found out that dewatering by evaporating only may be sufficient for the present products. Dewatering by evaporating, such as by using a source of heat, helps preserving and maintaining the coating and the unevenly impregnated structure of the nonwoven, especially on the both sides of the nonwoven, and results in efficient and adequate dewatering. On the contrary, dewatering methods deforming the formed structure, such as methods involving vacuum, especially vacuum forming suction though the nonwoven, and/or high pressure, could destroy the structure. Therefore preferably the dewatering does not involve vacuum and/or pressing, for example pressing through a filter or pressing with very high pressure, which could deform the nonwoven or the coating. When using such preserving dewatering method it was possible to obtain a coating on the nonwoven, which contained a dense but porous network of nanofibrillar cellulose, which provided desired permeability for air and liquids as well as for bioactive and other molecules.

In one embodiment the dewatering is carried out by evaporating. The dewatering may be carried out by using non-contact drying, such as with an infrared dryer, floating dryer, or impingement dryer. Air impingement drying involves blowing hot air (such as at 300° C.) in gas burners at high velocity against the wet sheet.

In some cases dewatering may be carried out by using contact drying, such as with a press dryer, cylinder dryer (drying cylinder) or belt dryer. This may be carried out after another dewatering step, such as an evaporating step, or as the only dewatering step. When drying cylinder is used the surface of the product will be smooth and the drying is cost efficient. In belt drying, the product is dried in a drying chamber by contact with a continuous hot steel band which is heated either by steam or hot gas. The water from the band is evaporated due to the heat from the band. In such contact drying a coating on one side may be affected, but the coating on the opposite side may remain unpressed. Therefore contact drying methods may be useful for preparing products which have unpressed NFC coating only on one side of the nonwoven.

After dewatering a final product may be obtained containing a coating on the nonwoven fabric and preferably an impregnation of the nonwoven fabric with the NFC with decreasing concentration from the surface towards the center of the fabric. Alternatively an intermediate product may be obtained, which may be subjected again to the immersing treatment discussed herein, and passed through a gap. This may be repeated until a desired product is obtained.

The thickness of the coating layer on top of the nonwoven, i.e. outside the nonwoven, in the intermediate or in the final product, may be at least 5 µm, at least 10 µm, at least 20 µm, at least 30 µm, at least 40 µm or at least 50 µm, such as 5-200 µm, 5-100 µm, 5-50 µm, 10-200 µm, 10-100 µm or 10-50 µm, for example. This may however depend on the thickness of the nonwoven fabric.

In dewatering the dry matter content of the nonwoven is increased, for example to at least 50% (w/w), to at least 70% (w/w), to at least 80% (w/w), or to at least 90% (w/w), for example to the range of 90-100% (w/w), such as 90-99% (w/w). The dry matter content of the coating may be increased to said ranges as well.

The thickness, density and/or structure of the unpressed and unvacuumed NFC coating even after dewatering are maintained at such level that desired properties, such as absorption capacity, fluid retention, moisture vapor transmission rate, permeability and the like properties and functionalities as discussed herein, are obtained. However, the thickness of the coating layer and probably the whole immersed nonwoven may decrease during dewatering. The obtained NFC coating was also found out to provide enhanced wound healing properties, as discussed herein and demonstrated in the examples. In dewatering the intermediate coating is formed into a final coating, which has a final thickness or a third thickness, or other final properties.

After dewatering the products may be cut into desired sizes and packed, preferably into sterile packages. The packings may be sealed, preferably with gas and/or water proof sealing(s). The product or the cut pieces may be sterilized before packing and/or sealing the package. The moisture content of the product may be adjusted into a desired level before packing and/or sealing the package. Any additive(s) may be added also at this point.

The method may be carried out as a batch process or as a continuous process. It was found out that the present method is well suitable to be run as a continuous process, as the means for immersing, means for defining the thickness of the coating and means for dewatering, especially by evaporating, can be arranged in series and the nonwoven may be run in a system setup comprising these means at a relatively high speed. This enhances the productivity of the method and saves time and money. Also uniform products can be obtained from such process. In one example the immersing, passing through the gap, and preferably also the dewatering are carried out as a continuous process. However the total process may include continuous parts as batch and/or manual operations, for example if the nonwoven is to be subjected to certain operations repeatedly, for example if the immersing and/or passing through the gap are repeated. The method may include detecting and/or measuring one or more features of the product, such as the thickness of the coating or the nonwoven and/or any feature indirectly characterizing the thickness of the coating or the nonwoven, or other feature discussed herein. For example visual, photometric, acoustic, mechanical and/or other means for detecting such features may be used, such as sensor(s), probe(s), source(s) of sound or light, and the like.

The method may be carried out with a suitable device setup comprising a source of nanofibrillar cellulose, such as a container, especially an open container allowing the handling of the nonwoven sheet, one or more guiding means, such as roller(s), which may be placed in the source of nanofibrillar cellulose and/or at the path of the treated nonwoven, means for providing the gap, such as the limiting parts, which may be provided with means for adjusting the limiting parts to define the gap g, and one or more means for dewatering the treated nonwoven. The guiding means may comprise one or more moving means, such as means coupled to an actuator for moving the means, for example a roller, for moving the nonwoven fabric in the device setup. For example one or more rollers may be coupled to an electric motor for rotating the roller. The device setup may be fully or partly automatized.

Figure 21:
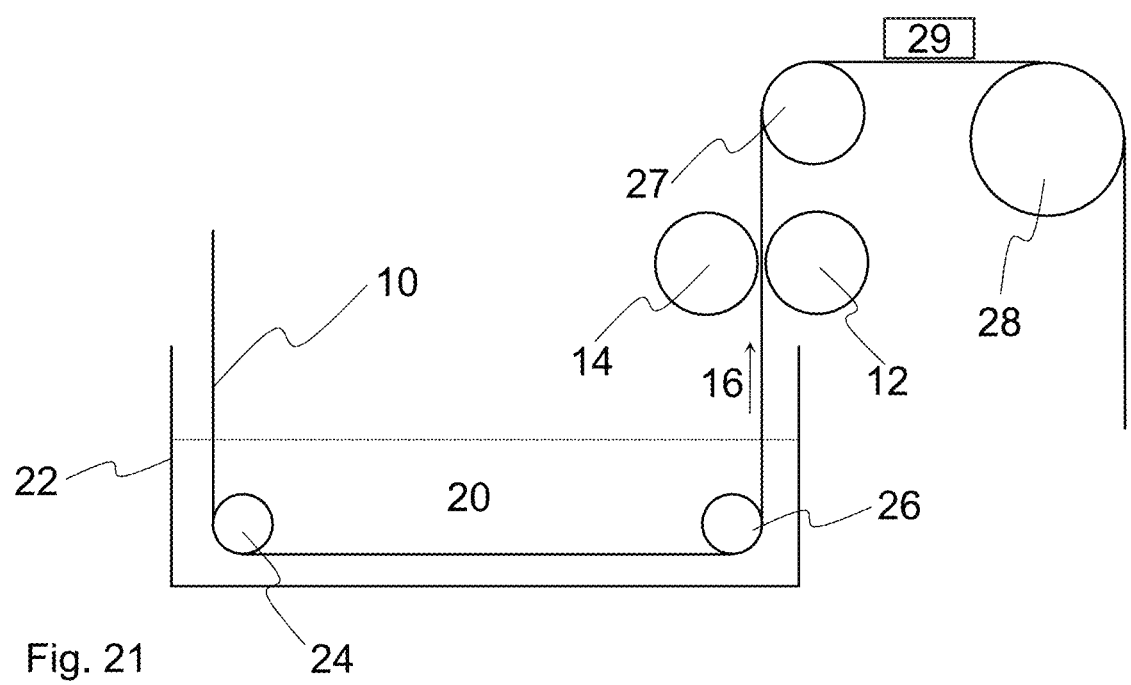
FIG. 21 shows an example of an arrangement having an immersion reservoir, a pair of nip rollers and a cylinder dryer and/or a non-contact dryer.

FIG. 21 shows an example of a continuous process, wherein a nonwoven 10 is first immersed in a container 22 with NFC dispersion 20. The nonwoven 10 is moved or guided by using one or more rolling rolls 24, 26 and the nonwoven moves forward in the direction 16 leading to a pair of rollers 12, 14 defining the gap g. One roller 14 may be a stationary, i.e. a fixed or non-moving roll, and the other one may be a turning roll. After this the nonwoven moves via a guiding roll 27 onto a cylinder dryer 28, which may be a turning roll, wherein water is evaporated from the nonwoven, and/or via a non-contacting dryer 29, which may be a source of heat, such as a source of infra red, and finally a dewatered product is obtained. At least one side of the nonwoven will then have an unpressed coating. It is also possible to repeat the treatment for dewatered nonwoven or for nonwoven which passed through the rollers but is not dewatered. In another example the roller 14 could be replaced with a blade 11. The setup of FIG. 21 may be modified with one or more features described herein, such as parts or devices, for example by deleting and/or replacing any features presented, and/or by adding any other features(s).

The immersing, the passing though the gap and the dewatering, or the immersing and the passing though the gap, may be carried out once or the steps may be repeated if necessary to maximize saturation and/or to obtain desired distribution of the dispersion on and in the nonwoven. It is also possible to adjust the grammage and/or other suitable properties of the formed product, especially the NFC coating and/or impregnation of the product. The steps of immersing, passing though the gap and optionally dewatering together may be called for example as "a pass", an immersing run or a coating run. A specific property, such as a grammage of the product or a thickness or a grammage of the coating, may be desired. In such case the immersing run is repeated until the medical product has reached the desired grammage or coating. Therefore in one example the steps, a pass or a run are/is repeated at least once, i.e. the immersing, passing though the gap and optionally dewatering are carried out at least twice. In one embodiment the steps or passes are carried out for 1-10 times, such as 1-6 times, 2-8 times or 2-4 times, for example 1, 2, 3, 4, 5 or 6 times, or more. In one example the steps are repeated until the medical product has reached a grammage in the range of 30-70 g/m$^2$, such as 50-60 g/m$^2$, or until the NFC coating layer has a grammage in the range of 0.1-60 g/m$^2$, such as 3-40 g/m$^2$, or 5-20 g/m$^2$, or until any other grammage and/or other feature disclosed herein is obtained. The grammage of the coating can be determined from the product when the grammage of the nonwoven is known. If these steps are repeated, different initial and/or intermediate coatings are obtained, such as a first, a second and optionally a third initial or intermediate coating. In general the amount of NFC, which may be characterized by grammage, is controlled with the gap, NFC hydrogel concentration and number of passes. A person skilled in the art can determine these features without conducting undue experiments.

In one embodiment the medical product comprises a nonwoven impregnated with nanofibrillar cellulose. Preferably the content of the nanofibrillar cellulose decreases from the surfaces of the nonwoven towards the middle of the nonwoven between the surfaces. Such product may be obtained with the method disclosed herein.

In one example the medical product has a grammage in the range of 30-70 g/m$^2$, such as in the range of 35-65 g/m$^2$, such as in the range of 45-65 g/m$^2$. In one embodiment, which was found especially preferred in the tests, the medical product has a grammage in the range of 50-60 g/m$^2$. In one example the medical product has a grammage, especially when sterilized, in the range of 50-55 g/m$^2$.

The grammage of the nanofibrillar cellulose in the medical product may be in the range of 1-60 g/m$^2$, for example 1-40 g/m$^2$, such as 3-40 g/m$^2$, 2-20 g/m$^2$, 2-12 g/m$^2$, 5-20 g/m$^2$ or 5-15 g/m$^2$, measured as dry weight of the product.

In one embodiment the medical product has a thickness, such as a bulking thickness, in the range of 200-260 µm, such as in the range of 200-230 especially when anionic NFC is used.

In one example the medical product has a density in the range of 200-700 g/cm$^3$, such as 200-530 kg/m$^3$. The density may be measured as apparent bulking density by ISO 534. In one embodiment the apparent bulk density of the medical product is in the range of 200-260 kg/m$^3$. In one embodiment the apparent bulk density of the medical product is in the range of 220-260 kg/m$^3$.

In one example the medical product has a bulk in the range of 3.9-4.6 cm$^3$/g, such as 3.9-4.3 cm$^3$/g.

In one embodiment the medical product has an absorption capacity in the range of 1.5-2.1 g/100 cm$^2$, such as in the range of 1.8-2.1 g/100 cm$^2$ or in the range of 1.5-1.8 g/100 cm$^2$.

In one example the medical product has an area change when wetted in the range of 1.9-2.5%, such as in the range of 2-2.4% or 2.0-2.2%.

In one example the medical product has an area change when dried in the range of −3-0%, such as in the range of −2.8-0%, for example in the range of −2.8--0.4%. When anionic NFC was used the area change when dried was very low or zero, such as in the range of −0.2-0, or about 0.

In one embodiment the medical product has a fluid retention in the range of 14.5-40%, such as 14.5-30%, 20-30%, or 22-30%. Medical products comprising anionic NFC has a fluid retention at a higher level, such as in the range of 22-30% or 25-30%. The high fluid retention enables keeping the dressing moist long enough allowing biomolecules to mobilise on the surface and inside the dressing.

In one embodiment the medical product has a moisture vapor transmission rate (MVTR) in the range of 4000-5500 g/m$^2$*24 h, measured by SFS-EN-13726-2, such as in the range of 4000-5000 g/m$^2$*24 h, or 4400-5000 g/m$^2$*24 h.

The air permeance of the medical product, preferably as autoclaved, may be less than 120 ml/min, or less than 650 ml/min, such as less than 1000 ml/min or less than 2100 ml/min. However in some example the air permeance may be even higher, such as less than 5100 ml/min. The air permeance correlates in general with the amount of nanofibrillar cellulose. The higher the amount of nanofibrillar cellulose, the lower the air permeance. With an exemplary air permeance of less than 600 ml/min, or less than 500 ml/min the amount of nanocellulose is at suitable level for many applications.

In one embodiment the medical product comprises bioactive agent(s) and/or therapeutic agent(s). The bioactive agent(s) and/or therapeutic agent(s) may be added to the medical product, such as the therapeutic agents disclosed herein or other active agents, or the bioactive agent may be diffused to the medical product during the use, i.e. when the medical product is applied onto a skin, wound or other target.

A bioactive agent, which may be also called bioactive molecules and compounds, as used herein, refers to molecules or other substances which may take part or have an effect in biological reactions or processes, or agents which may show biological activity. Such agents include biological molecules such as proteins, lipids, nucleic acids, enzymes, hormones, growth factors and other factors, signalling molecules, antibodies, activators, inhibitors, cell organelles, and the like, which may be of biological origin, for example derived or obtained from tissue, i.e. they may be natural (non-synthetic) molecules. Bioactive agents may also include synthetic molecules, such as pharmaceuticals or other molecules. A therapeutic agent may be a pharmaceutical agent, i.e. a drug, but it also may be a bioactive agent. A therapeutic agent aims to provide a therapeutic effect towards a disease or disorder. A therapeutic agent, especially when synthetic, may be isolated and may be therefore provided as a pure substance. The bioactive agents, as discussed herein, may on the other hand be directly obtained from a tissue and the exact content of such bioactive material may not always be known. It is however possible to provide bioactive agents in isolated and/or purified form as well.

In one embodiment the medical product has a moisture content in the range of 0-10%. However it is probably not easy or even necessary to obtain a completely dry product, so the product may contain at least a small amount of water. The moisture content may be in the range of 1-10% (w/w), such as in the range of 5-10% (w/w), which moisture contents may be suitable for using, handling and/or storing the product, for example to maintain the specific structure of the product. In many cases the moisture content may correspond to the ambient moisture content, which may be in the range of 5-7%.

In one embodiment the medical product is packed in a sealed package, preferably in the form of a medical dressing or a patch. The medical product may be packed in a separate packing. Separate packings may be provided as a series of packings. Usually such packed products are provided as sterilized. A sealed packing may comprise a sealed bag or the like packing, for example made of plastic, paper, composite materials and/or combinations thereof, which may contain a tearable part. Prior to use the treatable part is teared to expose the medical product, which is preferably in sterile form and may have a desired water content.

One embodiment provides a kit comprising the medical product or the cosmetic product described herein, for example a packed product, wherein the kit may contain one or more of the packed products. The kit may also contain other materials or equipment, such as a container containing saline solution or the like for pretreating the product(s) prior to use.

Nanofibrillar Cellulose

The starting material for preparing the medical products is nanofibrillar cellulose, also called as nanocellulose, which refers to isolated cellulose fibrils or fibril bundles derived from cellulose raw material. Nanofibrillar cellulose is based on a natural polymer that is abundant in nature. Nanofibrillar cellulose has a capability of forming viscous hydrogel in water. Nanofibrillar cellulose production techniques may be based on disintegrating fibrous raw material, such as grinding of aqueous dispersion of pulp fibers to obtain nanofibrillated cellulose. After the grinding or homogenization process, the obtained nanofibrillar cellulose material is a dilute viscoelastic hydrogel.

The obtained material usually exists at a relatively low concentration homogeneously distributed in water due to the disintegration conditions. The starting material may be an aqueous gel at a concentration of 0.2-10% (w/w), for example 0.2-5% (w/w). The nanofibrillar cellulose may be obtained directly from the disintegration of fibrous raw material. An example of commercially available nanofibrillar cellulose hydrogel is GrowDex® by UPM.

Because of its nanoscale structure nanofibrillar cellulose has unique properties which enable functionalities which cannot be provided by conventional cellulose. However, because of the nanoscale structure nanofibrillar cellulose is also a challenging material. For example dewatering or handling of nanofibrillar cellulose may be difficult.

The nanofibrillar cellulose may be prepared from cellulose raw material of plant origin, or it may also be derived from certain bacterial fermentation processes. The nanofibrillar cellulose is preferably made of plant material. The raw material may be based on any plant material that contains cellulose. In one example the fibrils are obtained from non-parenchymal plant material. In such case the fibrils may be obtained from secondary cell walls. One abundant source of such cellulose fibrils is wood fibres. The nanofibrillar cellulose may be manufactured by homogenizing wood-derived fibrous raw material, which may be chemical pulp and/or bleached pulp. Cellulose fibers are disintegrated to produce fibrils which have an average diameter of only some nanometers, which may be 200 nm or less in most cases, and gives a dispersion of fibrils in water. The fibrils originating from secondary cell walls are essentially crystalline with degree of crystallinity of at least 55%. Such fibrils may have different properties than fibrils originated from primary cell walls, for example the dewatering of fibrils originating from secondary cell walls may be more challenging. In general in the cellulose sources from primary cell walls, such as sugar beet, potato tuber and banana rachis, the microfibrils are easier to liberate from the fibre matrix than fibrils from wood, and the disintegration requires less energy. However, these materials are still somewhat heterogeneous and consist of large fibril bundles.

Non-wood material may be from agricultural residues, grasses or other plant substances such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed. The cellulose raw material could be also derived from the cellulose-producing micro-organism. The micro-organisms can be of the genus *Acetobacter, Agrobacterium, Rhizobium, Pseudomonasor Alcaligenes*, preferably of the genus *Acetobacter* and more preferably of the species *Acetobacter xylinumor* or *Acetobacter pasteurianus*.

It was found out that nanofibrillar cellulose obtained from wood cellulose is preferable for medical or scientific products described herein. Wood cellulose is available in large amounts, and the preparation methods developed for wood cellulose enable producing nanofibrillar materials suitable for the products. The nanofibrillar cellulose obtained by fibrillating plant fibers, especially wood fibers, differs structurally from nanofibrillar cellulose obtained from microbes, and it has different properties. For example compared to bacterial cellulose, nanofibrillated wood cellulose is homogenous and more porous and loose material, which is advantageous in applications involving living tissue. Bacterial cellulose is usually used as such without similar fibrillation as in plant cellulose, so the material is different also in this respect. Bacterial cellulose is dense material which easily forms small spheroids and therefore the structure of the material is discontinuous, and it is not desired to use such material in the applications relating to living tissue, especially when homogeneity of the material is required.

Wood may be from softwood tree such as spruce, pine, fir, larch, douglas-fir or hemlock, or from hardwood tree such as birch, aspen, poplar, alder, eucalyptus, oak, beech or acacia, or from a mixture of softwoods and hardwoods. In one example the nanofibrillar cellulose is obtained from wood pulp. The wood pulp may be bleached pulp. The nanofibrillar cellulose may be obtained from hardwood pulp. In one example the hardwood is birch. The nanofibrillar cellulose may be obtained from softwood pulp. In one example said wood pulp is chemical pulp. Chemical pulp may be desired for the products disclosed herein. Chemical pulp is pure material and may be used in a wide variety of applications. For example chemical pulp lack the pitch and resin acids present in mechanical pulp, and it is more sterile or easily sterilisable. Further, chemical pulp is more flexible and provides advantageous properties for example in medical and scientific materials. For example very homogenous nanofibrillar cellulose materials may be prepared without excess processing or need for specific equipment or laborious process steps. In one example the pulp is bleached birch pulp.

Nanofibrillar cellulose, including the cellulose fibrils and/or fibril bundles, is characterized by a high aspect ratio (length/diameter). The average length of nanofibrillar cellulose (the median length of particles such as fibrils or fibril bundles) may exceed 1 µm, and in most cases it is 50 µm or less. If the elementary fibrils are not completely separated from each other, the entangled fibrils may have an average total length for example in the range of 1-100 µm, 1-50 µm, or 1-20 µm. However, if the nanofibrillar material is highly fibrillated, the elementary fibrils may be completely or almost completely separated and the average fibril length is shorter, such as in the range of 1-10 µm or 1-5 µm. This applies especially for native grades of fibrils which are not shortened or digested, for example chemically, enzymatically or mechanically. However, strongly derivatized nanofibrillar cellulose may have a shorter average fibril length, such as in the range of 0.3-50 µm, such as 0.3-20 µm, for example 0.5-10 µm or 1-10 µm. Especially shortened fibrils, such as enzymatically or chemically digested fibrils, or mechanically treated material, may have an average fibril length of less than 1 µm, such as 0.1-1 µm, 0.2-0.8 µm or 0.4-0.6 µm. The fibril length and/or diameter may be estimated microscopically, for example using CRYO-TEM, SEM or AFM images.

The average diameter (width) of nanofibrillar cellulose is less than 1 µm, or 500 nm or less, such as in the range of 1-500 nm, but preferably 200 nm or less, even 100 nm or less or 50 nm or less, such as in the range of 1-200 nm, 2-200 nm, 2-100 nm, or 2-50 nm, even 2-20 for highly fibrillated material. The diameters disclosed herein may refer to fibrils and/or fibril bundles. The smallest fibrils are in the scale of elementary fibrils, the average diameter being typically in the range of 2-12 nm. The dimensions and size distribution of the fibrils depend on the refining method and efficiency. In case of highly refined native nanofibrillar cellulose, the average fibril diameter, including fibril bundles, may be in the range of 1-200 nm or 1-100 nm, for example in the range of 2-100 nm, 1-50 nm or 10-50 nm. Nanofibrillar cellulose is characterized by a large specific surface area and a strong ability to form hydrogen bonds. In water dispersion, the nanofibrillar cellulose typically appears as either light or turbid gel-like material. Depending on the fiber raw material, nanofibrillar cellulose obtained from plants, especially wood, may also contain small amounts of other plant components, especially wood components, such as hemicellulose or lignin. The amount is dependent on the plant source.

In general cellulose nanomaterials may be divided into categories according to TAPPI W13021, which provides standard terms for cellulose nanomaterials. Not all of these materials are nanofibrillar cellulose. Two main categories are "Nano objects" and "Nano structured materials". Nano-structured materials include "Cellulose microcrystals" (sometimes called as CMC) having a diameter of 10-12 µm and length:diameter ratio (L/D)<2, and "Cellulose microfibrils" having a diameter of 10-100 nm and a length of 0.5-50 µm. Nano objects include "Cellulose nanofibers", which can be divided into "Cellulose nanocrystals" (CNC) having a diameter of 3-10 nm and L/D>5, and "Cellulose nanofibrils" (CNF or NFC), having a diameter of 5-30 nm and L/D>50.

Different grades of nanofibrillar cellulose may be categorized based on three main properties: (i) size distribution, length and diameter (ii) chemical composition, and (iii) rheological properties. These properties may not be fully dependent on each other. To fully describe a grade, the properties may be used in parallel. Examples of different grades include native (or chemically unmodified) NFC, oxidized NFC (high viscosity), oxidized NFC (low viscosity), carboxymethylated NFC and cationized NFC. Within these main grades, also sub-grades exist, for example: extremely well fibrillated vs. moderately fibrillated, high degree of substitution vs. low degree of substitution, low viscosity vs. high viscosity etc. The fibrillation technique and the chemical pre-modification have an influence on the fibril size distribution. Typically, non-ionic grades have wider average fibril diameter (for example in the range of 10-100 nm, or 10-50 nm) while the chemically modified grades are a lot thinner (for example in the range of 2-20 nm). Distribution is also narrower for the modified grades. Certain modifications, especially TEMPO-oxidation, yield shorter fibrils.

Depending on the raw material source, e.g. hardwood vs. softwood pulp, different polysaccharide composition exists in the final nanofibrillar cellulose product. Commonly, the non-ionic grades are prepared from bleached birch pulp, which yields high xylene content (25% by weight). Modified grades are prepared either from hardwood or softwood pulps. In those modified grades, the hemicelluloses are also modified together with the cellulose domain. Most probably, the modification is not homogeneous, i.e. some parts are more modified than others. Thus, detailed chemical analysis is usually not possible as the modified products are complicated mixtures of different polysaccharide structures.

In an aqueous environment, a dispersion of cellulose nanofibers forms a viscoelastic hydrogel network. The gel is formed already at relatively low concentrations of for example 0.05-0.2% (w/w) by dispersed and hydrated entangled fibrils. The viscoelasticity of the NFC hydrogel may be characterized for example with dynamic oscillatory rheological measurements.

The nanofibrillar cellulose hydrogels exhibit characteristic rheological properties. A dispersion of nanofibrillar cellulose is a non-Newtonian fluid, which does not follow Newton's law of viscosity, i.e. constant viscosity independent of stress. The dispersion of nanofibrillar cellulose exhibit shear-thinning properties, which means that the viscosity depends on the speed (or force) by which the material is deformed. This is a special case of thixotropic behavior, which is time-dependent shear thinning property, wherein it takes a finite time to attain equilibrium viscosity when introduced to a steep change in shear rate. More particularly a dispersion of nanofibrillar cellulose is a pseudoplastic fluid, which returns to gel state almost instantly when the shear stress is removed. Conventional Newtonian materials do not exhibit such behavior, such as conventional cellulose, so teachings related to such Newtonian materials cannot be usually applied to nanofibrillar cellulose.

When measuring the viscosity in a rotational rheometer, the shear-thinning behavior is seen as a decrease in viscosity with increasing shear rate. The hydrogels show plastic behavior, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity is seen after exceeding the critical shear stress. The zero shear viscosity and the yield stress are the most important rheological parameters to describe the suspending power of the materials. These two parameters separate the different grades quite clearly and thus enable classification of the grades.

The dimensions of the fibrils or fibril bundles are dependent for example on the raw material, the disintegration method and number of disintegration runs. Mechanical disintegration of the cellulose raw material may be carried out with any suitable equipment such as a refiner, grinder, disperser, homogenizer, colloider, friction grinder, pin mill, rotor-rotor dispergator, ultrasound sonicator, fluidizer such as microfluidizer, microfluidizer or fluidizer-type homogenizer. The disintegration treatment is performed at conditions wherein water is sufficiently present to prevent the formation of bonds between the fibers.

In one example the disintegration is carried out by using a disperser having at least one rotor, blade or similar moving mechanical member, such as a rotor-rotor dispergator, which has at least two rotors. In a disperser the fiber material in dispersion is repeatedly impacted by blades or ribs of rotors striking it from opposite directions when the blades rotate at the rotating speed and at the peripheral speed determined by the radius (distance to the rotation axis) in opposite directions. Because the fiber material is transferred outwards in the radial direction, it crashes onto the wide surfaces of the blades, i.e. ribs, coming one after the other at a high peripheral speed from opposite directions; in other words, it receives a plurality of successive impacts from opposite directions. Also, at the edges of the wide surfaces of the blades, i.e. ribs, which edges form a blade gap with the opposite edge of the next rotor blade, shear forces occur, which contribute to the disintegration of the fibers and detachment of fibrils. The impact frequency is determined by the rotation speed of the rotors, the number of the rotors, the number of blades in each rotor, and the flow rate of the dispersion through the device.

In a rotor-rotor dispergator the fiber material is introduced through counter-rotating rotors, outwards in the radial direction with respect to the axis of rotation of the rotors in such a way that the material is repeatedly subjected to shear and impact forces by the effect of the different counter-rotating rotors, whereby it is simultaneously fibrillated. One example of a rotor-rotor dispergator is an Atrex device.

Another example of a device suitable for disintegrating is a pin mill, such as a multi-peripheral pin mill. One example of such device includes a housing and in it a first rotor equipped with collision surfaces; a second rotor concentric with the first rotor and equipped with collision surfaces, the second rotor being arranged to rotate in a direction opposite to the first rotor; or a stator concentric with the first rotor and equipped with collision surfaces. The device includes a feed orifice in the housing and opening to the center of the rotors or the rotor and stator, and a discharge orifice on the housing wall and opening to the periphery of the outermost rotor or stator.

In one example the disintegrating is carried out by using a homogenizer. In a homogenizer the fiber material is subjected to homogenization by an effect of pressure. The homogenization of the fiber material dispersion to nanofibrillar cellulose is caused by forced through-flow of the dispersion, which disintegrates the material to fibrils. The fiber material dispersion is passed at a given pressure through a narrow through-flow gap where an increase in the linear velocity of the dispersion causes shearing and impact forces on the dispersion, resulting in the removal of fibrils from the fiber material. The fiber fragments are disintegrated into fibrils in the fibrillating step.

As used herein, the term "fibrillation" generally refers to disintegrating fiber material mechanically by work applied to the particles, where cellulose fibrils are detached from the fibers or fiber fragments. The work may be based on various effects, like grinding, crushing or shearing, or a combination of these, or another corresponding action that reduces the particle size. The expressions "disintegration" or "disintegration treatment" may be used interchangeably with "fibrillation".

The fiber material dispersion that is subjected to fibrillation is a mixture of fiber material and water, also herein called "pulp". The fiber material dispersion may refer generally to whole fibers, parts (fragments) separated from them, fibril bundles, or fibrils mixed with water, and typically the aqueous fiber material dispersion is a mixture of such elements, in which the ratios between the components are dependent on the degree of processing or on the treatment stage, for example number of runs or "passes" through the treatment of the same batch of fiber material.

One way to characterize the nanofibrillar cellulose is to use the viscosity of an aqueous solution containing said nanofibrillar cellulose. The viscosity may be for example Brookfield viscosity or zero shear viscosity. The specific viscosity, as described herein, distinguishes nanofibrillar cellulose from non-nanofibrillar cellulose.

In one example the apparent viscosity of the nanofibrillar cellulose is measured with a Brookfield viscometer (Brookfield viscosity) or another corresponding apparatus. Suitably a vane spindle (number 73) is used. There are several commercial Brookfield viscometers available for measuring apparent viscosity, which all are based on the same principle. Suitably RVDV spring (Brookfield RVDV-III) is used in the apparatus. A sample of the nanofibrillar cellulose is diluted to a concentration of 0.8% by weight in water and mixed for 10 min. The diluted sample mass is added to a 250 ml beaker and the temperature is adjusted to 20° C.±1° C., heated if necessary and mixed. A low rotational speed 10 rpm is used. In general Brookfield viscosity may be measured at 20° C.±1° C., at a consistency of 0.8% (w/w) and at 10 rpm.

The nanofibrillar cellulose, for example provided as a starting material in the method, may be characterized by the viscosity it provides in a water solution. The viscosity describes, for example, the fibrillation degree of the nanofibrillar cellulose. In one example the nanofibrillar cellulose when dispersed in water provides a Brookfield viscosity of at least 2000 mPa·s, such as at least 3000 mPa·s, measured at 20° C.±1° C., at a consistency of 0.8% (w/w) and at 10 rpm. In one example the nanofibrillar cellulose, when dispersed in water, provides a Brookfield viscosity of at least 10000 mPa·s measured at 20° C.±1° C., at a consistency of 0.8% (w/w) and at 10 rpm. In one example the nanofibrillar cellulose, when dispersed in water, provides a Brookfield viscosity of at least 15000 mPa·s measured at 20° C.±1° C., at a consistency of 0.8% (w/w) and at 10 rpm. Examples of Brookfield viscosity ranges of said nanofibrillar cellulose when dispersed in water include 2000-20000 mPa·s, 3000-20000 mPa·s, 10000-20000 mPa·s, 15000-20000 mPa·s, 2000-25000 mPa·s, 3000-25000 mPa·s, 10000-25000 mPa·s, 15000-25000 mPa·s, 2000-30000 mPa·s, 3000-30000 mPa·s, 10000-30000 mPa·s, and 15000-30000 mPa·s, measured at 20° C.±1° C., at a consistency of 0.8% (w/w) and at 10 rpm.

The nanofibrillar cellulose may also be characterized by the average diameter (or width), or by the average diameter together with the viscosity, such as Brookfield viscosity or zero shear viscosity. In one example nanofibrillar cellulose suitable for use in the products described herein has an average fibril diameter in the range of 1-200 nm, or 1-100 nm. In one example said nanofibrillar cellulose has an average fibril diameter in the range of 1-50 nm, such as 2-20 nm or 5-30 nm. In one example said nanofibrillar cellulose has an average fibril diameter in the range of 2-15 nm, such as in the case of TEMPO oxidized nanofibrillar cellulose.

The diameter of a fibril may be determined with several techniques, such as by microscopy. Fibril thickness and width distribution may be measured by image analysis of the images from a field emission scanning electron microscope (FE-SEM), a transmission electron microscope (TEM), such as a cryogenic transmission electron microscope (cryo-TEM), or an atomic force microscope (AFM). In general AFM and TEM suit best for nanofibrillar cellulose grades with narrow fibril diameter distribution.

A rheometer viscosity of the nanofibrillar cellulose dispersion may be measured according to one example at 22° C. with a stress controlled rotational rheometer (AR-G2, TA Instruments, UK) equipped with a narrow gap vane geometry (diameter 28 mm, length 42 mm) in a cylindrical sample cup having a diameter of 30 mm. After loading the samples to the rheometer they are allowed to rest for 5 min before the measurement is started. The steady state viscosity is measured with a gradually increasing shear stress (proportional to applied torque) and the shear rate (proportional to angular velocity) is measured. The reported viscosity (=shear stress/shear rate) at a certain shear stress is recorded after reaching a constant shear rate or after a maximum time of 2 min. The measurement is stopped when a shear rate of 1000 s$^{-1}$ is exceeded. This method may be used for determining the zero-shear viscosity.

In another example rheological measurements of the hydrogel samples were carried out with a stress controlled rotational rheometer (AR-G2, TA instruments, UK) equipped with 20 mm plate geometry. After loading the samples to the rheometer, 1 mm gap, without dilution, they were allowed to settle for 5 min before the measurement was started. The stress sweep viscosity was measured with gradually increasing shear stress in a range of 0.001-100 Pa at the frequency 10 rad/s, strain 2%, at 25° C. Storage modulus, loss modulus and yield stress/fracture strength can be determined.

In one example the nanofibrillar cellulose, for example provided as a starting material in the method, when dispersed in water, provides a zero shear viscosity ("plateau" of constant viscosity at small shearing stresses) in the range of 1000-100000 Pa·s, such as in the range of 5000-50000 Pa·s, and a yield stress (shear stress where the shear thinning begins) in the range of 1-50 Pa, such as in the range of 3-15 Pa, determined by rotational rheometer at a consistency of 0.5% (w/w) by weight in aqueous medium at 22° C.±1° C. Such nanofibrillar cellulose may also have an average fibril diameter of 200 nm or less, such as in the range of 1-200 nm.

Turbidity is the cloudiness or haziness of a fluid caused by individual particles (total suspended or dissolved solids) that are generally invisible to the naked eye. There are several practical ways of measuring turbidity, the most direct being some measure of attenuation (that is, reduction in strength) of light as it passes through a sample column of water. The alternatively used Jackson Candle method (units: Jackson Turbidity Unit or JTU) is essentially the inverse measure of the length of a column of water needed to completely obscure a candle flame viewed through it.

Turbidity may be measured quantitatively using optical turbidity measuring instruments. There are several commercial turbidometers available for measuring turbidity quantitatively. In the present case the method based on nephelometry is used. The units of turbidity from a calibrated nephelometer are called Nephelometric Turbidity Units (NTU). The measuring apparatus (turbidimeter) is calibrated and controlled with standard calibration samples, followed by measuring of the turbidity of the diluted NFC sample.

In one turbidity measurement method, a nanofibrillar cellulose sample is diluted in water, to a concentration below the gel point of said nanofibrillar cellulose, and turbidity of the diluted sample is measured. Said concentration where the turbidity of the nanofibrillar cellulose samples is measured is 0.1%. HACH P2100 Turbidometer with a 50 ml measuring vessel is used for turbidity measurements. The dry matter of the nanofibrillar cellulose sample is determined and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidimeter. Three measurements on each vessel are carried out. The mean value and standard deviation are calculated from the obtained results, and the final result is given as NTU units.

One way to characterize nanofibrillar cellulose is to define both the viscosity and the turbidity. Low turbidity refers to small size of the fibrils, such as small diameter, as small fibrils scatter light poorly. In general as the fibrillation degree increases, the viscosity increases and at the same time the turbidity decreases. This happens, however, until a certain point. When the fibrillation is further continued, the fibrils finally begin to break and cannot form a strong network any more. Therefore, after this point, both the turbidity and the viscosity begin to decrease.

In one example the turbidity of anionic nanofibrillar cellulose is lower than 90 NTU, for example from 3 to 90 NTU, such as from 5 to 60, for example 8-40 measured at a consistency of 0.1% (w/w) in aqueous medium, and measured by nephelometry. In one example the turbidity of native nanofibrillar may be even over 200 NTU, for example from 10 to 220 NTU, such as from 20 to 200, for example 50-200 measured at measured at 20° C.±1° C. a consistency of 0.1% (w/w) in aqueous medium, and measured by nephelometry. To characterize the nanofibrillar cellulose these ranges may be combined with the viscosity ranges of the nanofibrillar cellulose, such as zero shear viscosity, storage modulus and/or yield stress.

Nanofibrillar cellulose may be or comprise non-modified nanofibrillar cellulose. The modification may refer to chemical, enzymatical and/or physical modification. The drainage of non-modified nanofibrillar cellulose is significantly faster than for example anionic grade. Non-modified nanofibrillar cellulose generally has a Brookfield viscosity in the range of 2000-10000 mPa·s, measured at 20° C.±1° C., at a consistency of 0.8% (w/w) and at 10 rpm. It is preferred that the nanofibrillar cellulose has a suitable carboxylic acid content, such as in the range of 0.6-1.4 mmol COOH/g, for example in the range of 0.7-1.2 mmol COOH/g, or in the range of 0.7-1.0 mmol COOH/g or 0.8-1.2 mmol COOH/g, determined by conductometric titration.

The disintegrated fibrous cellulosic raw material may be modified fibrous raw material. Modified fibrous raw material means raw material where the fibers are affected by the treatment so that cellulose nanofibrils are more easily detachable from the fibers. The modification is usually performed to fibrous cellulosic raw material which exists as a suspension in a liquid, i.e. pulp.

The modification treatment to the fibers may be chemical, enzymatic or physical. In chemical modification the chemical structure of cellulose molecule is changed by chemical reaction ("derivatization" of cellulose), preferably so that the length of the cellulose molecule is not affected but functional groups are added to β-D-glucopyranose units of the polymer. The chemical modification of cellulose takes place at a certain conversion degree, which is dependent on the dosage of reactants and the reaction conditions, and as a rule it is not complete so that the cellulose will stay in solid form as fibrils and does not dissolve in water. In physical modification anionic, cationic, or non-ionic substances or any combination of these are physically adsorbed on cellulose surface.

The cellulose in the fibers may be especially ionically charged after the modification. The ionic charge of the cellulose weakens the internal bonds of the fibers and will later facilitate the disintegration to nanofibrillar cellulose. The ionic charge may be achieved by chemical or physical modification of the cellulose. The fibers may have higher anionic or cationic charge after the modification compared with the starting raw material. Most commonly used chemical modification methods for making an anionic charge are oxidation, where hydroxyl groups are oxidized to aldehydes and carboxyl groups, sulphonylation and carboxymethylation. Chemical modifications introducing groups, such as carboxyl groups, which may take part in forming a covalent bond between the nanofibrillar cellulose and the bioactive molecule, may be desired. A cationic charge in turn may be created chemically by cationization by attaching a cationic group to the cellulose, such as quaternary ammonium group.

Nanofibrillar cellulose may be or comprise chemically modified nanofibrillar cellulose, such as anionically modified nanofibrillar cellulose or cationically modified nanofibrillar cellulose. In one example the nanofibrillar cellulose is anionically modified nanofibrillar cellulose. In one example the anionically modified nanofibrillar cellulose is oxidized nanofibrillar cellulose. In one example the anionically modified nanofibrillar cellulose is sulphonized nanofibrillar cellulose. In one example the anionically modified nanofibrillar cellulose is carboxymethylated nanofibrillar cellulose. The material obtained with the anionical modification of cellulose may be called anionic cellulose, which refers to material wherein the amount or proportion of anionic groups, such as carboxylic groups, is increased by the modification, when compared to a non-modified material. It is also possible to introduce other anionic groups to the cellulose, instead or in addition to carboxylic groups, such as phosphate groups or sulphate groups. The content of these groups may be in the same ranges as is disclosed for carboxylic acid herein.

The cellulose may be oxidized. In the oxidation of cellulose, the primary hydroxyl groups of cellulose may be oxidized catalytically by a heterocyclic nitroxyl compound, such as through N-oxyl mediated catalytic oxidation, for example 2,2,6,6-tetramethylpiperidinyl-1-oxy free radical, generally called "TEMPO". The primary hydroxyl groups (C6-hydroxyl groups) of the cellulosic β-D-glucopyranose units are selectively oxidized to carboxylic groups. Some aldehyde groups are also formed from the primary hydroxyl groups. Regarding the finding that low degree of oxidation does not allow efficient enough fibrillation and higher degree of oxidation inflicts degradation of cellulose after mechanical disruptive treatment, the cellulose may be oxidized to a level having a carboxylic acid content in the oxidized cellulose in the range of 0.5-2.0 mmol COOH/g pulp, 0.6-1.4 mmol COOH/g pulp, or 0.8-1.2 mmol COOH/g pulp, preferably to 1.0-1.2 mmol COOH/g pulp, determined by conductometric titration. When the fibers of oxidized cellulose so obtained are disintegrated in water, they give stable transparent dispersion of individualized cellulose fibrils, which may be, for example, of 3-5 nm in width. With oxidized pulp as the starting medium, it is possible to obtain nanofibrillar cellulose where Brookfield viscosity measured at a consistency of 0.8% (w/w) is at least 10000 mPa·s, for example in the range of 10000-30000 mPa·s.

Whenever the catalyst "TEMPO" is mentioned in this disclosure, it is evident that all measures and operations where "TEMPO" is involved apply equally and analogously to any derivative of TEMPO or any heterocyclic nitroxyl radical capable of catalyzing selectively the oxidation of the hydroxyl groups of C6 carbon in cellulose.

In one example such chemically modified nanofibrillar cellulose, when dispersed in water, provides a Brookfield viscosity of at least 10000 mPa·s measured at 20° C.±1° C., at a consistency of 0.8% (w/w) and at 10 rpm. In one example such chemically modified nanofibrillar cellulose, when dispersed in water, provides a Brookfield viscosity of at least 15000 mPa·s measured at 20° C.±1° C., at a consistency of 0.8% (w/w) and at 10 rpm. In one example such chemically modified nanofibrillar cellulose, when dispersed in water, provides a Brookfield viscosity of at least 18000 mPa·s measured at 20° C.±1° C., at a consistency of 0.8% (w/w) and at 10 rpm. Examples of anionic nanofibrillar celluloses used have a Brookfield viscosity in the range of 13000-15000 mPa·s or 18000-20000 mPa·s, or even up to 25000 mPa·s, depending on the degree of fibrillation.

In one example the nanofibrillar cellulose is TEMPO oxidized nanofibrillar cellulose. It provides high viscosity at low concentrations, for example a Brookfield viscosity of at least 20000 mPa·s, even at least 25000 mPa·s, measured at 20° C.±1° C., at a consistency of 0.8% (w/w) and at 10 rpm. In one example the Brookfield viscosity of TEMPO oxidized nanofibrillar cellulose is in the range of 20000-30000 mPa·s, such as 25000-30000 mPa·s, measured at 20° C.±1° C., at a consistency of 0.8% (w/w) and at 10 rpm.

In one example the nanofibrillar cellulose is or comprises chemically unmodified nanofibrillar cellulose. In one example such chemically unmodified nanofibrillar cellulose, when dispersed in water, provides a Brookfield viscosity of at least 2000 mPa·s, or at least 3000 mPa·s, measured at 20° C.±1° C., at a consistency of 0.8% (w/w) and at 10 rpm.

In one example the nanofibrillar cellulose is or comprises enzymatically unmodified nanofibrillar cellulose. The enzymatically unmodified nanofibrillar cellulose may be chemically modified or chemically unmodified nanofibrillar cellulose.

Auxiliary agents, including additives, for enhancing the manufacturing process or improving or adjusting the properties of the product may be included in the nanofibrillar cellulose dispersion. Such auxiliary agents may be soluble in the liquid phase of the dispersion, they may form an emulsion or they may be solid. Auxiliary agents may be added already during the manufacturing of the nanofibrillar cellulose dispersion to the raw material or they may be added to a formed nanofibrillar cellulose dispersion or gel. The auxiliary agents may be also added to the final product, for example by impregnating, spraying, dipping, soaking or the like method. The auxiliary agents are usually not covalently bound to the nanofibrillar cellulose, so they may be releasable from the nanocellulose matrix. A controlled and/or sustained release of such agents may be obtained when using NFC as matrix. Examples of auxiliary agents include therapeutic (pharmaceutic) agents and other agents affecting to the properties of the product or to the properties of the active agents, such as buffers, surfactants, plasticizers, emulsifiers or the like. In one example the dispersion contains one or more salts, which may be added to enhance the properties of the final product or to facilitate water removal from the product in the manufacturing process. Examples of salts include chloride salts, such as sodium chloride, calcium chloride and potassium chloride. The salt may be included in an amount in the range of 0.01-1.0% (w/w) of the dry matter in the dispersion. The final product may also be dipped or soaked in a solution of sodium chloride, such as in an aqueous solution of about 0.9% sodium chloride. Desired salt content in the final product may be in the range of 0.5-1%, such as about 0.9%, of the volume of the wet product. The salts, buffers and the like agents may be provided to obtain physiological conditions.

Multivalent cations may be included to obtain non-covalent crosslinking of the nanofibrillar cellulose. One example provides a nanofibrillar cellulose product comprising nanofibrillar cellulose, especially comprising anionically modified nanofibrillar cellulose, and multivalent cations, such as multivalent metal cations, for example selected from cations of calcium, magnesium, zinc, aluminum, gold, platinum and titanium, wherein the nanofibrillar cellulose is crosslinked by the multivalent cations. The amount of the multivalent cations may be in the range of 0.1-3% (w/w), for example 0.1-2% (w/w) calculated from the dry content of the hydrogel.

One example provides a method for preparing such a hydrogel, the method comprising providing pulp, disintegrating the pulp until nanofibrillar cellulose is obtained, forming the nanofibrillar cellulose into a hydrogel The nanofibrillar cellulose may be fibrillated into a desired fibrillation degree and adjusted into desired water content, or otherwise modified, so that it forms a gel having desired properties as described herein. In one example the nanofibrillar cellulose in the hydrogel is anionically modified nanofibrillar cellulose.

The present application provides use of nanofibrillar cellulose for preparing the medical products described herein.

The hydrogel to be used as a medical or scientific hydrogel needs to be homogenous. Therefore the method for preparing the hydrogel may include homogenizing a hydrogel comprising nanofibrillar cellulose, preferably with a homogenizing device such as ones described herein. With this preferably non-fibrillating homogenizing step it is possible to remove areas of discontinuity from the gel. A homogenous gel having better properties for the applications is obtained. The hydrogel may be further sterilized, for example by using heat and/or radiation, and/or by adding sterilizing agents, such as antimicrobials.

The starting concentration of the nanofibrillar cellulose dispersion, usually aqueous dispersion, which is provided for treating the nonwoven in an immersion step, may be in the range of 0.1-10%. A concentrated dispersion may be diluted prior to use. However, the concentration is usually not higher than 5%, for example in the range of 0.3-5.0%, for example in the range of 0.8-1.2%. This is usually the initial concentration of the nanofibrillar cellulose at the exit of the manufacturing process where it is manufactured by disintegrating fibrous raw material. However, it is possible that the nanofibrillar cellulose dispersion is diluted with a liquid from the initial concentration (concentration of the product from the manufacturing process) to a suitable starting concentration to ensure that it is distributed or impregnated evenly into the nonwoven. Depending on the characteristic viscosity of the nanofibrillar cellulose grade, the starting concentration may be lower or higher, and it may be in the range of 0.1-10%. Higher concentrations may be used for low-viscosity grades, which may be spread uniformly on the filter fabric despite the high concentration. The nanofibrillar cellulose issues as aqueous nanofibrillar cellulose from a manufacturing process where the fibrous starting material suspended in water is disintegrated. Draining of the liquid out of the nanofibrillar cellulose dispersion may be called "dewatering" in the case of water or aqueous solution.

Auxiliary agents for enhancing the manufacturing process or improving or adjusting the properties of the product may be included in the nanofibrillar cellulose dispersion. Such auxiliary agents may be soluble in the liquid phase of the dispersion, they may form an emulsion or they may be solid. Auxiliary agents may be added already during the manufacturing of the nanofibrillar cellulose dispersion to the raw material or added to a nanofibrillar cellulose dispersion before the immersion. The auxiliary agents may be also added to the final product, for example by impregnating. Examples of auxiliary agents include therapeutic and cosmetic agents and other agents affecting to the properties of the product or to the properties of the active agents, such as surfactants, plasticizers, emulsifiers or the like. In one example the dispersion contains one or more salts, which may be added to enhance the properties of the final product or to facilitate water removal from the product in the manufacturing process. One example of the salt is sodium chloride. The salt may be included in an amount in the range of 0.01-1.0% (w/w) of the dry matter in the dispersion. The final product may also be dipped or soaked in a solution of sodium chloride, such as in an aqueous solution of about 0.9% sodium chloride. Desired sodium chloride content in the final product may be in the range of 0.5-1%, such as about 0.9%, of the volume of the wet product. The cytotoxicity of the NFC wound dressings described herein has been assessed by means of the XTT test using mouse cells. The NFC wound dressing was extracted under agitation, after which the cells were incubated with different end concentrations of the extract. The highest extract concentration corresponds to the ISO 10993-5 and 10993-12 described weight/volume ratio of 0.2 g/ml. The extraction procedure did not reveal any abnormalities in the extraction medium or the test item. No changes regarding clarity, color, and presence or absence of foreign material occurred in the extraction medium. The pH-value of the test extract was 7.5 (solvent control pH 7.5).

The results showed no relevant reduction of cell proliferation and/or cell viability. With the highest extract concentration (100%), the dehydrogenase activity was not reduced. Microscopically, no inhibition of cell growth and no cell lysis were observed at all extract concentrations used. The controls confirmed the validity of the study. Between the solvent control and the negative control, no relevant difference could be observed. The positive control showed a distinct reduction in cell viability and cell proliferation, as dehydrogenase activity was reduced to 1%.

Use of the Medical Products

The medical products may be used in several applications. One specific field is medical applications, wherein the materials are applied on living tissue, such as skin. The structures may be used in medical products, such as patches, dressings, bandages, filters and the like. The medical products may also be therapeutic products, such as therapeutic patches containing medicament. In general the surface of the product comprising nanofibrillar cellulose will be in contact with the skin during the use. A surface of nanofibrillar cellulose may provide advantageous effects when it is in direct contact with the skin, for example it may promote healing of a wound or other damage on a skin, or it may promote migration or delivery of substances from the skin to the medical product and/or from the medical product to the skin.

The term "wound" as used herein refers to any damages, injuries, diseases, disorders or the like on a tissue, such as skin, including open or closed wounds, wherein the healing of the wound is desired and may be promoted with the product described herein. The wound may be clean, contaminated, infected or colonized, wherein especially in the latter cases a therapeutic agent, such as an antibiotic, may be administered. Examples of open wounds include abrasions, avulsions, incisions, lacerations, puncture wounds and penetration wounds. Examples of closed wounds include burns, hematomas, crush injuries, sewn wounds, grafts and any applicable skin conditions, diseases or disorders. Examples of conditions, diseases or disorders of the skin include acne, infections, vesiculobullous diseases, cold sore, cutaneous candidiasis, cellulitis, dermatitis and eczema, herpes, hives, lupus, papulosquamous, urticaria and erythema, psoriasis, rosacea, radiation-related disorders, pigmentation, mucinoses keratosis, ulcer, such as pressure ulcer, atrophy, and necrobiosis, vasculitis, vitiligo, warts, neutrophilic and eosinophilic diseases, congenital, neoplasms and cancer, such as melanomas and tumours of epidermis or dermis, or other diseases or disorders of epidermis and dermis, such as fully or partially breached dermis.

One example provides the medical product for use for treating and/or covering skin wounds or other damages. One example provides such a medical product for use as a dressing or a patch, or in a dressing or a patch, for treating and/or covering skin wounds or other damages.

One example provides such a medical product for use for treating and/or covering skin wounds covered with a graft, such as a skin graft. One example provides such a medical product for use as a dressing or a patch, or in a dressing or a patch, for treating and/or covering skin wounds covered with a graft, such as a skin graft.

The medical products may be used in a variety of treatment methods comprising providing the medical product, and treating a subject with the medical product, for example applying the medical product onto the subject.

The subject may be a patient, such as human or animal patient. In one example the method comprises
  recognizing a subject in need of therapy requiring healing of a wound,
  providing the medical product, and
  applying the medical product onto the wound in the subject.

In analogous way the medical product may be used for treating any other suitable disease or disorder of skin or below tissue in a subject, such as epidermis. In one example the method comprises
  recognizing a subject in need of therapy requiring healing of skin,
  providing the medical product, and
  applying the medical product onto the skin of the subject.

The medical product may be provided for use for treating and/or covering skin wounds or other damages or injuries, such as deep skin wounds involving dermis damage.

The present disclosure presents a method for treating skin wounds or other damages or injuries, the method comprising applying the medical product described herein onto the wound, damage, or injury. One specific example presents a method for treating skin wounds covered with a graft, such as a skin graft, for example a mesh graft or a full thickness graft, the method comprising applying the medical product described herein onto the graft.

Grafting refers to a surgical procedure to move tissue from one site to another on the body, or from another person, without bringing its own blood supply with it. Instead, a new blood supply grows in after it is placed. Autografts and isografts are usually not considered as foreign and, therefore, do not elicit rejection. Allografts and xenografts are recognized as foreign by the recipient and are rejected.

Skin grafting is often used to treat skin loss due to a wound, burn, infection, or surgery. In the case of damaged skin, it is removed, and new skin is grafted in its place. Skin grafting can reduce the course of treatment and hospitalization needed, and can also improve function and appearance. There are two types of skin grafts: Split-thickness skin grafts (epidermis+part of the dermis) and full-thickness skin grafts (epidermis+entire thickness of the dermis).

A mesh graft is a full- or partial-thickness sheet of skin that has been fenestrated to allow drainage and expansion. Mesh grafts are useful in many locations on the body because they conform to uneven surfaces. They can be placed in locations that have excessive motion because they can be sutured to the underlying wound bed. Additionally, their fenestrations provide outlets for fluid that may accumulate beneath the graft, which helps reduce tension and the risk of infection and improve vascularization of the graft.

It was found out in the clinical tests that the medical product attaches to a graft area and acts as a protective layer. As the graft heals, the product forms a scab-like structure together with the graft. The properties of the product comprising nanofibrillar cellulose promote the healing, and the medical product with the formed dry scab will come loose in similar way as a regular scab behaves in normal wound healing process. This decreases the scarring of the wound and/or results in a scar with a good quality.

The treatment may require skin graft donor site management, which is a concern particularly for elderly patients and patients with poor wound healing competence, and also because donor sites are a source of pain and discomfort. The NFC dressing serves as an effective wound dressing in donor site care due to its one-time use, since it does not require dressing changes, which, in turn, may also reduce subjective pain experienced by the patient. The same applies to treatment of other conditions as well.

The medical product may be provided for use for administering bioactive or therapeutic agents or substances.

The medical product may be provided for use for treating skin wound or other damage with a method comprising applying the product onto the wound to absorb bioactive agents from the wound, storing the bioactive agents in the product for a period of time, and allowing the bioactive agents to diffuse back to the wound or other damage at a later phase of the healing process of the wound or damage.

One embodiment provides a medical product, such as a dressing, a patch or a filter, comprising the medical product described herein.

A dressing is a sterile pad or compress applied to a wound to promote healing and/or prevent further harm. A dressing is designed to be in direct contact with the wound, as distinguished from a bandage, which is most often used to hold a dressing in place. Some organizations classify them as the same thing (for example, the British Pharmacopoeia) and the terms are used interchangeably by some people. Dressings are frequently used in first aid and nursing.

One example provides the medical product for use for administering therapeutic agent. In such case the medical product may be provided as such or for example in a patch. One or more therapeutic agent(s) may be included, for example impregnated, in the product as described herein, and the administration to a patient may be dermal or transdermal.

A medical product comprising a therapeutic agent may be provided, wherein the nonwoven and/or the coating layer comprising nanofibrillar cellulose contain(s) one or more therapeutic agent, such as a medicament or drug. Also the term pharmaceutical agent may be used interchangeably instead of the term therapeutic agent. Such agents are active or effective agents, which are usually present in effective amounts. Such an agent may be provided in a predetermined amount, for example in an amount configured to provide a desired dose of the agent during a certain time period, and/or configured to provide a desired effect on the target, such as wound, skin or other tissue. The content of the therapeutic agent in the product may be for example in the range of 0.1-5%. Especially if the therapeutic agent is included, a sustained or prolonged release of the agent may be provided. In such case the nanofibrillar cellulose may contain a portion of moisture to enable permeability of the agent. The moisture content of the product comprising therapeutic agent may be in the range of 0-10%, such as in the range of 5-7%. The therapeutic agents may be present in water-soluble form, fat-soluble form or in an emulsion, or in another suitable form.

Examples of therapeutic agents which may be administered by using the medical products described herein include antibiotics, pain relievers, such as lidocaine; nicotine; opioids, such as fentanyl or buprenorphine; hormones, such as estrogen, contraceptives or testosterone; nitroglycerin; scopolamine; clonidine; antidepressants, such as selegiline; ADHD medication, such as methylphenidate; vitamins, such as B12 or cyanocobalamin; 5-hydroxytryptophan; Alzheimer's medication, such as rivastigmine; acne medication; antipsoriatics, glucocorticoids such as hydrocortisone; or any other medication for treating diseases or disorders of a skin. Therapeutic agents may be used for example in medical patches, which may be used on healthy skin or on damaged skin, to provide a prolonged, sustained or extended release of the therapeutic agent from the patch, for example during a period of several hours, for up to 6, 12, 24 or even 48 hours.

One example provides the medical product comprising antibiotic agent. Such a product is especially suitable for treating wounds, wherein the wound treating properties are combined with antibiotic properties which prevents infections caused by harmful microbes in the wound. Examples of suitable antibiotics include especially topical antibiotics, such as bacitracin, erythromycin, clindamycin, gentamycin, neomycin, polymyxin, mupirocin, tetracycline, meclocycline, (sodium) sulfacetamide, benzoyl peroxide, and azelaic acid, and combinations thereof. Also other types of antibiotics, such as systemic antibiotics, may be provided, for example penicillins, such as phenoxymethylpenicillin, flucloxacilline and amoxicillin; cephalosporins, such as cefaclor, cefadroxil and cephalexin; tetracyclines, such as tetracycline, doxycycline and lymecycline; aminoglycosides, such as gentamicin and tobramycin; macrolides, such as erythromycin, azithromycin and clarithromycin; clindamycin; sulphonamides and trimethoprim; metronidazole and tinidazole; quinolones, such as ciprofloxacin, levofloxacin and norfloxacin.

Antibiotics may be also used for treating acne, for example clindamycin, erythromycin, doxycycline, tetracycline etc. Also other agents may be used, such as benzoyl peroxide, salicylic acid, topical retinoid medicines, such as tretinoin, adapalene or tazarotene, azelaic acid, or androgen blockers such as spirolactone. Psoriasis may be treated for example with steroids, such as corticosteroids, moisturizers, calcipotriene, coal tar, vitamin D, retinoids, tazarotene, anthralin, salicylic acid, methotrexate, or cyclosporine. Insect bites or poison ivy exposure may be treated with agents such as hydrocortisone, emu oil, almond oil, ammonia, bisabolol, papain, diphenylhydramine, jewelweed extract or calamine. Some of these or other treatment agents may be also categorized as cosmetic agents.

One example provides a cosmetic product, such as a dressing, a mask or a patch, comprising the medical product. Such a product may be called also as a cosmetic product. The product may be provided in various shapes, for example a mask may be designed to fit onto face, for example below eye or onto chin, nose or forehead. One example provides the medical product for use as a cosmetic product. The product may be used for releasing one or more cosmetic agent(s) to the user, such as to the skin of the user. Such a cosmetic product may comprise one or more cosmetic agent(s). Cosmetic agent(s) may be included, for example impregnated, in the product wherefrom they will be released or delivered. The content of a cosmetic agent in the product may be for example in the range of 0.1-5%. The cosmetic agents may be present or provided in the product similarly as explained above for therapeutic agents, and vice versa. The cosmetic use may be analogous to medical use described herein, especially the administering of therapeutic agent. Cosmetic agents may be used also for cosmetically treating skin diseases or disorders, such as those mentioned herein. Such cosmetic products may be used for example for treating pimples, acneic skin, brown sports, wrinkles, oily skin, dry skin, aged skin, spider veins, after sun erythemas, black circles etc. Examples of cosmetic patches include skin cleansers, such as pore cleansers, blackhead removers, stretching stripes, short-term patch-like masks, short-term treatment patches and overnight treatment patches.

Examples of cosmetic agents include forms of vitamins and precursors thereof, such as vitamin A; for example retinoids, such as retinaldehyde (retinal), retinoic acid, retinyl palmitate and retinyl retinoate, ascorbic acid, alpha-hydroxy acids such as glycolic acid and lactic acid; glycols; biotechnology products; keratolytics; amino acids; antimicrobials; moisturizers; pigments; antioxidants; plant extracts; cleansing agents or make-up removers; anti-cellulite agents such as caffeine, carnitine, *Ginkgo biloba* and horse-chestnut; conditioners; fragrances such as aromatherapy agents and perfumes; humectants such as urea, hyaluronic acid, lactic acid and glycerine; emollients such as lanolin, triglycerides and fatty acid esters; FR scavengers, singlet oxygen scavengers, superoxide scavengers or hydrogen peroxide scavengers, such as ascorbic acid (vitamin C), glutathione, tocopherol (vitamin E), carotenoids, coenzyme Q10, bilirubin, lipoic acid, uric acid, enzyme mimetic agents, idebenone, polyphenols, selenium, spin traps such as phenyl butyl nitrone (PBN), protein methionine groups, superoxide dismutase, catalase, selenium peroxidases, heme oxygenases etc. or combinations thereof. The cosmetic agents may be present in water-soluble form, fat-soluble form or in an emulsion, or in another suitable form.

One example provides a method for cosmetically treating skin, the method comprising applying the medical product described herein onto skin.

A "patch" as used herein refers to a medical or cosmetic product which may be applied onto skin. Examples of patches include dermal patch and transdermal patch. A dermal patch or skin patch is a medicated adhesive patch that is placed on the skin to deliver a medication into the skin. A transdermal patch is a medicated adhesive patch that is applied on the skin to deliver a specific dose of medication through the skin and into the bloodstream. In one example this promotes healing to an injured area of the body. A patch may contain a release liner, which protects the patch during storage and is removed prior to use, and/or adhesive for adhering the patch to the skin, and/or backing for protecting the patch from the outer environment. Examples of release liners include paper-based liners, such as glassine paper, densified Kraft super-calendered paper, clay-coated paper, silicone-coated paper and polyolefine-coated paper; plastic based liner, such as polystyrene, polyester, polyethylene, cast polypropylene and polyvinyl chloride; and composite material liners based on the combination of several films. Adhesive layers may contain for example pressure sensitive adhesive (PSA).

Before applying the medical product onto skin the product may be pretreated i.e. moisture or wetted, in general with an aqueous solution. The moisturizing or wetting may be carried out for example by using water or regular physiological saline solution, which is usually a solution of about 0.90% w/w of NaCl, having an osmolality of about 308 mOsm/l. Other types of aqueous solutions may also be used, such as saline solutions with different concentrations. Moisturizing or wetting the material enhances contact with the skin and the moldability of a sheet of material.

EXAMPLES

Example 1 18051

Effect of Wound Dressing Comprising NFC Impregnated Nonwoven in an Ex Vivo Model Background
Ex Vivo Skin Microdialysis An ex vivo human skin microdialysis method was developed to characterize inflammatory reactions in the human skin by sampling high molecular weight biomarkers such as cytokines from the extracellular compartment.

Healthy human skin was obtained after surgical removal of abdominal skin for cosmetic reasons.

Biomarker Panel

The biomarkers measured were all chosen due to their relevance to the wound healing process:

Interleukin (IL)-1α:

IL-1α is a cytokine produced by neutrophils, monocytes, macrophages and keratinocytes. Skin injury with disruption of the epidermal barrier mediates an immediate release of prestored IL-1α from keratinocytes, which is one of the first damage signals released to alert surrounding cells. This attracts neutrophils to the wound site to remove bacteria and increases keratinocyte migration and proliferation in an autocrine manner.

IL-1α is upregulated together with other proinflammatory cytokines during the inflammatory phase of wound healing and is known as one of the main inducers of chemokines (together with TNF-α) within a few hours after wounding, thus it serves to amplify inflammatory mediators.

IL-1α might have a protective function, as it strengthens the epidermal barrier by influencing the mechanical attachment of cells. However, as with every other mediator, it requires tight control since deregulated expression seems to promote an inflammatory skin phenotype, e.g. by attracting inflammatory cells.

IL-6:

The cytokine IL-6 is produced by monocytes, macrophages, fibroblasts, endothelial cells, T cells, keratinocytes (the primary source in the skin) and neutrophils. IL-6 is important for initiation of the healing process and exerts important functions in the proliferative phase of wound healing, as it is involved in differentiation and growth of numerous cell types. The biomarker is also found to persists in older wounds. IL-6 has a chemoattractive effect on neutrophils and macrophages and induces collagen deposition, angiogenesis, epidermal cell proliferation indirectly by the induction of TGF-β1, IL-1 and VEGF production (the latter promoting angiogenesis). Furthermore, IL-6 mediates proliferation and migration of keratinocytes. Mice deficient in IL-6 exhibit a delayed healing due to an impaired formation of granulation tissue and a decrease in re-epithelialization, angiogenesis, macrophage/neutrophil infiltration and matrix remodeling. Occlusion of a disrupted skin barrier has been described to prevent the normal induction of IL-6 expression.

IL-17:

In skin wounds, the cytokine IL-17 is primarily produced by dermal γδ T cells, dendritic epidermal T cells and macrophages rather than Th17 cells. The IL-17 receptor is expressed on many cell types including fibroblasts, keratinocytes and other inflammatory cells found in the skin. IL-17 is implicated in many autoimmune diseases and is known as an important mediator in psoriasis, where it is produced in large amounts when γδ T cells are stimulated with IL-23, which causes infiltration of inflammatory cells. Conflicting results have been reported on the role of IL-17 in wound healing. IL-17 knockout mice exposed to a clean wound covered with an occlusive dressing exhibited enhanced wound closure, decrease accumulation of neutrophils, increased myofibroblast differentiation and collagen deposition when compared with wild-type mice. In addition, inhibition of IL-17 by blocking antibodies during the early inflammatory phase was also found to accelerate wound healing. This point towards a negative impact of IL-17 on the healing process and that excessive neutrophilic inflammation mediated by this cytokine is associated with decreased wound healing. However, when wounds were kept open in IL-17 knockout mice, these exhibited delayed healing, which might indicate that microbes are allowed into the wound where they oppose the healing process to a greater extend due to the lack of IL-17 in knockout mice.

Tumor Necrosis Factor (TNF)-α:

TNF-α is a proinflammatory cytokine produced by various cell types such as neutrophils, macrophages, keratinocytes, mast cells and T cells. Its effect on wound healing is highly duration- and dose-dependent, as low levels of TNF-α have been shown to promote wound healing by indirectly mediating inflammation and stimulating macrophages to produce growth factors. High concentrations, however, have a very negative impact on the healing process, especially if TNF-α is present for longer time periods. TNF-α is expressed predominantly by neutrophils within the first hours after wounding and serves as a main inducer of chemokines. During the later phases TNF-α is also expressed by macrophages. TNF-α acts in synergy with other inflammatory mediators, but TNF-α alone or at high concentrations has been shown to decrease re-epithelialization and thereby prevent skin barrier restoration. In contrast, TNF-α application on mice after skin barrier disruption has been shown to increase repair and mice deficient of the TNF-α receptor exhibit delayed permeability barrier repair. TNF-α has been shown to suppress production of extracellular matrix induced by TGF-β and high levels of TNF-α have been observed in chronic non-healing wounds.

Epidermal Growth Factor (EGF):

EGF is a growth factor secreted by platelets, fibroblasts and macrophages. After skin injury, EGF is released together with other mediators such as PDGF and TGF-6 from degranulating platelets during hemostasis. The wound levels of EGF are regulated by the proteolytic environment. EGF acts in a paracrine fashion on keratinocytes serving as an important mitogen and it also promotes keratinocyte migration and thus re-epithelialization. A positive effect of EGF has been seen in a clinical trial in which topical application of EGF on chronic wounds was found to shorten healing time and increase epithelialization.

Interferon (IFN)-γ:

The cytokine IFN-γ seems to be involved in maintaining the skin barrier by regulating the IL-4 and IL-31 receptors, which play a vital role in the formation of the cutaneous barrier by influencing cytokine signaling. IFN-γ also influences detachment of keratinocytes from the basal membrane, which is an essential step in wound healing, as it is part of the differentiation process from basal to primary differentiating suprabasal cells. The lipid envelope, whose primary function is to prevent trans-epidermal water loss (TEWL) and the loss of solutes, is also affected by IFN-γ, as this cytokine is involved in the synthesis of ceramide, thus IFN-γ is involved in regulation of TEWL.

Macrophage Migration Inhibitory Factor (MIF):

MIF is an inflammatory cytokine, which is ubiquitously expressed in the skin, localized to endothelial cells, epidermis, melanocytes and cells of sebaceous and eccrine sweat glands, and has a high expression in keratinocytes. MIF stimulates production of several other cytokines and is strongly induced during cutaneous wound healing, primarily by inflammatory cells during the early phases. In later phases, fibroblasts have been shown to upregulate MIF expression. The effect of MIF on wound healing is controversial, as several studies claim a negative effect, however, disruption of the Mif gene does neither promote nor inhibit healing of incisional wounds in mice, but cotreatment of Mif null mice with recombinant MIF did impair incisional wound healing. MIF is implicated in a range of skin diseases and polymorphism in the Mif gene leading to an increased expression is associated with increased disease severity in more inflammatory diseases. Thus, there is no consensus regarding its role in cutaneous wound healing, but various studies indicate that MIF might inhibit normal repair.

Neutrophil-Activating Peptide (NAP)-2:

NAP-2 (also known as CXCL7) is a CXC chemokine released by activated platelets as chemokine-connective tissue-activating peptide-III (CTAP-III), which is converted proteolytically into neutrophil-activating peptide-2 (NAP-2) by neutrophils. NAP-2 acts as a first-line mediator within minutes after injury and mediates chemotactic effects on neutrophils through the CXCR2 receptor beside inducing proliferation of endothelial cells and angiogenesis.

Materials, Methods and Experimental Design

Test Item

NFC Dressing

The medical products in the form of wound dressings were prepared from nanofibrillar cellulose obtained from bleached birch pulp and polyester-viscose based nonwoven. The medical product according to embodiments is called as NFC dressing in the following.

NFC Dressing

Reference Product

Denomination: Suprathel® wound dressing

Product: A wound dressing product consisting of a synthetic copolymer consisting mainly of DL-lactide (>70%), rimethylenecarbonate and e-caprolactone Intended therapeutic use: Superficial wounds after skin grafting Batch number: P-2014-X/P-2016-X-X Appearance: 9×10 cm white dressing Expiry date: 2017-7/2019-12 Supplier: Polymedics Innovations GmbH, Germany Experimental Study Design According to the protocol, the study was divided into two phases: A 1) pre-testing phase and the 2) main experimental phase:

Pre-Testing Phase:

Initially, the relative biomarker recovery was established for each biomarker in the panel. Furthermore, the pre-phase was used to establish a standardized ex vivo skin wound model induced by skin barrier disruption. This was achieved by analyzing biomarker profiles at three different time points after the initial skin trauma using microdialysis sampling. Both general and cell-specific inflammation biomarkers were investigated.

Main Experimental Phases:

This part of the study aimed to investigate how NFC interacts with the wound healing process in the pre-phase-established ex vivo skin model. This was proposed to be done in three separate studies as follows:

M1. Microdialysis of ex vivo skin with/without skin barrier disruption with NFC wound dressing vs. market leader (Suprathel®) wound dressing material. Read-out: Biomarker profiles in the wound bed.

M2. Analysis of NFC dressing after application on tape-stripped ex vivo skin. Potential cell migration into hydrogel-layer as well as cytokine-content of the cellulose layer will be analyzed. Read-out: Cell-counts and biomarker profiles.

M3. *** Keratinocyte cell line grown with microdialysis dialysates sampled after tape-stripping and NFC application to investigate potential effect of NFC on keratinocyte proliferation and re-epithelization. Readout: Daily keratinocyte growth rates over 5 days.

Donor Skin

Abdominal skin specimens were obtained from patients undergoing cosmetic surgery (e.g. due to presence of excessive skin after pregnancy or after losing weight). The skin was transported at room temperature to Ref Lab in a box supplied with sterile saline immediately after surgical removal.

The skin was fully anonymized and thus obtained and used in this study with ethical approval from the Danish National Committee on Health Research Ethics according to the Committee law § 14, section 3 concerning the use of anonymized human material for research purposes.

Estimation of Relative Biomarker Recoveries

As part of the pre-phase studies, the relative biomarker recoveries were determined using the in-house-developed "skin reservoir model" in which known amounts of the respective biomarkers are injected into thawed skin, which serves as a reference solution reservoir. The biomarkers are then sampled through inserted microdialysis probes (3000 kDa molecular weight cut-off) for two hours at a flow rate of 0.8 µL/min (see procedure for probe insertion and a detailed description of microdialysis sampling in section "4.7 Microdialysis technique"). Subsequently, the biomarker concentrations were measured in the dialysates using commercially available ELISA kits (see section "4.8 Analysis of biomarker profiles in microdialysates") in order to estimate the relative recoveries.

The relative recovery is defined as the biomarker concentration found in the dialysate divided by the concentration injected, thus being the fraction of the biomarker crossing the membrane: $\text{concentration}_{dialysate}/\text{concentration}_{injected} \times 100\%$.

Skin Preparation and Trauma Induction

Pieces measuring approximately 4×6 cm (for the pre-phase experiments) or 4×3 cm (for the main phase experiments) were excised from the abdominal skin according to the respective setups (see below). Subcutaneous fat was trimmed off before the skin specimens were washed shortly in ethanol and antifungals in order to handle it aseptically. In the LAF bench, skin specimens were mounted using sterile needles on Styrofoam with moist tissue paper between the Styrofoam and the skin. The skin specimens were treated according to the setups below, thus either subjected to trauma or kept as no trauma-controls with or without dressing applied.

Deviation from the signed protocol: In the protocol it is stated that "The skin slices are stripped 10-15 times using a 3M cellophane tape in order to simulate a split-thickness skin graft". Induction of trauma by the tape stripping method was not possible in the ex vivo skin model, since it was required to keep the skin moist during the entire procedure and tape does not adhere to wet skin. By experimentation we found that trauma could be induced by rubbing the skin 15 times with sand paper (grit size 150), and this procedure was therefore followed throughout the entire study.

Pre Phase Experimental Setup

The setup depicted in FIG. 1 was repeated in skin from 3 donors from each of which 6 skin specimens were prepared (two for each of three different time points: 6 hours, 24 hours and 48 hours).

Read-out: Dialysate concentrations of IL-1α, IL-6, IL-17, TNF-α, EGF, IFN-γ, MIF and NAP-2.

Main Phase 1+2 Experimental Setup

Figure 2:
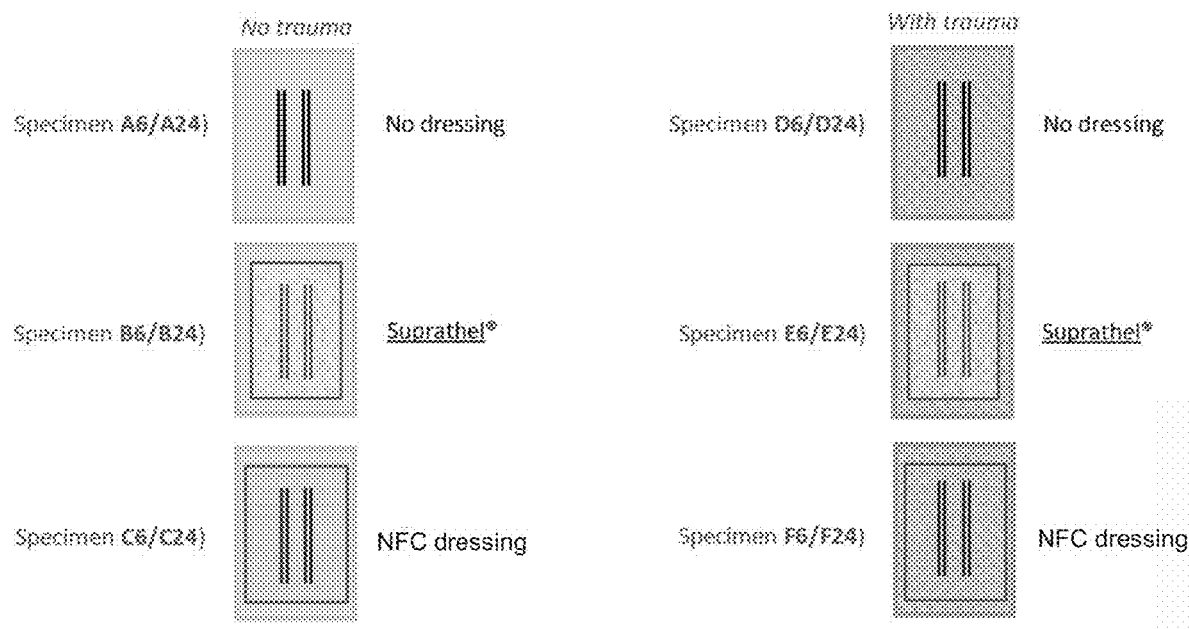
FIG. 2 shows schematic drawing of the experimental setup in the main phases.

The setup depicted in FIG. 2 was repeated in skin from 5 donors from each of which 12 skin specimens were prepared (six for each of two different time points: 6 hours and 24 hours).

Microdialysis was performed after 6 and 24 hours of incubation (M1, time points chosen based on pre-phase experiments).

NFC dressing pieces, which had been incubated on top of skin specimens B6/B24 and E6/E24, were enzymatically degraded for 2 hours using GrowDase™ and then flushed with PBS in order to release biomarkers potentially bound in the hydrogel layer. Both the GrowDase™ fraction and the PBS flush were analyzed for biomarker contents (M2).

Possible cell infiltration was investigated in pellets from GrowDase mixes and in the PBS fractions in NFC dressing pieces from donor 1, however, no cell infiltration was found, thus it was omitted from subsequent experiments.

Read-out: Dialysate concentrations of IL-1α, IL-6, MIF and NAP-2 (M1, biomarkers chosen based on pre-phase experiments) and levels of IL-1α, IL-6, IL-17, TNF-α, EGF, IFN-γ, MIF and NAP-2 in GrowDase-degraded NFC dressing (M2).

Microdialysis Technique

Microdialysis probes were placed intradermally in the skin specimens using 21 G guide cannulas. The microdialysis probes were purchased from EP Medical, Copenhagen, Denmark, and had a molecular weight cut-off of 3000 kDa and a total membrane length of 40 mm, which was attached to the inlet tubing.

In the pre-phase experiments, 4 probes were inserted into each skin specimen, 1 cm apart and with an intradermal length of 20 mm. In the main phase experiments, 2 probes were inserted into each skin specimen (see schematic drawing of the experimental setups above).

The prepared skin specimens with inserted cannulas were incubated at 37° C. in humidified air with 5% $CO_2$ for up to 48 hours (according to the respective setups) on stainless steel grids placed in petri dishes with a RefLab-developed skin medium containing nutrients and antibiotics (DMEM supplemented with 5% FCS, 2 mM GlutaMAX, 1% Penicillin/Streptomycin/Amphotericin and 5 μg/ml recombinant human insulin) beneath the grid to simulate an air-liquid interphase.

After incubation, the skin was removed from the metal grids and placed on moist tissue paper mounted on Styrofoam at room temperature. The microdialysis probes were inserted through the guide cannulas, which were withdrawn, thus leaving the probes inside the skin ready for perfusion using a microperfusion pump (NE-1200-EM, Harvard Apparatus, World Precision Instruments, Hertfordshire, UK). The perfusate consisted of Ringer-lactate supplemented with 1% human albumin and 4 mM lactic acid. The perfusion rate was set to 0.8 μL/min throughout the study and dialysates were sampled continuously for 2 hours in PCR-tubes, which were covered with Parafilm to reduce evaporation. The volume of the dialysates was determined by weighing the PCR tubes before and after sampling. Immediately after weighing, the tubes were stored at −80° C. until analysis to minimize potential breakdown of volatile biomarkers.

Analysis of Biomarker Profiles in Microdialysates

Dialysates (from pre-phase and M1) and samples from GrowDase-degraded NFC dressing (from M2) were analyzed for biomarker concentrations by commercially available DuoSet ELISA kits from R&D according to the manufacturer's instructions. The biomarker panel consisted of: IL-1α, IL-6, IL-17, TNF-α, IFN-γ, EGF, NAP-2 and MIF. Dialysates from the same skin specimen were pooled prior to ELISA analysis.

Statistical Analyses

All statistical analyses were made using GraphPad Prism version 7.0.3 (GraphPad Software Inc., La Jolla, CA, USA). The statistical tests used are specified in figure legends and asterisks designate significance levels based on p-values obtained from statistical testing: *=$p<0.05$, **=$p<0.01$.

Results

Pre Phase Results

Relative Recoveries Measured in the Skin Reservoir Model

The relative recovery, a measure of sampling feasibility, was estimated for every biomarker in the biomarker panel (IL-1α, IL-6, IL-17, TNF-α, EGF, IFN-γ, MIF and NAP-2) using the Ref Lab "skin reservoir model". The results are listed below and summarized in table 1:

1. IL-1α, IL-6, IL-17, TNF-α, EGF and NAP-2 exhibited relative recoveries above the lower level of acceptance, which is usually set to 5%.

2. The relative recovery of MIF could not be quantified since background levels in the thawed skin exceeded the concentration injected and the dialysate concentrations were above the upper level of quantification (ULOQ). However, this finding shows that MIF can indeed be sampled by the microdialysis probe.

3. The relative recovery of IFN-γ was 0.0% and we were therefore unable to measure IFN-γ in the dialysates.

TABLE 1

| | Relative biomarker recovery | | |
|---|---|---|---|
| Biomarker | Average relative recovery (%) | CV (%) | # of donors (triplicate probes pr. donor) |
| EGF | 9.3 | 6.2 | 2 |
| IFN-γ | 0.0 | — | 1 |
| IL-1α | 6.2 | 14.6 | 1 |
| IL-6 | 11.4 | 16.4 | 2 |
| IL-17 | 8.7 | 14.9 | 1 |
| MIF | (Background too high) | — | 1 |
| NAP-2 | 7.2 | 43.4 | 2 |
| TNF-α | 9.6 | 21.6 | 2 |

Establishing the Ex Vivo Wound Model

Figure 3:
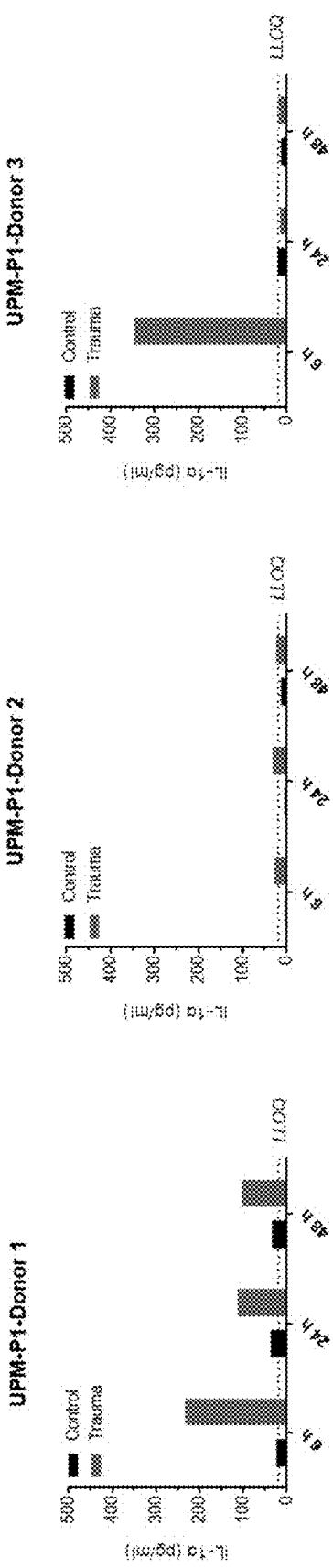
FIG. 3 shows dialysate levels of IL-1α (n=3 donors). LLOQ=Lower limit of quantification.
Figure 4:
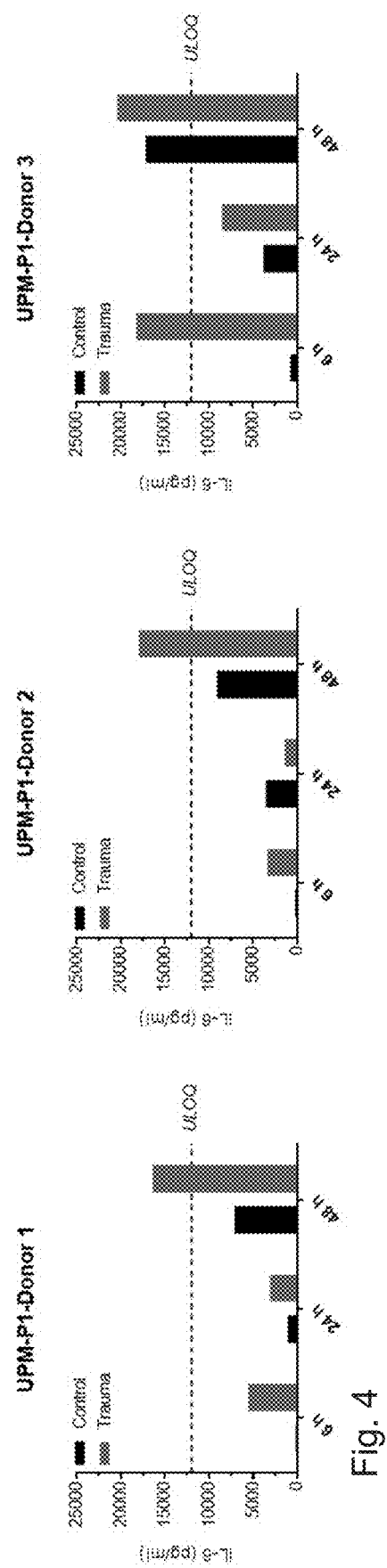
FIG. 4 shows dialysate levels of IL-6 (n=3 donors). ULOQ=Upper limit of quantification.
Figure 5:
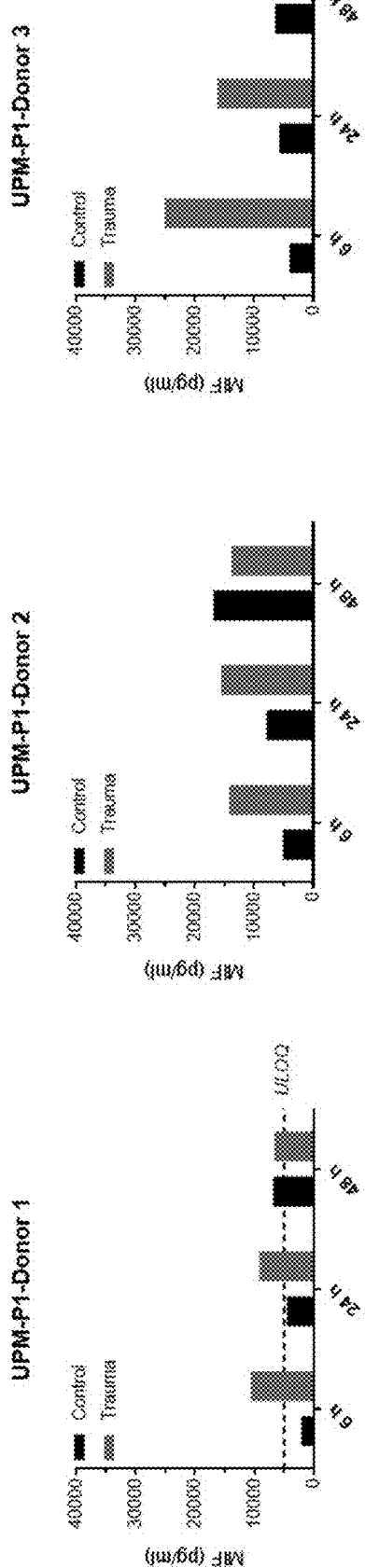
FIG. 5 shows dialysate levels of MIF (n=3 donors). ULOQ=Upper limit of quantification.
Figure 6:
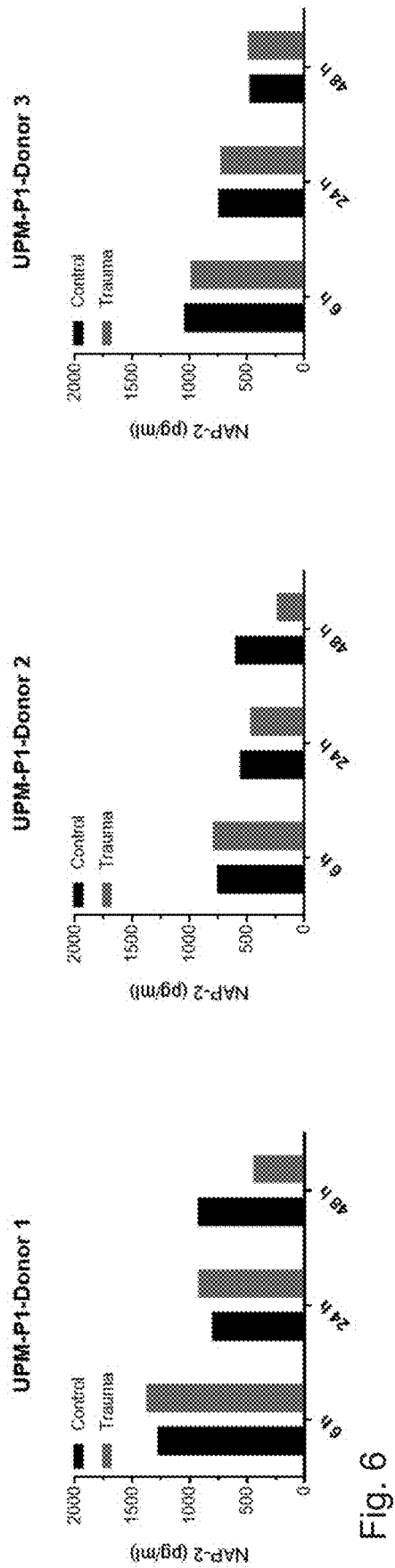
FIG. 6 shows dialysate levels of NAP-2 (n=3 donors).

All eight biomarkers were quantified in dialysates from control specimens and skin specimens subjected to trauma as part of the pre-phase (FIG. 1). We found four out of the eight biomarkers investigated to be detectable in concentrations above the lower limit of quantification (LLOQ):

IL-1α was highly upregulated by trauma in all three donors with the highest upregulation after 6 hours. Basal levels seemed unchanged up to 48 hours (FIG. 3). IL-6 was highly upregulated by trauma in all three donors after 6 hours. After 24 and 48 hours, the upregulation is accompanied by increasing basal levels (FIG. 4). MIF was upregulated due to trauma in all three donor skin specimens but mainly after 6 and 24 hours. Basal levels are upregulated after 24 and 48 hours (FIG. 5). A high basal level of NAP-2 ranging from 800 to 1300 pg/mL was observed in all three donors but was not further upregulated in traumatized skin (FIG. 6).

Figure 7:
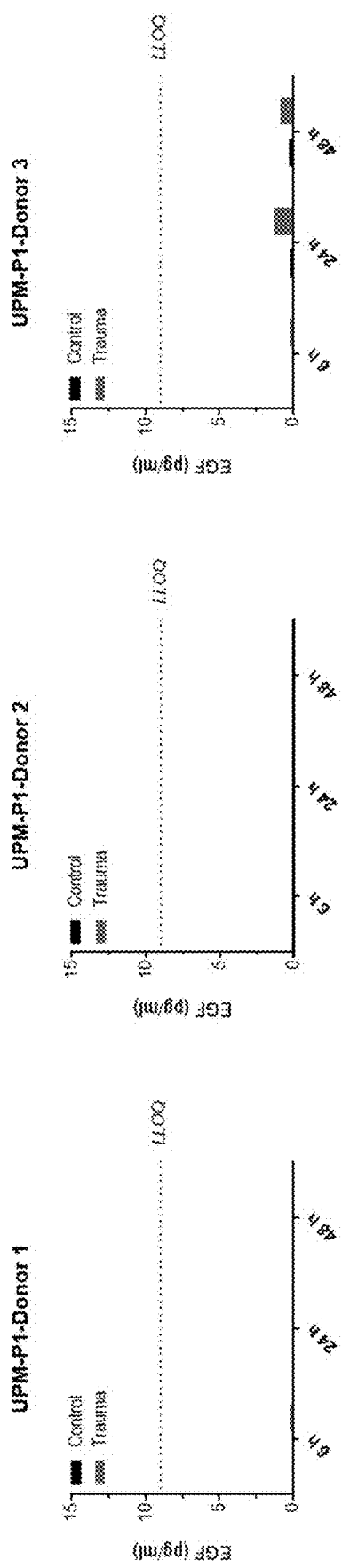
FIG. 7 shows dialysate levels of EGF (n=3 donors). LLOQ=Lower limit of quantification.
Figure 8:
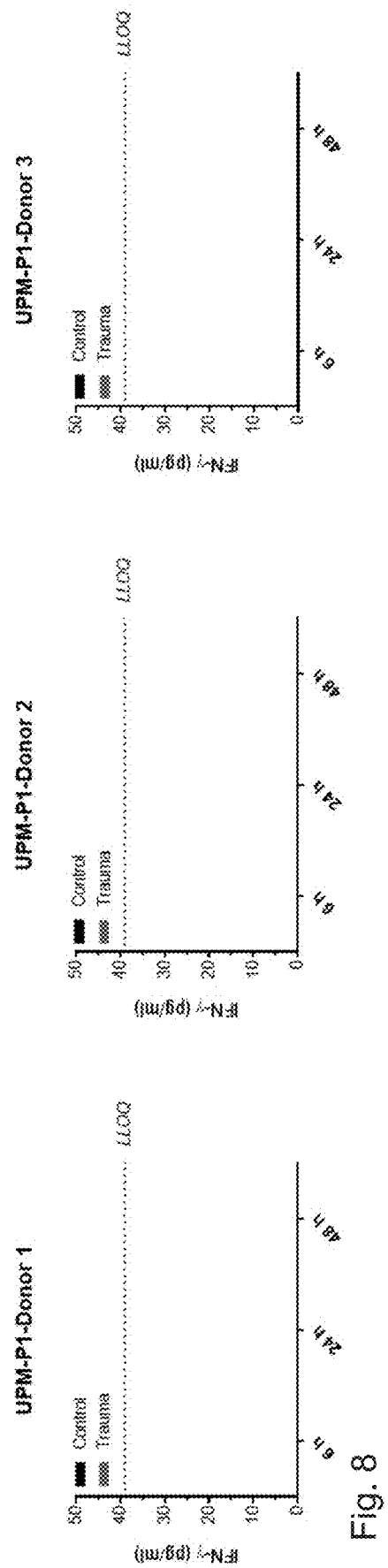
FIG. 8 shows dialysate levels of IFN-γ (n=3 donors). LLOQ=Lower limit of quantification.
Figure 9:
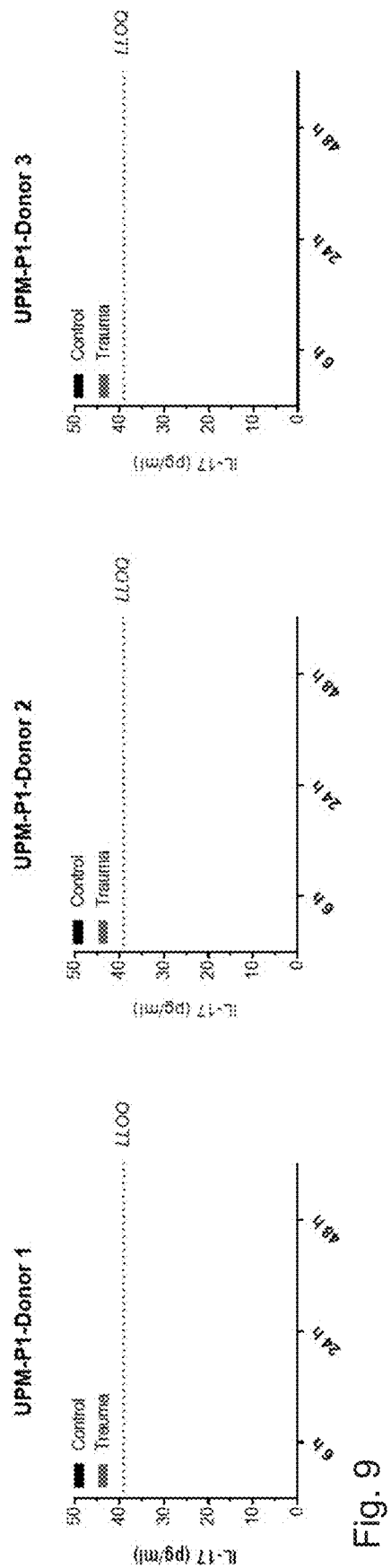
FIG. 9 shows dialysate levels of IL-17 (n=3 donors). LLOQ=Lower limit of quantification.
Figure 10:
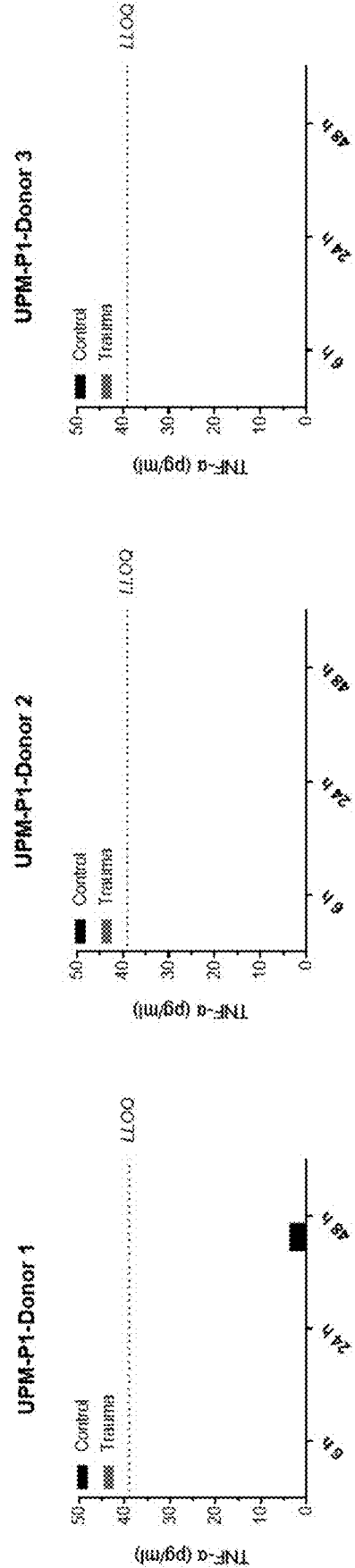
FIG. 10 shows dialysate levels of TNF-α (n=3 donors). LLOQ=Lower limit of quantification.

In contrast, EGF (FIG. 7), IFN-γ (FIG. 8), IL-17 (FIG. 9) and TNF-α (FIG. 10) were either absent in the dialysates or below LLOQ. The fact that we were unable to sample IFN-γ using the microdialysis probes (table 1) explains the absence of this cytokine in the dialysates (FIG. 8).

Main Phase 1

Based on the results from the pre-phase, in which the human ex vivo skin wound model was established, IL-1α, IL-6, MIF and NAP-2 were quantified in dialysates after treatment with NFC dressing and Suprathel®. All eight biomarkers were quantified in samples from GrowDase™-degraded NFC dressing.

IL-1α levels in dialysates

Figure 11:
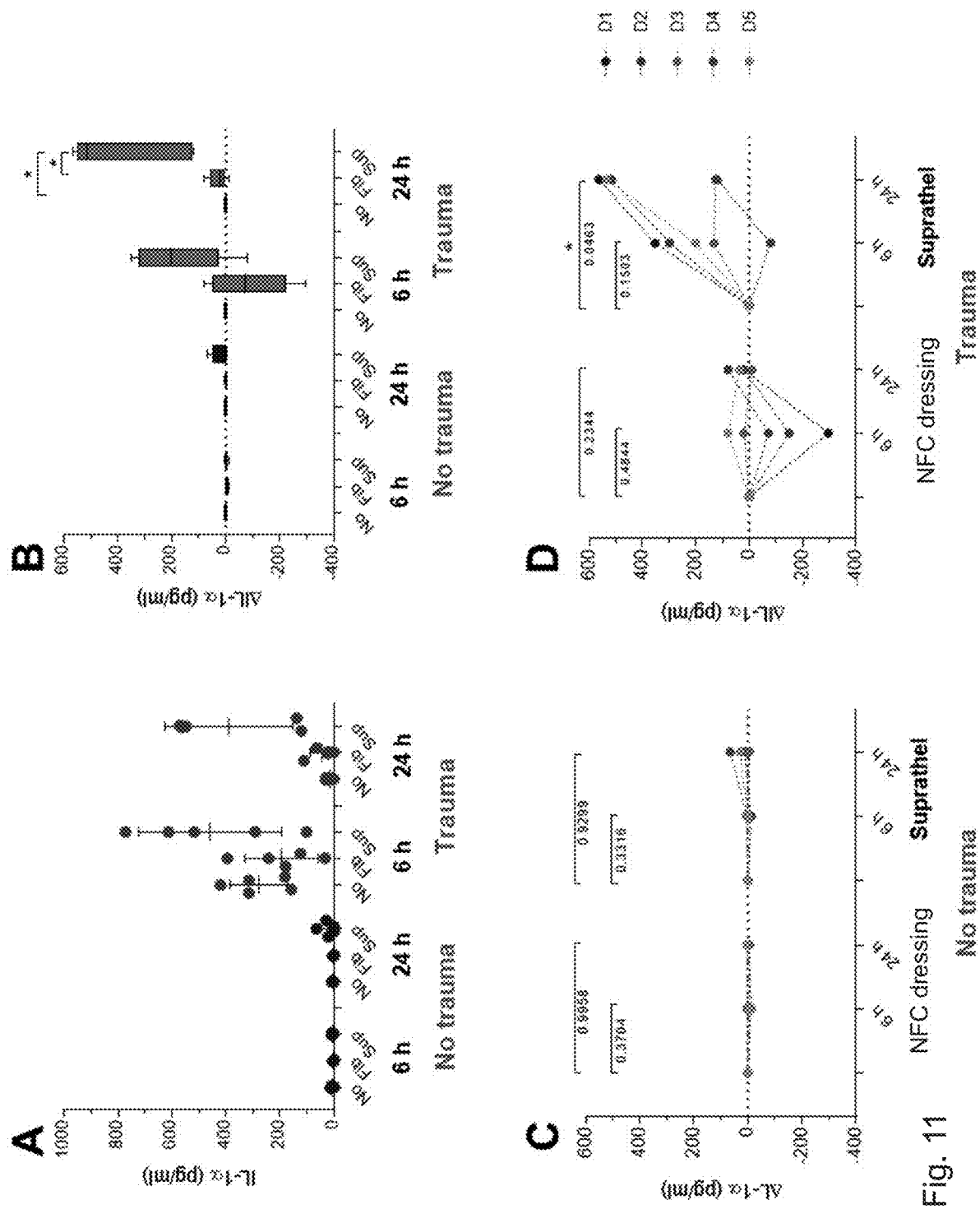
FIG. 11 shows levels of IL-1α in dialysates. A) Absolute levels of IL-1α (n=5 donors). Depicted is mean±SD (see FIG. S1 for individual donors). B) Relative levels of IL-1α (ΔIL-1α) in response to incubation of skin specimens with/without trauma with NFC dressing- or Suprathel®-treatment, respectively. NFC dressing and Suprathel® samples are normalized by subtracting no dressing-control levels for each time point. Boxes represent 25%-75% percentiles and whiskers represent min-max. C) and D) show ΔIL-1α plotted relative to the two time points, 6 h and 24 h, without trauma (C) and with trauma (D). *P<0.05, Tukey's multiple comparisons test. No=No dressing, Fib=NFC dressing, Sup=Suprathel®.

Dialysate levels of IL-1α were found to increase in response to trauma (FIG. 11A, comparing no dressing at 6 hours, with and without trauma). Without dressing treatment, the levels of IL-1α were found to spontaneously decrease over time in skin samples with trauma (FIG. 11A, comparing no dressing samples at 6 hours and 24 hours). Suprathel® mediates a relative increase in IL-1α compared to the no dressing-control, which results in an elevated IL-1α response over both time points (FIGS. 11B and 11D, only significant at 24 hours). There was also a slight elevation in IL-1α levels in samples without trauma, although not statistically significant (FIG. 11C). NFC dressing, on the other hand, seems to mediate a slight decrease in the IL-1α response at the early time point (large variation between donors, not significant), while resulting in a slight upregulation at the later time point, though not significant (FIG. 11D).

IL-6 Levels in Dialysates

Figure 12:
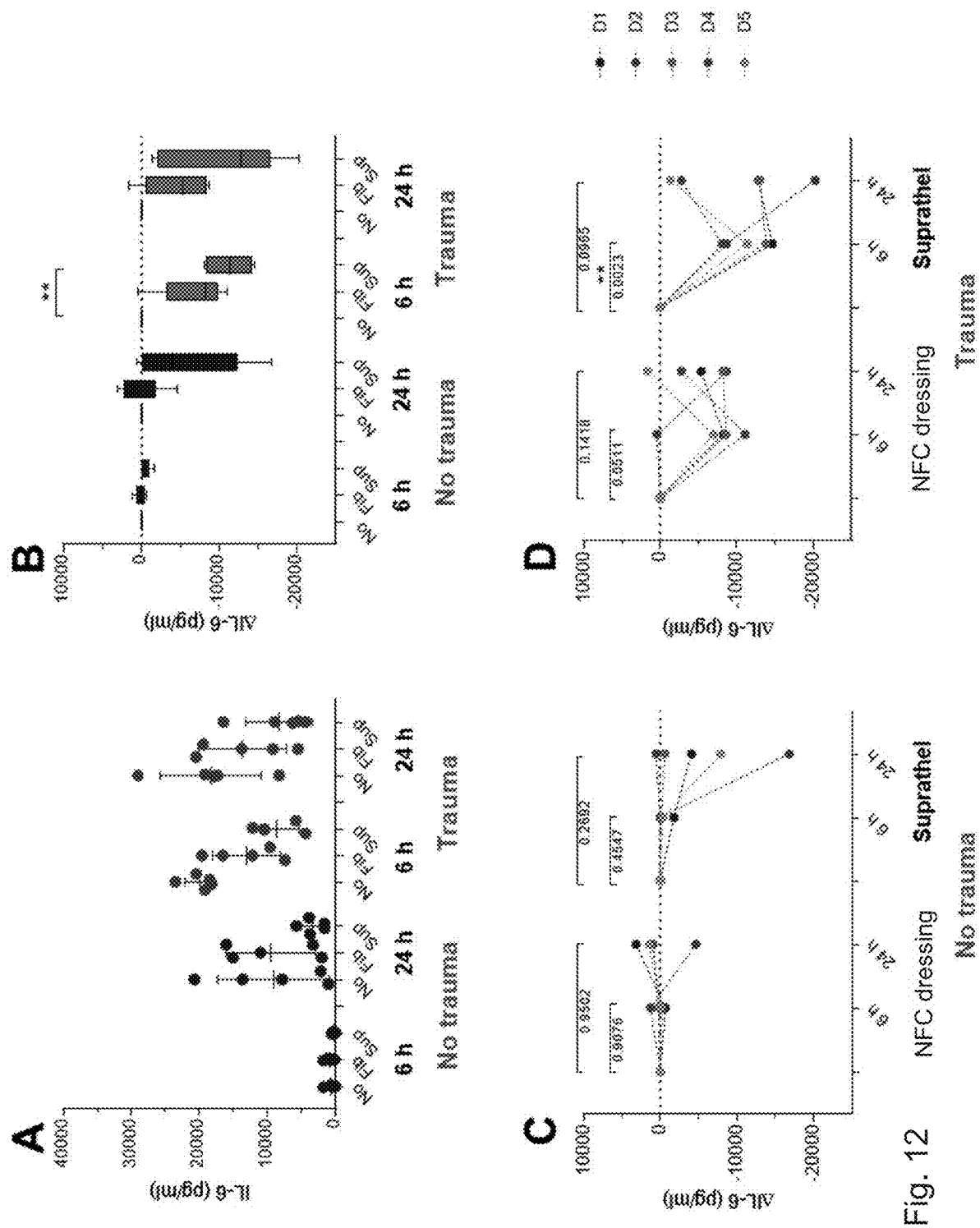
FIG. 12 shows levels of IL-6 in dialysates. A) Absolute levels of IL-6 (n=5 donors). Depicted is mean±SD (see FIG. S2 for individual donors). B) Relative levels of IL-6 (ΔIL-6) in response to incubation of skin specimens with/without trauma with NFC dressing- or Suprathel®-treatment, respectively. NFC dressing and Suprathel® samples are normalized by subtracting no dressing-control levels for each time point. Boxes represent 25%-75% percentiles and whiskers represent min-max. C) and D) show ΔIL-6 plotted relative to the two time points, 6 h and 24 h, without trauma (C) and with trauma (D). **P<0.005, Tukey's multiple comparisons test. No=No dressing, Fib=NFC dressing, Sup=Suprathel®.

Dialysate levels of IL-6 were found to increase in response to trauma (FIG. 12A, comparing no dressing at 6 hours with and without trauma). Background levels (no dressing-control samples) of IL-6 increased from 6 hours to 24 hours across all donors (FIG. 12A, comparing no trauma-controls at 6 hours and 24 hours). Suprathel® induces a decrease in IL-6 levels in skin specimens subjected to trauma, which is observed across all donors and at both time points, but only significantly after 6 hours (FIGS. 12B and 12D, comparing no dressing-controls to Suprathel®-treated skin specimens). Furthermore, Suprathel® blocked the upregulation of IL-6 observed in the no trauma-control specimens, however, this was not statistically significant (FIGS. 12B and 12C). NFC dressing-treatment seemed to mediate a decrease in IL-6 when compared to the no dressing-control (in skin specimens subjected to trauma), however, not to the same degree as Suprathel® and this trend was not statistically significant (FIGS. 12B and 12D).

MIF Levels in Dialysates

Figure 13:
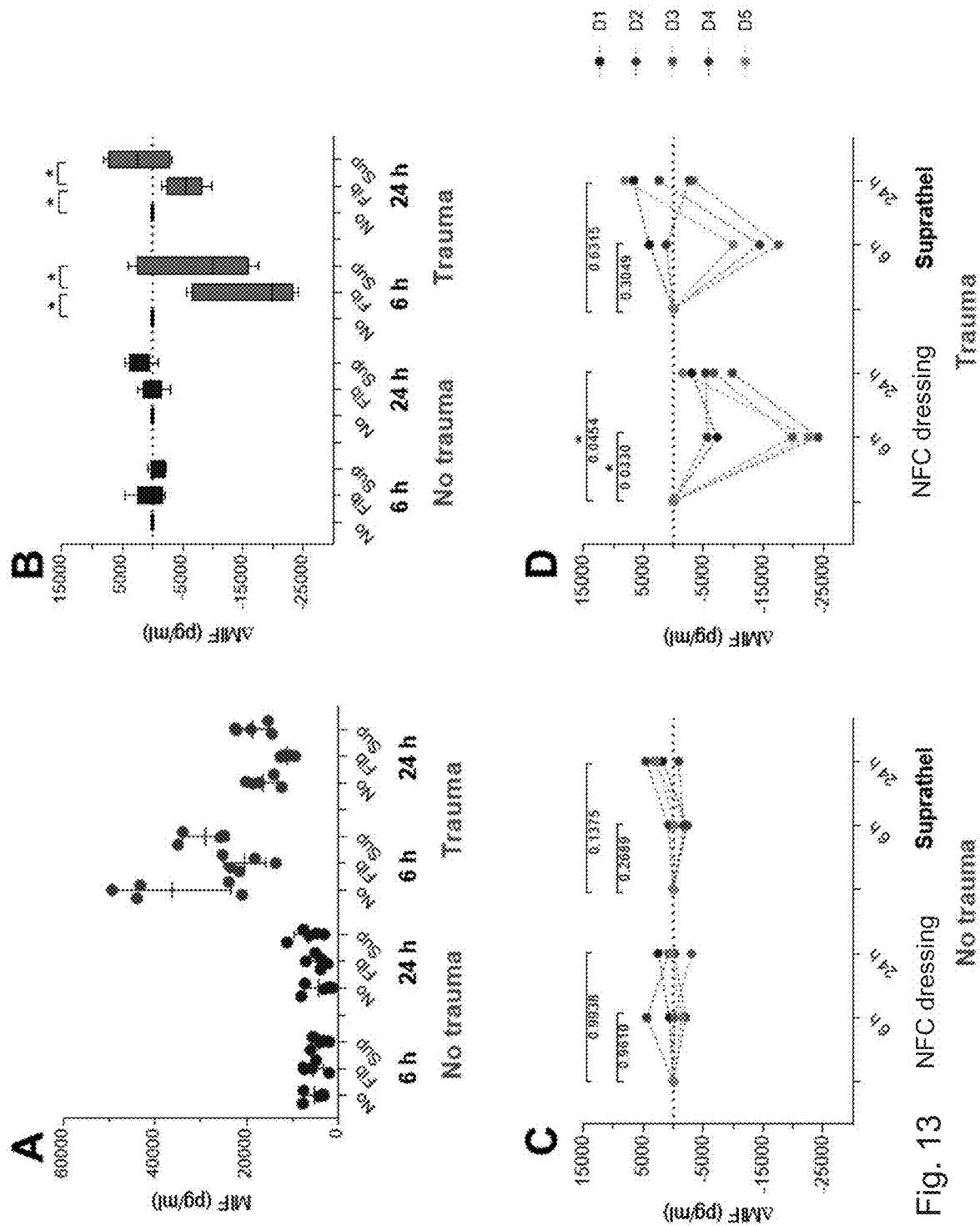
FIG. 13 shows levels of MIF in dialysates. A) Absolute levels of MIF (n=5 donors). Depicted is mean±SD (see FIG. S3 for individual donors). B) Relative levels of MIF (ΔMIF) in response to incubation of skin specimens with/without trauma with NFC dressing- or Suprathel®-treatment, respectively. NFC dressing and Suprathel® samples are normalized by subtracting no dressing-control levels for each time point. Boxes represent 25%-75% percentiles and whiskers represent min-max. C) and D) show ΔMIF plotted relative to the two time points, 6 h and 24 h, without trauma (C) and with trauma (D). *P<0.05, Tukey's multiple comparisons test. No=No dressing, Fib=NFC dressing, Sup=Suprathel®.

Dialysate levels of MIF are strongly upregulated in response to trauma (FIG. 13A, comparing no dressing-control specimens with and without trauma at 6 and 24 hours, respectively). NFC dressing mediates a decrease of MIF at both the early and the late time point (FIGS. 13B and 13D, compared to no dressing-controls at 6 hours and 24 hours). Suprathel® may also decrease levels of MIF, but to a lesser extent than NFC dressing, and this is not significant when compared to the no dressing-controls (FIGS. 13B and 13D).

NAP-2 Levels in Dialysates

Figure 14:
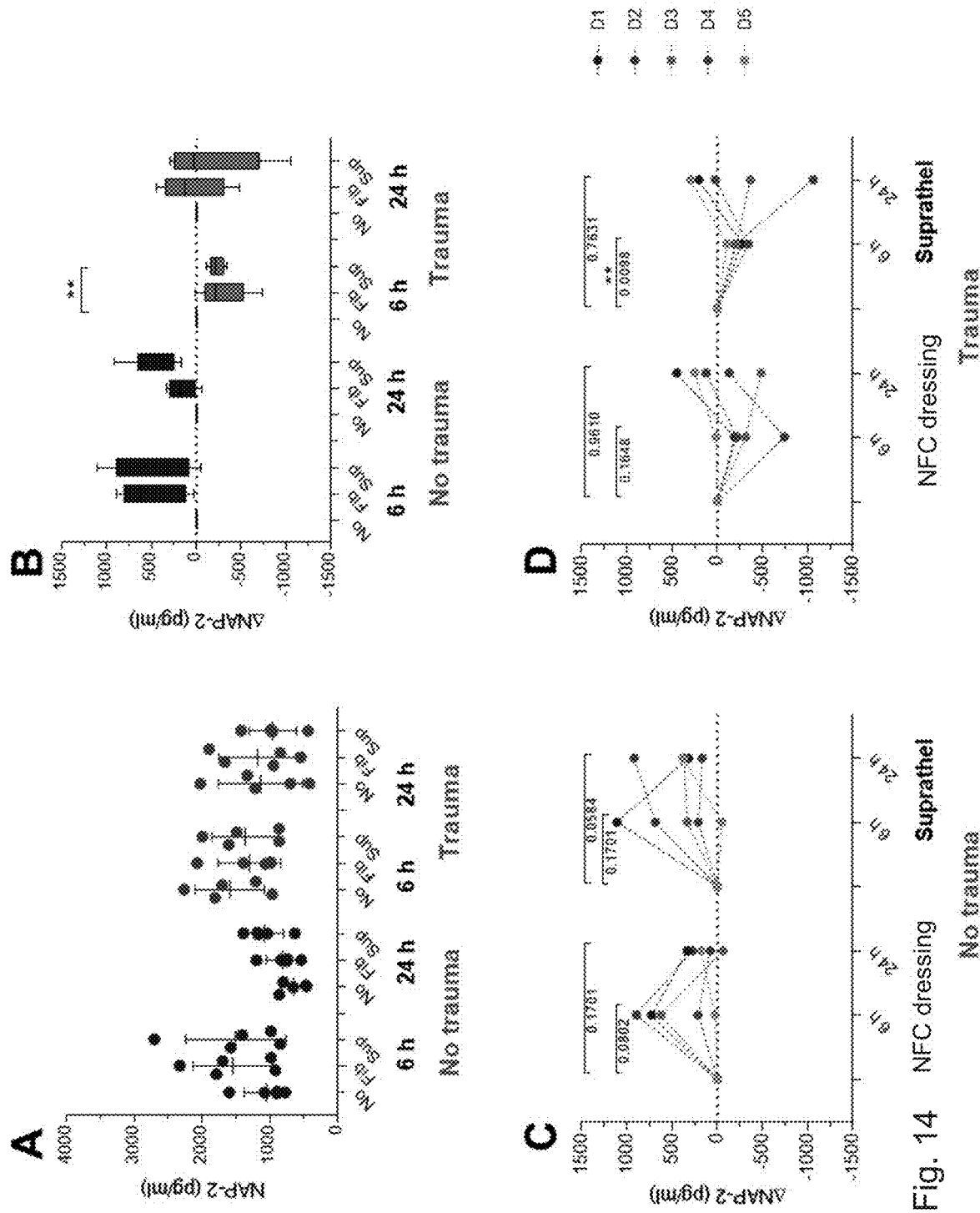
FIG. 14 shows levels of NAP-2 in dialysates. A) Absolute levels of NAP-2 (n=5 donors). Depicted is mean±SD (see FIG. S4 for individual donors). B) Relative levels of NAP-2 (ΔNAP-2) in response to incubation of skin specimens with/without trauma with NFC dressing- or Suprathel®-treatment, respectively. NFC dressing and Suprathel® samples are normalized by subtracting no dressing-control levels for each time point. Boxes represent 25%-75% percentiles and whiskers represent min-max. C) and D) show ΔNAP-2 plotted relative to the two time points, 6 h and 24 h, without trauma (C) and with trauma (D). **P<0.005, Tukey's multiple comparisons test. No=No dressing, Fib=NFC dressing, Sup=Suprathel®.

Background levels of NAP-2 seem to decrease over time (FIG. 14A, no dressing-controls). NAP-2 levels exhibit a large variation across donors. Incubation with Suprathel® for 6 hours mediated a significant decrease in NAP-2 levels (FIGS. 14B and 14D, comparing Suprathel® treatment to the no dressing-control). On average, incubation with NFC dressing was found to reduce levels of NAP-2 compared to no dressing-controls, however, this was not significant due to a larger variation between donors.

5.3 Main Phase 2

IL-1α Levels in NFC Dressing Samples

Figure 15:
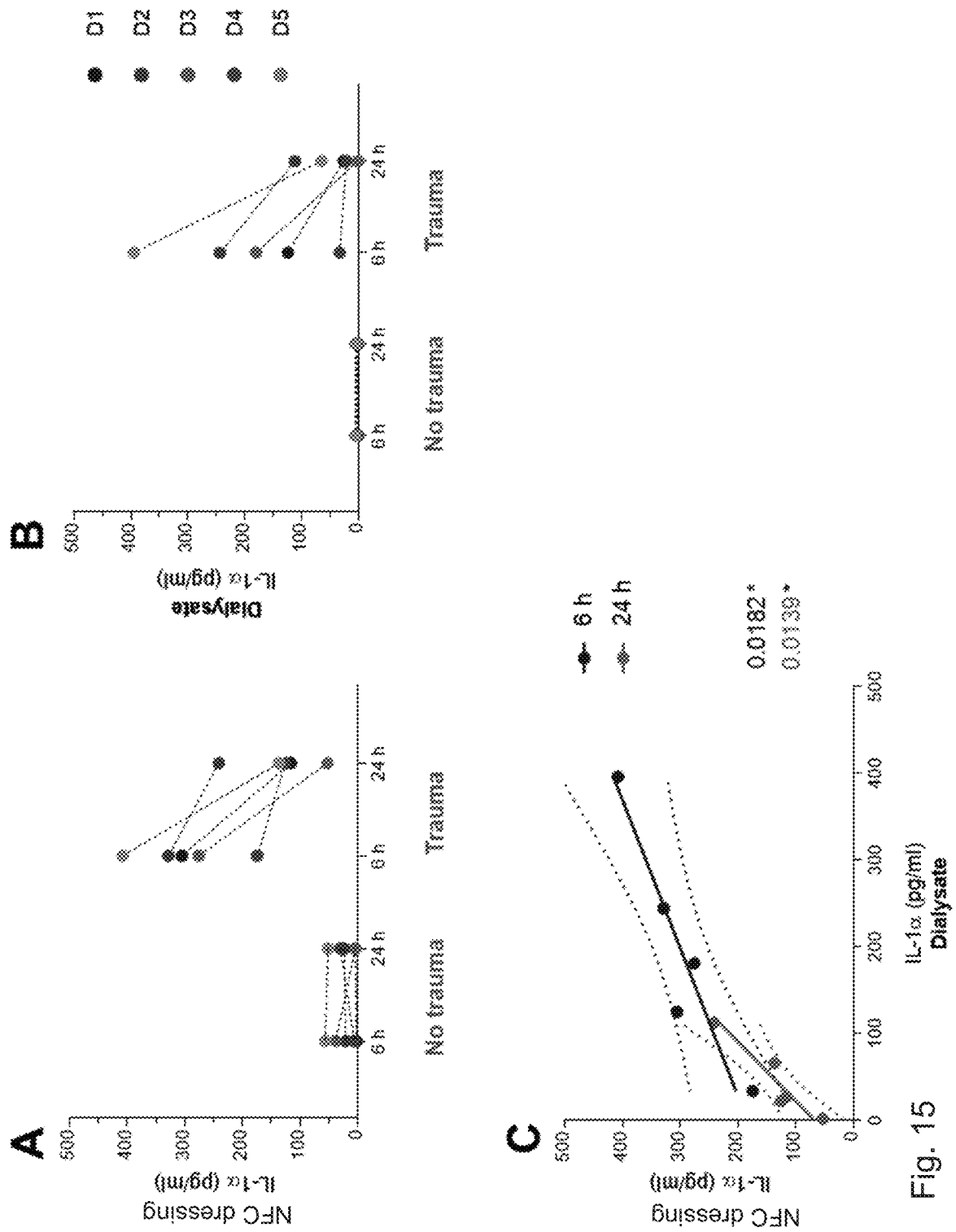
FIG. 15 shows levels of IL-1α in NFC dressing and dialysates. A) Trend plot of IL-1α levels recovered from GrowDase-treated NFC dressing after incubation on human skin samples for 6 and 24 hours (n=5 donors). Depicted are data from individual donors. B) Trend plot of dialysate levels of IL-1α in the corresponding NFC dressing samples. C) Correlation plot comparing IL-1α levels measured in NFC dressing to the corresponding dialysate levels. The lines represent linear regressions at the two time points. Dotted lines represent the 95% confidence intervals. Values represent corresponding P values based on a Pearson correlation, *P<0.05.

GrowDase™-facilitated degradation of NFC dressing mediated a release of IL-1α from NFC dressing incubated on top of skin specimens subjected to trauma after both 6 and 24 hours incubation (FIG. 15A). Low levels of IL-1α were detected in some NFC dressing pieces incubated on top of no trauma-control specimens (FIG. 15A). IL-1α levels decreased over time in both dialysates and NFC dressing (FIGS. 15A and 15B). A statistically significant correlation was found between the levels of IL-1α in dialysates and in NFC dressing samples from skin specimens subjected to trauma after incubation for both 6 hours and 24 hours (FIG. 15C).

IL-6 Levels in NFC Dressing Samples

Figure 16:
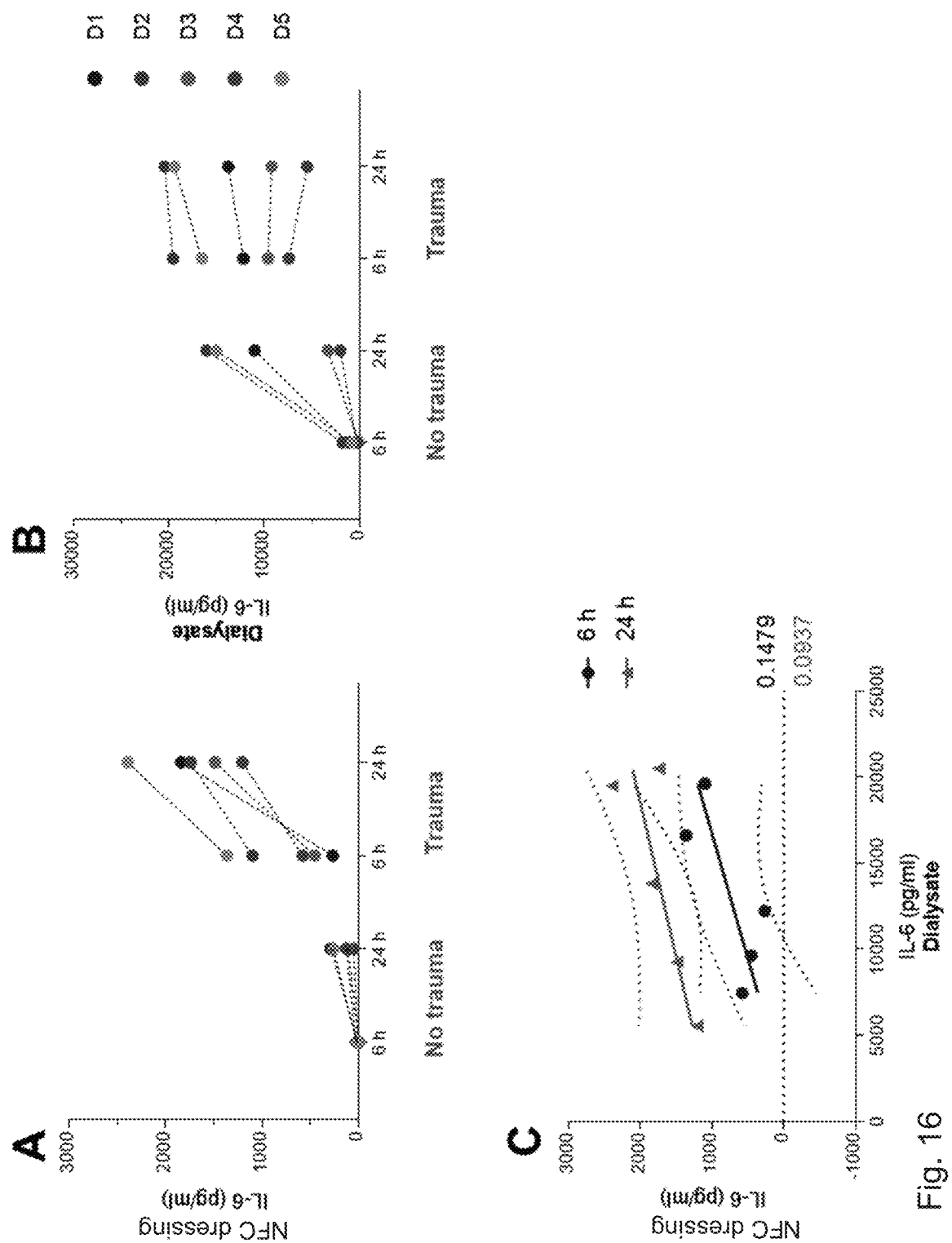
FIG. 16 shows levels of IL-6 in NFC dressing and dialysates. A) Trend plot of IL-6 levels recovered from GrowDase-treated NFC dressing after incubation on human skin samples for 6 and 24 hours (n=5 donors). Depicted are data from individual donors. B) Trend plot of dialysate levels of IL-6 in the corresponding NFC dressing samples. C) Correlation plot comparing IL-6 levels measured in NFC dressing to the corresponding dialysate levels. The lines represent linear regressions at the two time points. Dotted lines represent the 95% confidence intervals. Values represent corresponding P values based on a Pearson correlation.

GrowDase™-treatment of NFC dressing mediated a release of IL-6 from pieces incubated on top of skin specimens subjected to trauma after both 6 and 24 hours incubation (FIG. 16A). Low levels of IL-6 were also observed in NFC dressing incubated on top of no trauma-control specimens for 24 hours. IL-6 levels were found to increase over time in NFC dressing, however, this trend was only seen in dialysates obtained from no trauma-control specimens and not in dialysates from skin specimens subjected to trauma (FIGS. 16A and 16B). There seems to be a trend towards a positive linear relationship between the IL-6 levels in NFC dressing and dialysate samples, however, this is not statistically significance according to the Pearson correlation (FIG. 16C).

MIF Levels in NFC Dressing Samples

Figure 17:
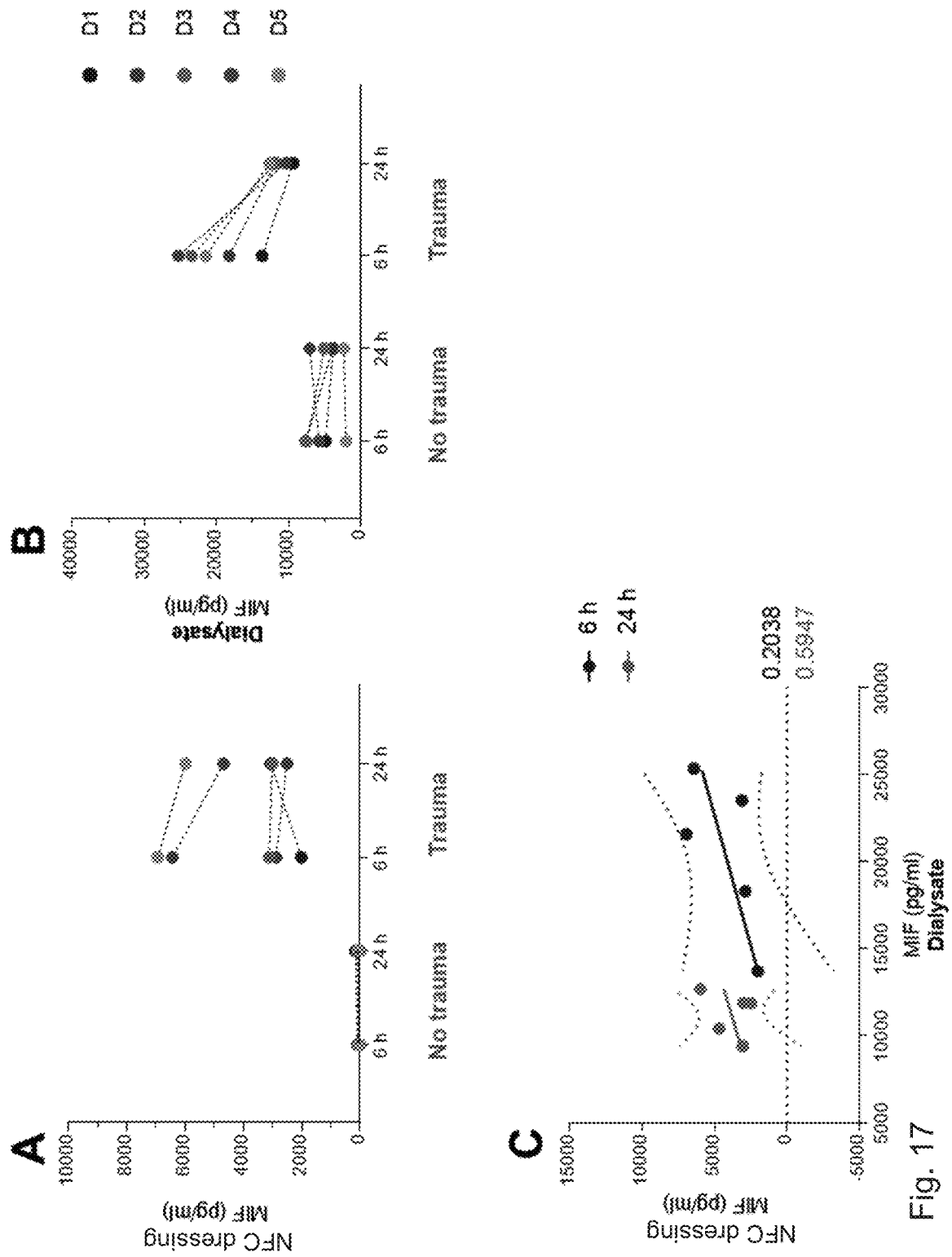
FIG. 17 shows levels of MIF in NFC dressing and dialysates. A) Trend plot of MIF levels recovered from GrowDase-treated NFC dressing after incubation on human skin samples for 6 and 24 hours (n=5 donors). Depicted are data from individual donors. B) Trend plot of dialysate levels of MIF in the corresponding NFC dressing samples. C) Correlation plot comparing MIF levels measured in NFC dressing to the corresponding dialysate levels. The lines represent linear regressions at the two time points. Dotted lines represent the 95% confidence intervals. Values represent corresponding P values based on a Pearson correlation.

MIF was recovered from NFC dressing incubated on top of skin specimens subjected to trauma (FIG. 17A), but not from NFC dressing incubated on top of no trauma-control specimens. This correlates with the increase in dialysate MIF levels from skin specimens with trauma relative to the no trauma-controls (FIG. 17B). Dialysate levels of MIF decrease from 6 to 24 hours with trauma (FIG. B), which is also seen in NFC dressing samples from 4/5 donors (FIG. 17A). MIF was present in dialysates from the no-trauma control skin specimens, but no MIF was detected in the corresponding NFC dressing samples (FIGS. 17A and 17B). We found a positive linear relationship between MIF levels in NFC dressing and dialysate samples, however, this was not significant according to the Pearson correlation performed for both time points (FIG. 17C).

NAP-2 Levels in NFC Dressing Samples

Figure 18:
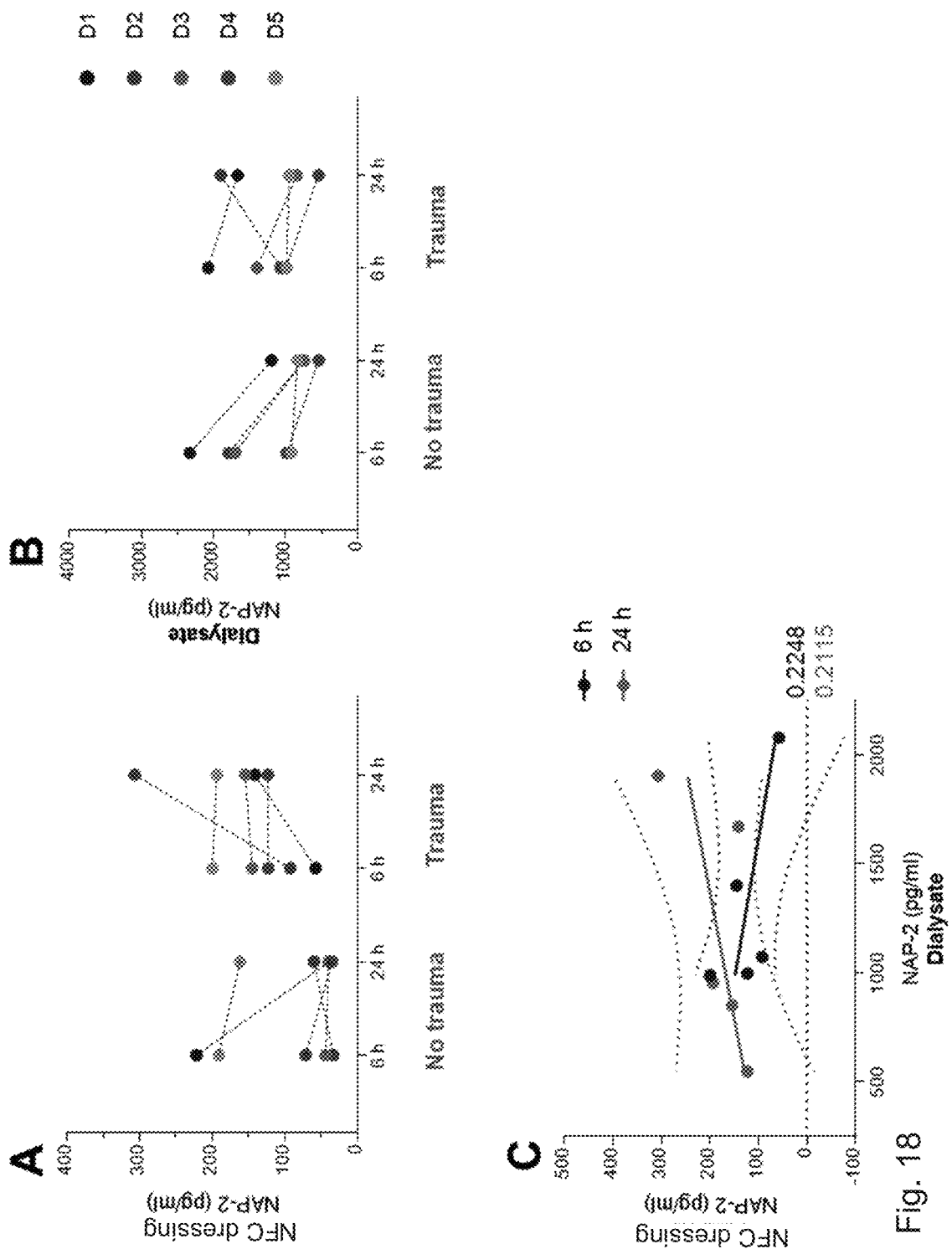
FIG. 18 shows levels of NAP-2 in NFC dressing and dialysates. A) Trend plot of NAP-2 levels recovered from GrowDase-treated NFC dressing after incubation on human skin samples for 6 and 24 hours (n=5 donors). Depicted are data from individual donors. B) Trend plot of dialysate levels of NAP-2 in the corresponding NFC dressing samples. C) Correlation plot comparing NAP-2 levels measured in NFC dressing to the corresponding dialysate levels. The lines represent linear regressions at the two time points. Dotted lines represent the 95% confidence intervals. Values represent corresponding P values based on a Pearson correlation.

NAP-2 was recovered from NFC dressing incubated on top of skin samples with and without trauma for both time points (FIG. 18A). The levels of NAP-2 in NFC dressing were generally higher when incubated on top of skin samples subjected to trauma (FIG. 18A, except for donor 1 after 6 hours of incubation). While there is a tendency to a decrease in dialysate levels of NAP-2 over time (FIG. 18B), NAP-2 levels in NFC dressing samples appear to either remain unchanged or increase over time, with the exception of donor 1 (FIG. 18A). After 6 hours of incubation we found a negative linear relationship between NFC dressing levels and the corresponding dialysate levels, whereas a positive linear relationship was found after 24 hours. None of these correlations were statistically significant.

Discussion

In the pre-phase we found that seven out of the eight biomarkers in the panel were successfully recovered by the microdialysis probes. Despite being unable to quantify the relative recovery of MIF due to high background levels of the cytokine in thawed skin, we could conclude that it readily passed the microdialysis membrane. IFN-γ was the only biomarker which was not recovered in the skin reservoir model. However, this finding is consistent with the very low in vitro recovery of IFN-γ described in the literature (Ao and Stenken 2006).

IL-1α, IL-6, MIF and NAP-2 were the only biomarkers detectable in viable skin, as seen from the pre-phase results, which is why these were the main focus of subsequent experiments.

In the main phase we found IL-1α to be significantly upregulated after 24 hours in response to Suprathel®-treatment, whereas IL-6 was significantly decreased after 6 hours incubation with Suprathel®. NFC dressing mediated a similar trend with IL-6, however, less pronounced and not statistically significant. Only MIF was significantly changed in response to NFC dressing-treatment with a statistically significant decrease after both 6 and 24 hours. NAP-2 levels were significantly lower after 6 hours of incubation with Suprathel®.

To our surprise, we found that the biomarkers measured in the dialysates were also detectable in NFC dressing after degradation with GrowDase. Thus, we speculate that NFC dressing may exert its effect on the wound healing process by acting as a biomarker reservoir. The reservoir may either be passive, only removing fluid and mediators from the tissue, or be a functional/active reservoir in terms of being able to facilitate a two-way diffusion with uptake and delivery of active mediators to and from the tissue over time. It is possible that biomarkers taken up by NFC dressing are somehow stabilized in the hydrogel layer and may thus have a different turnover compared to the tissue environment.

It is well known that individual molecules have different physiochemical properties, which is supported by the results, as it seems that the biomarkers have distinct diffusion characteristics and/or stability in the tissue compared to the hydrogel layer of NFC dressing: IL-1α was found to be present in NFC dressing incubated on control skin specimens with no trauma, but the cytokine was not detected in the corresponding dialysates. Conversely, MIF was absent in NFC dressing incubated on skin with no trauma, whereas it was found in the matching dialysates.

The lack of IL-1α in dialysates from skin specimens without trauma, while there are measurable amounts in the corresponding NFC dressing samples, could indicate that tissue IL-1α is quickly degraded, as opposed to IL-1α in the dressing. It is also possible that IL-1α is simply removed from the tissue through a one-way diffusion into the dressing where it is retained.

Regarding MIF, this cytokine might be more stable in NFC dressing within the first 24 hours compared to in the tissue, as tissue levels decrease over time, whereas NFC dressing levels do not. One might hypothesize that NFC dressing is saturated with MIF after 6 hours, which would explain why NFC dressing levels are comparable at both time points investigated. The lack of MIF in the NFC dressing incubated on specimens without trauma, while there is measurable MIF in the dialysate, could indicate that diffusion of MIF into NFC dressing requires a disruption of the skin barrier.

The increase in NFC dressing levels of IL-6 over time, which is not seen in the dialysates, as they appear to be constant, point towards an accumulation of IL-6 in NFC dressing with time. Another possible explanation is that diffusion of IL-6 into NFC dressing is delayed and thus does not reflect the tissue concentrations at early time points. The turnover might also differ in the skin compared to the dressing, with a lower degree of degradation in the dressing compared to the tissue.

No clear trend with respect to NAP-2 levels in NFC dressing was observed.

One of the main features of NFC dressing is the formation of a hydrogel layer due to the NFC content in the dressing. This helps retain a moist wound environment and removes excessive exudate. Furthermore, the dressing itself functions as a physical barrier against the surroundings, thus preventing infections. In this sense, occlusion is both beneficial and necessary for efficient wound healing, but as mentioned earlier, excessive occlusion can have negative effects on e.g. IL-6 induction. Macroscopically, the NFC dressing appears less occlusive compared to Suprathel® when the two dressings were inspected and handled in the experimental setups. Combining this observation with the fact that both Suprathel® and NFC dressing reduced IL-6 compared to the no dressing-control, and Suprathel® having a more pronounced effect, corroborates the hypothesis that NFC dressing is less occlusive. It seems that NFC dressing allows a more efficient exchange of gasses while facilitating a beneficial moist environment, which might explain some of the positive effects of NFC dressing on wound healing.

Conclusion

This study demonstrates how human ex vivo skin combined with the microdialysis technique can be used as a preclinical model to investigate cutaneous wound healing in the early phase and the effect of different wound dressings, in this case NFC dressing and Suprathel®.

It was found out that four out of the eight biomarkers in the biomarker panel were efficiently sampled from skin specimens subjected to trauma and some of these biomarkers were significantly affected by skin incubation with the dressings.

NFC dressing only influenced levels of MIF in a statistical significant manner as seen by a decrease after 6 and 24 hours of incubation with NFC dressing. Suprathel®, on the other hand, was found to mediate a statistical significant decrease in levels of IL-6 and NAP-2 after 6 hours, whereas IL-1α was significantly upregulated after 24 hours in response Suprathel®-treatment.

Overall, there appears to be a positive relationship between the levels of cytokines recovered from NFC dressing and the levels measured in the dialysates, however, this was only statistically significant for IL-1α. Still, the ability of NFC dressing to contain cytokines may be an important finding.

Example 2

It was found out that the NFC dressing can bind different soluble factors relevant to the wound healing process, and found in wound fluid. Therefore the level of retention of TNFa, IL-10 and TGFb1 to the NFC dressing matrix in comparison to media and NFC cloth (no NFC content) was investigated. Purified growth factors with demonstrated stability for up to 4 hours in culture were incubated with RPMI media, NFC dressing cloth and NFC dressing for 1 and 4 h. Free cytokine was measured by ELISA and compared to the 1 h media control. No significant degradation or loss of cytokine was seen in the media controls over the 4 h incubation time. NFC dressing significantly reduced the level of free TNFa compared to the cloth at 4 h, indicating that the NFC component may be able to retain cytokines within the gel. Levels of IL-10 were significantly depleted by exposure to the cloth and NFC dressing at both 1 and 4 h. The same effect was also seen for TGFb1 at 4 hrs, with the highest effects always seen in the NFC dressing matrix compared to cloth alone or media. Taken together these data demonstrate that NFC dressing is able to absorb active biomolecules from the wound environment.

Example 3

The study results show that NFC dressing is a favorable product for wound care. The data demonstrates that NFC is an unique material to be utilized in a wound healing dressing as described herein with properties to actively participate in enhancing innate wound repair responses. It was shown that NFC dressing potentially reduces oxidative stress potential in peripheral immune cells which positively contributes to wound healing process.

Peripheral blood mononuclear cells (PBMCs) from whole blood were isolated and incubated with NFC dressing+/− LPS for 24 hours, with the production of reactive oxygen species (ROS) measured at multiple time points. The aim of these investigations was to establish if (a) the NFC dressing matrix would be recognized as foreign material and trigger an oxidative stress reaction and (b) if NFC dressing binds LPS to enhance any baseline level of ROS production by the PBMCs. ROS production was assessed by evaluating the conversion of H2DCFDA into the fluorescent compound DCF (cleaved to its fluorescent form by ROS) using fluorimetry. Data indicate that base levels of oxidative stress in the RPMI controls were significantly higher than in the NFC dressing samples at 1 h. Although not statistically significant, both NFC dressing and NFC dressing+LPS demonstrated lower ROS readouts than their respective controls at multiple time points. These data potentially indicate that NFC dressing, perhaps through the binding of soluble factors released by the PBMCs, protect the cells from oxidative stress. It can be concluded that NFC dressing does not exert a stress response as a foreign material on PBMCs.

Example 4

In this example the physical properties of the present NFC wound dressings are characterized and compared with the measured properties of other development versions. In total of nine different standard testing methods and internal methods were used to characterize the samples.
Materials and Methods
Samples Main motivation guiding the sample selection was the will to evaluate samples that were produced by different methods or using slightly different raw material composition. According to these criteria six wound dressings and one untreated nonwoven were selected. These samples represent different NFC wound dressing development versions and the individual raw materials used for manufacturing. All the samples were steam sterilized according to typical sterilization procedure (121.6° C.; 20 min) before the analysis. The nominal grammage of the nonwoven used in the medical products was about 45 g/m². The essential sample information is presented in Table 2.

TABLE 2

The samples that were analyzed during the study.

| Sample name | Production batch | Method of manufacturing | Description |
|---|---|---|---|
| NFC dressing | 1-2018-AA | Machine produced | Commercial nonwoven + NFC, Steam sterilized |

TABLE 2-continued

The samples that were analyzed during the study.

| Sample name | Production batch | Method of manufacturing | Description |
|---|---|---|---|
| NFC dressing Type 4 | BA | Manual | Commercial nonwoven + NFC, Steam sterilized |
| HW-NFC dressing | 12-2018-AD | Machine produced | High weight NFC dressing: Commercial nonwoven + NFC, Steam sterilized |
| LW-NFC dressing | 12-2018-AA | Machine produced | Low weight NFC dressing: Commercial nonwoven + NFC, Steam sterilized |
| Anionic NFC dressing | CD | Manual | Commercial nonwoven + anionic NFC, Steam sterilized |
| NFC-Film | BV | Filtration | 100% NFC film, Steam sterilized |
| Commercial nonwoven | — | — | Commercial Genesis nonwoven |

Analytical Methods

All the methods selected for this study are presented in Table 3.

TABLE 3

Analytical methods used to characterize the physical properties of the samples.

| Property | Method | Unit |
|---|---|---|
| Grammage | ISO 536 | g/m² |
| Air permeability | ISO 5636-3 | ml/min |
| Thickness | ISO 534 | µm |
| Density | ISO 534 | g/cm³ |
| Area change when wetted | Internal | % |
| Area change when dried | Internal | % |
| Fluid retention | Internal | $g_{H2O}/g_{NFC}$ |
| Moisture vapor transmission rate | SFS-EN-13726-2 | g · m²/24 h |
| Stereo microscopy | Internal | — |

The method described by EN 13726-1 standard: "Test methods for primary wound dressings. Part 1: Aspects of absorbency" was followed when determining the free swelling absorptive capacity of the samples. In short, the method is based on weighting the sample before and after a 30 minute soak in excess of physiological test solution at the temperature of 37° C. The absorptive capacity is then calculated as g/100 cm². Physiological test solution containing 142 mmol of sodium chloride and 2.5 mmol of calcium chloride was used and the measurements were done under the conditions defined by the standard test method EN 13726-1.

Fluid retention of the dressings was measured using internal method based on the original method presented in Mennini, N., et al. "Quality of wound dressings: a first step in establishing shared criteria and objective procedures to evaluate their performance." Journal of wound care 25.8 (2016): 428-437. In this method a free swelling absorption capacity sample was sandwiched between two wire cloths and placed on a piece of absorbent paper. Then a plexiglass tablet was placed on top of the sample applying a pressure of 40 mmHg. After 30 minutes the weight was removed, and the sample was weighted. The fluid retention was calculated based on the observed weight difference and reported as the percent of fluid remaining.

The area changes of the wound dressings when wetted and dried were determined at the same time with the free swelling and fluid retention tests. These internal methods use the simple principle of measuring the wound dressing dimensions before and after the free swelling test and once more after drying the sample in a laboratory oven overnight at 60° C. The changes in area are reported as perceptual change compared to the original dry sample (e.g. −4%=4% shrinkage in area). If the observed changes in area are small, results should be considered approximate as the dimensions (x and y) are measured using a ruler which has limited accuracy. It is also possible that the changes in wound dressing dimensions are uneven and therefore hard to measure accurately.

Moisture vapor transmission rate (MVTR), SFS-EN-13726-2 standard method, measures the rate that water vapor permeates through a film-like wound dressing. In this method the sample is placed on a flanged sample cup filled with purified water and secured in place with a lid. The lid has a 10 cm$^2$ hole which is the only way water vapor can evaporate through the wound dressing. The sample cup (+water and the sample) is weighted and placed in a climate chamber (37° C., RH %<20) for 18 to 24 hours. Finally, the cup is reweighted and the MVTR is calculated as g/m$^2$/24 h based on the weight loss.

Deviations from the Standard Methods

For determination of free swell absorptive capacity only 5 replicates instead of 10 were measured due to limited sample material. There were no other deviations from the standard test method EN 13726-1.

Results

The averaged results for this comparison study are compiled in Table 4. In the following subchapters some selected properties and the corresponding results are discussed more in detail.

ings (type 4) fulfilled the specifications that are set for sterilized product (<1000 ml/min and 50-55 g/m$^2$). However, manually produced NFC wound dressings had slightly higher grammage and air permeability than machine produced NFC wound dressings. Air permeability results are typically used indirectly to monitor the distribution and especially the evenness of the NFC coating. Here the lower air permeability result (67 ml/min) of machine produced NFC wound dressings would suggest that the NFC evenness is on a same level or better than manually produced NFC wound dressings (624 ml/min).

Other samples gave quite logical values as the higher grammage value mostly implied lower air permeability. The two extremes were the samples that represented the individual raw materials NFC and nonwoven. NFC-film was practically impermeable to air whereas Commercial nonwoven exceeded the method's measurement range maximum and gave the value 8820 ml/min. The high grammage result 53.3 g/m$^2$ of LW-NFC dressing (12-2018-AA) was somewhat unexpected as previous measurements in 12/2018 gave averaged grammage value of 50.8 g/m$^2$.

Figure 22:
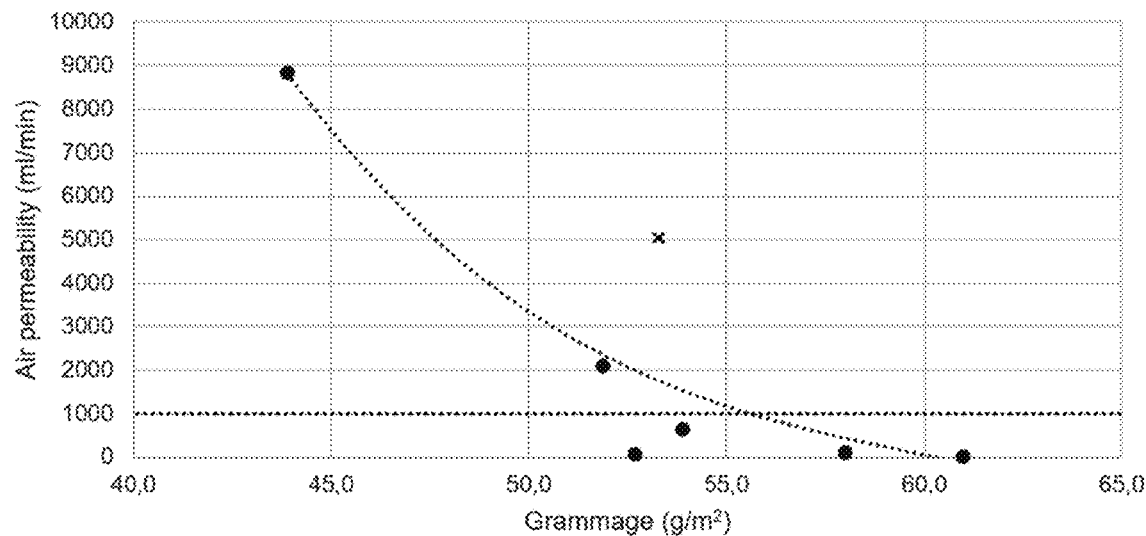
FIG. 22 shows visual presentation of grammage and air permeance relation. The line describes the upper air permeability specification limit and the curve is a polynomial fit of the measured data.

FIG. 22 gives a simple visual presentation of the grammage and air permeability relation using the data summarized in Table 2. The horizontal line presents the upper specification limit of air permeability and the curve is a rough polynomial fit to the data. Even though the measured samples are by many terms different to each other, this polynomial fit gives some indication about the probability to hit the air permeability target as grammage is increased. The LW-NFC dressing data point is marked with a cross because of the erroneously high grammage value but it's not excluded here from the data.

TABLE 4

Compiled and averaged results for the studied samples.

| Measured physical property | NFC dressing | NFC dressing Type 4 | HW-NFC dressing | LW-NFC dressing | Anionic NFC dressing | NFC-Film | Commercial nonwoven |
|---|---|---|---|---|---|---|---|
| Grammage (g/m$^2$) | 52.7 | 53.9 | 58.0 | 53.3 | 51.9 | 61.0 | 43.9 |
| Air permeance (ml/min) | 67 | 624 | 73 | 5038 | 2076 | 0 | 8820/max. |
| Bulking thickness (μm) | 239 | 213 | 253 | 228 | 205 | 66 | 227 |
| Apparent bulk density (kg/m$^3$) | 220 | 253 | 229 | 234 | 253 | 924 | 194 |
| Bulk (cm$^3$/g) | 4.55 | 3.95 | 4.36 | 4.27 | 3.96 | 1.08 | 5.16 |
| Area change when wetted (%) | 2.0 | 2.4 | 2.0 | 2 | 2.0 | 5.7 | 0.4 |
| Area change when dried (%) | −2.8 | −1.6 | −1.2 | −0.5 | 0.0 | 0.0 | 0.4 |
| Fluid retention (%) | 22.7 | 24.1 | 23.8 | 14.8 | 28.3 | 18.1 | 7.4 |
| MVTR (g/m$^2$ * 24 h) | 4486 | 4592 | 4762 | 5275 | 4769 | 2643 | 5887 |

Air Permeability and Grammage

Figure 23:
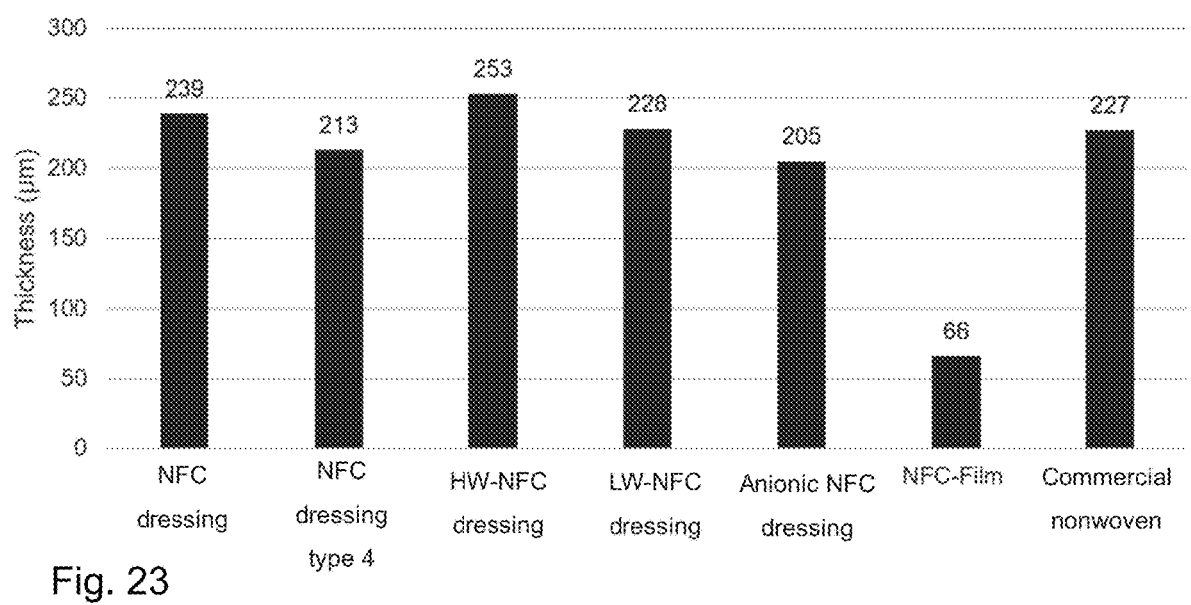
FIG. 23 shows a column chart for comparison of sample thickness (μm).

The results for grammage and air permeability, that are used also as standard quality control measures, gave mostly results that were expected. Both the machine produced NFC wound dressings and manually produced NFC wound dress- Physical Dimensions Basic dimensions like bulking thickness and bulk density gave mostly values as expected but also showed some surprising behavior. Measured sample thicknesses are compared in FIG. 23. The NFC film was found to be thinnest and had clearly the highest density (924 kg/m$^3$) of all the samples. In terms of thickness the machine produced NFC dressing samples (NFC dressing, HW-NFC dressing and LW-NFC dressing) were distributed logically according to the NFC amount of each sample and were all thicker than the Commercial nonwoven. However, the manually produced samples (NFC dressing type 4 and Anionic NFC dressing) were thinner than the uncoated Commercial nonwoven. It seems that the manual processing has somehow flatten the samples. This may be due to the nip pressure and five thin coats applied during the manual production method.

The changes in wound dressing area were measured for all the samples as they were wetted and dried after the wetting. There were no major differences observed in the behavior of the dressing during the measurements. When wetted, most samples swelled approximately 1 mm in width which corresponded about +2% area change. However, the NFC-film stood out from other samples as its area changed +5.7%. When samples were dried, all samples shrank at least to original dimensions or bit smaller. It must be noted that under 2% change in area is so small that the method is not accurate enough to quantify it reliably. So, most of these results are only approximate.

Fluid Handling Properties

Figure 24:
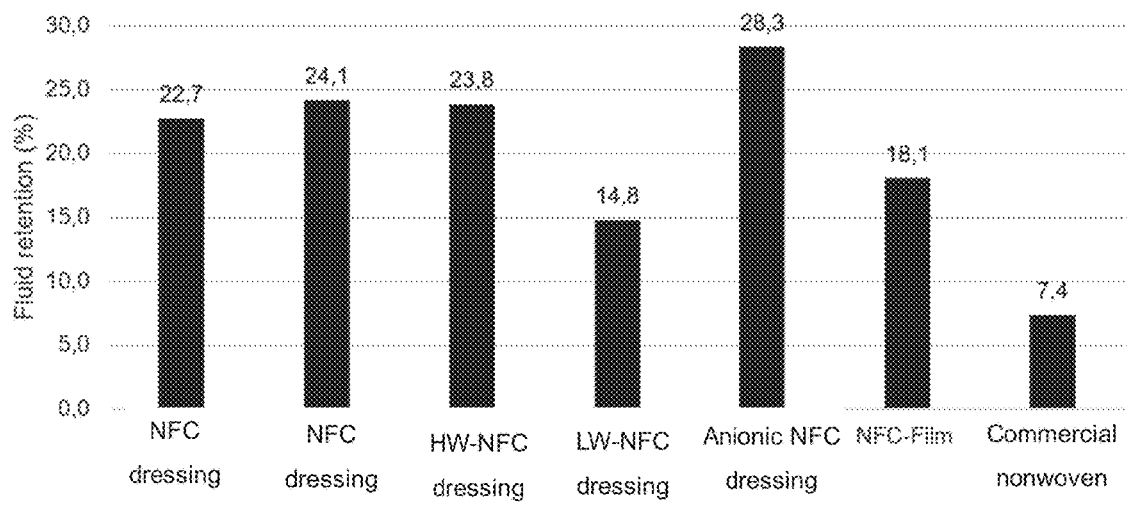
FIG. 24 shows a column chart of sample fluid retention (%).

Fluid retention describes the samples ability to hold the absorbed liquid under external load. A column chart of fluid retention is presented in FIG. 24. The column chart shows that the higher absorption capacity of Commercial nonwoven is compensated with a relatively modest fluid retention. On the other hand, NFC coated samples have better fluid retention overall, anionic NFC dressing giving the highest value of 28.3%. NFC dressing, NFC dressing type 4 and HW-NFC dressing all have very similar fluid retentions.

Figure 25:
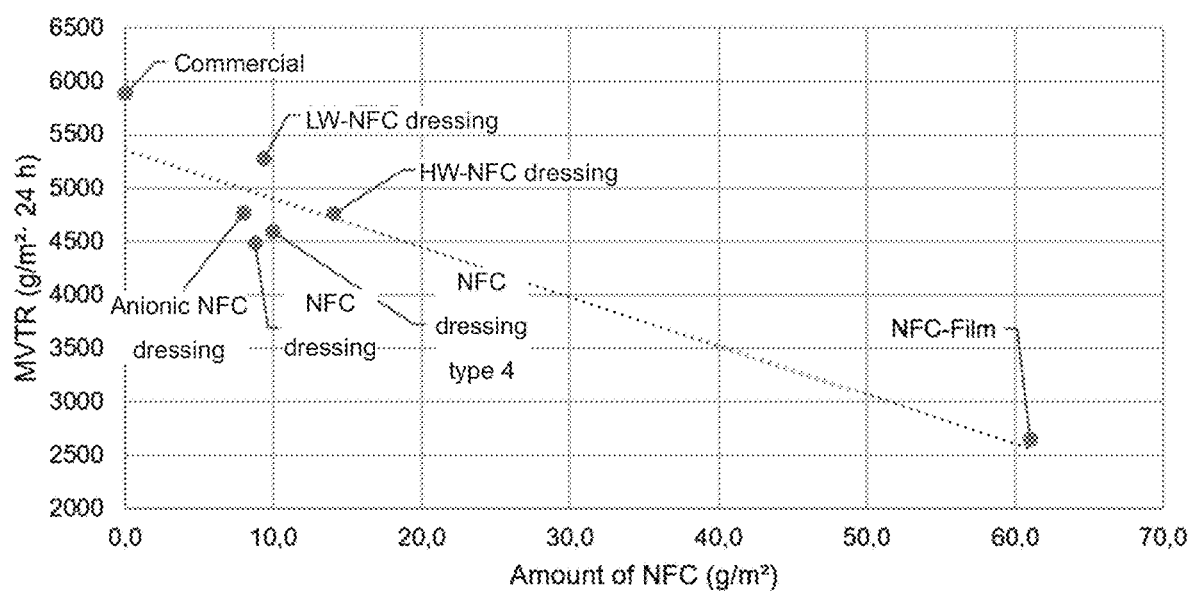
FIG. 25 shows the correlation of wound dressing NFC amount and moisture vapor transmission rate.

A simple graph about the correlation of NFC amount (g/m$^2$) and the moisture vapor transmission rate is shown in FIG. 25. Yet again the x-axis location of LW-NFC dressing data point is expected to be distorted and in reality, lie closer to 7 g/m$^2$ mark.

Table 5 shows results from another tested lot of non-sterile medical products according to embodiments. The table also presents suitable standard methods for determining the measured properties.

passing the immersed nonwoven fabric through a prefined gap to remove excess NFC hydrogel accumulated onto the nonwoven and to define the thickness of the coating on the immersed nonwoven fabric without pressing, and dewatering the immersed nonwoven fabric, to obtain the medical product comprising a supporting layer comprising the nonwoven fabric, and an absorbent layer as the coating on the nonwoven fabric, wherein the absorbent layer comprises unpressed nanofibrillar cellulose, and wherein dewatering the immersed nonwoven fabric does not involve vacuum or pressing.

2. The method of claim 1, comprising repeating the immersing and passing through the gap at least once.

3. The method of claim 1, comprising passing the immersed nonwoven fabric through the prefined gap formed between two limiting parts to define the thickness of the immersed nonwoven fabric.

4. The method of claim 3, wherein the two limiting parts comprise a pair of rollers, a roller and a blade, a roller and a plate, a pair of plates or a pair of blades.

5. The method of claim 1, wherein the dewatering is carried out by evaporating, by using non-contact drying, or by using contact drying.

6. The method of claim 5, wherein the dewatering is carried out by non-contact drying comprising drying with an infrared dryer, floating dryer, or impingement dryer, or wherein the dewatering is carried out by contact drying comprising drying with a press dryer, cylinder dryer (drying cylinder) or belt dryer.

7. The method of claim 1, wherein the nanofibrillar cellulose, when dispersed in water, provides a zero shear viscosity in the range of 1000-100000 Pa·s and a yield stress in the range of 1-50 Pa, determined by rotational rheometer at a consistency of 0.5% (w/w) by weight in aqueous medium at 22° C.±1° C. and/or wherein the nanofibrillar cellulose has an average fibril diameter of 200 nm or less.

8. The method of claim 1, wherein the nanofibrillar cellulose, when dispersed in water, provides a zero shear

TABLE 5

| | | | Description | | | | | |
|---|---|---|---|---|---|---|---|---|
| LIMSnro | Unit | Method | Sample 1 18-01691-001 | Sample 2 18-06216-008 | Sample 3 19-06278-003 | Sample 4 19-06278-004 | Sample 5 19-06278-005 | Sample 6 19-06278-006 |
| Absoprtion capacity | g/100 cm$^2$ | SFS-EN 13726-1 | 2.1 | 2.2 | 2.1 | 2.2 | 2.2 | 2.2 |
| Fluid retention | % | Internal | | | | 24.1 | 35.8 | 25.0 |
| Grammage | g/m$^2$ | ISO 536 | 53.3 | 53.8 | 52.9 | 56.2 | 55.2 | 55.8 |
| MVTR | g/m$^2$ * 24 h | SFS-EN 13726-2: 2002 | | 4600 | 4657 | 4242 | 4716 | 4571 |
| Air permeance Bendtsen | ml/min | ISO 5636-3 | 56 | 136 | 129 | 66 | 72 | 109 |

The invention claimed is:

1. A method for preparing a medical product, the method comprising
providing an aqueous dispersion of nanofibrillar cellulose (NFC),
providing a nonwoven fabric,
immersing the nonwoven fabric in the aqueous dispersion of nanofibrillar cellulose to form a coating on the nonwoven fabric, viscosity in the range of 5000-50000 Pa·s and a yield stress in the range of 3-15 Pa, determined by rotational rheometer at a consistency of 0.5% (w/w) by weight in aqueous medium at 22° C.±1° C. and/or wherein the nanofibrillar cellulose has an average fibril diameter in the range of 1-200 nm.

9. A medical product obtained with the method of claim 1, wherein the absorbent layer comprises unpressed nanofibrillar cellulose having an average fibril diameter of 200 nm or less, and wherein the content of the nanofibrillar cellulose decreases from the surfaces of the nonwoven fabric towards the middle of the nonwoven fabric between the surfaces.

10. The medical product of claim 9, wherein the nonwoven fabric comprises natural fabric, synthetic fabric or semi-synthetic fabric, or a mixture thereof.

11. The medical product of claim 10, wherein the natural fabric comprises cellulose or cotton fabric, the synthetic fabric or the semi-synthetic fabric comprises viscose or polyester, or the nonwoven fabric comprises a mixture of polypropylene and cellulose or a mixture of polypropylene, polyester and cellulose.

12. The medical product of claim 9, wherein the nanofibrillar cellulose comprises chemically unmodified nanofibrillar cellulose.

13. The medical product of claim 9, wherein the nanofibrillar cellulose comprises chemically anionically modified nanofibrillar cellulose having an average diameter of a fibril of 50 nm or less.

14. The medical product of claim 9, wherein the medical product has a fluid retention in the range of 14.5-40%.

15. The medical product of claim 9, wherein the medical product has a moisture vapor transmission rate (MVTR) in the range of 4000-5500 g/m$^2$/24 h.

16. The medical product of claim 9 comprising one or more cosmetic agents, one or more bioactive agents and/or one or more therapeutic agents.

17. The medical product of claim 9 having a moisture content in the range of 0-10%.

18. A method for treating and/or covering skin wounds or other damages or injuries in a subject, the method comprising
providing the medical product of claim 9,
applying the medical product onto the wounds, damages, or injuries.

19. The method of claim 18, wherein the skin wounds or other damages or injuries comprise deep skin wounds involving dermis damage.

20. The method of claim 18 comprising applying the medical product onto the wound to absorb bioactive agents from the wounds, storing the bioactive agents in the medical product for a period of time, and allowing the bioactive agents to diffuse back to the wound at a later phase of the healing process of the wounds.

21. The method of claim 18, wherein the medical product comprises one or more cosmetic agents, one or more bioactive agents and/or one or more therapeutic agents.

22. The method of claim 18, wherein the skin wounds are covered with a graft, the method comprising applying the medical product onto the graft.

23. The method of claim 1, wherein the content of the nanofibrillar cellulose decreases from the surfaces of the nonwoven fabric towards the middle of the nonwoven fabric between the surfaces.

24. The method of claim 1, wherein the nonwoven fabric comprises synthetic fibers and fibers selected from natural and semi-synthetic fibers.

25. The medical product of claim 9, wherein the nonwoven fabric comprises synthetic fibers and fibers selected from natural and semi-synthetic fibers.

26. The method of claim 1, wherein the nonwoven fabric comprises a mixture of polypropylene and cellulose, a mixture of polypropylene, polyester, and cellulose, a mixture of viscose and polypropylene, or a mixture of viscose and polyester.

27. The medical product of claim 9, wherein the nonwoven fabric comprises a mixture of polypropylene and cellulose, a mixture of polypropylene, polyester, and cellulose, a mixture of viscose and polypropylene, or a mixture of viscose and polyester.

28. The method of claim 1, wherein the absorbent layer has a thickness of at least 5 micrometers.

29. The medical product of claim 9, wherein the absorbent layer has a thickness of at least 5 micrometers.

30. The method of claim 1, wherein immersing the nonwoven fabric in the aqueous dispersion of nanofibrillar cellulose is for a time of 15 to 90 seconds to form the coating on the nonwoven fabric.

31. The medical product of claim 9, wherein the absorbent layer comprises unvacuumed nanofibrillar cellulose.

* * * * *